United States Patent [19]

Umezawa et al.

[11] Patent Number: 4,477,443
[45] Date of Patent: Oct. 16, 1984

[54] TYLOSIN DERIVATIVES, THEIR PREPARATION AND PHARMACEUTICAL COMPOSITIONS CONTAINING THEM

[75] Inventors: Hamao Umezawa; Sumio Umezawa, both of Tokyo; Tsutomu Tsuchiya, Kanagawa; Tomio Takeuchi, Tokyo; Akihiro Tanaka, Kanagawa; Hidenori Iwamoto, Saitama; Shuichi Sakamoto, Tokyo, all of Japan

[73] Assignee: Zaidan Hojin Biselbutsu Kagaku Kenkyu Kai (Microbial Chemistry Research Foundation), Tokyo, Japan

[21] Appl. No.: 395,463

[22] Filed: Jul. 6, 1982

[30] Foreign Application Priority Data

Jul. 9, 1981 [JP] Japan .................. 56-107485
Sep. 29, 1981 [JP] Japan .................. 56-154068
Nov. 30, 1981 [JP] Japan .................. 56-192627

[51] Int. Cl.³ .................. A61K 31/71; C07H 17/08
[52] U.S. Cl. .................. 424/180; 536/7.1; 536/17.4; 536/18.7; 536/122; 536/124
[58] Field of Search .................. 536/7.1, 7.4, 7.2, 17.4, 536/18.4, 18.5, 18.7, 124, 122, 55.2, 55.3; 424/180

[56] References Cited

U.S. PATENT DOCUMENTS 2,060,850 11/1936 Calcott et al. .................. 536/55.3
2,684,961 7/1954 Barham .................. 536/122
4,110,530 8/1978 Sciavolino .................. 536/7.2
4,304,856 12/1981 Baltz et al. .................. 536/7.1
4,373,095 2/1983 Ganguly et al. .................. 536/7.1
4,401,660 8/1983 Kirst .................. 536/7.1

FOREIGN PATENT DOCUMENTS 2045246 10/1980 United Kingdom .................. 536/122

OTHER PUBLICATIONS

Houber Weyl, 1957, pp. 985-988.

Primary Examiner—Johnnie R. Brown
Attorney, Agent, or Firm—Burgess, Ryan & Wayne

[57] ABSTRACT

Tylosin compounds of the formula

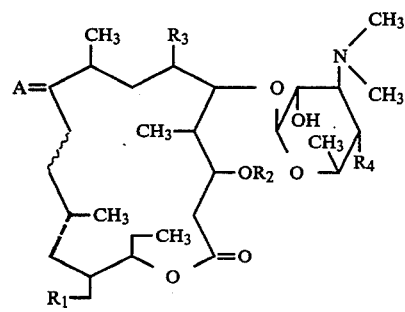

wherein $R_1$ represents a hydroxyl group; a halogen atom;

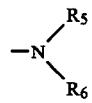

group (wherein $R_5$ is a hydrogen atom or a lower alkyl group which may be substituted by a hydroxyl group and $R_6$ is a hydrogen atom, a lower alkyl group which may be substituted by a hydroxyl group, an aryl group, an aralkyl group, a cycloalkyl group having 3–10 carbon atoms, $-CO(O)_m-R_7$ group (wherein m is 0 or 1 and $R_7$ is a lower alkyl group, an aryl group, an aralkyl group, a furanyl group, or a pyridyl group), or $-CH_2-R_{13}$ group (wherein $R_{13}$ is a mono-, di-, or trifluoromethyl group)); $-N(CH_2)_n$ group (wherein n is an integer of 2–15) which may be substituted by an oxo group, a hydroxyl group, a lower alkyl group, or a hydroxy lower alkyl group; an imidazolyl group, a morpholino group, or a piperazino group each may be substituted by a lower alkyl group; or $-OOCCH_2-R_8$ group (wherein $R_8$ is

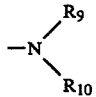

group (wherein $R_9$ and $R_{10}$, which may be the same or different, each is a hydrogen atom or a lower alkyl group; said $R_9$ and $R_{10}$ may be combined with each other to form an alkylene group having 3–7 carbon atoms) or $-S-R_{11}$ group (wherein $R_{11}$ is a furanyl group or a pyridyl group)); $R_2$ represents a hydrogen atom or a lower alkanoyl group; $R_3$ represents a methyl group or $-CH_2CHO$ group; $R_4$ represents a hydrogen atom or a hydroxyl group; A represents O=,

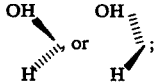

line ∼ represents a single bond or a double bond; and line ---- represents a single bond, a double bond, or ⌒ ; however, when said $R_1$ is a hydroxyl group, said $R_3$ is a methyl group and $R_4$ is a hydrogen atom, or said line ---- is ⌒ ; or when said $R_1$ is a halogen atom, said $R_3$ is a methyl group of said line ---- is ⌒.

The foregoing compounds of this invention are useful as antibiotics.

18 Claims, No Drawing

TYLOSIN DERIVATIVES, THEIR PREPARATION AND PHARMACEUTICAL COMPOSITIONS CONTAINING THEM

DETAILED DESCRIPTION OF THE INVENTION

This invention relates to tylosin derivatives, and more particularly to tylosin derivatives useful as excellent antibiotics.

Tylosin itself is a useful compound which is practically used as a macrolide antibiotic but the tylosin derivatives shown by the following formula provided by the present invention are very useful compounds having greater antibiotic activity than tylosin;

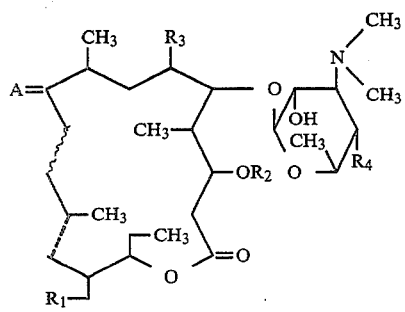

wherein $R_1$ represents a hydroxyl group; a halogen atom;

group (wherein $R_5$ represents a hydrogen atom or a lower alkyl group which may be substituted by a hydroxyl group and $R_6$ represents a hydrogen atom, a lower alkyl group which may be substituted by a hydroxyl group, an aryl group, an aralkyl group, a cycloalkyl group having 3-10 carbon atoms, $-CO(O)_m-R_7$ group (wherein m represents 0 or 1 and $R_7$ represents a lower alkyl group, an aryl group, an aralkyl group, a furanyl group, or pyridyl group), or $-CH_2-R_{13}$ group (wherein $R_{13}$ represents a mono-, di-, or trifluoromethyl group)); $-N(CH_2)_n$ group (wherein n represents an integer of 2-15) which may be substituted by an oxo group, a hydroxyl group, a lower alkyl group, or a hydroxy lower alkyl group; an imidazolyl group, a morpholino group, or a piperazino group each may be substituted by a lower alkyl group; or $-OOCCH_2-R_8$ group (wherein $R_8$ represents

group (wherein $R_9$ and $R_{10}$, which may be the same or different, each represents a hydrogen atom of a lower alkyl group; said $R_9$ and $R_{10}$ may be combined with each other to form an alkylene group having 3-7 carbon atoms) or $-S-R_{11}$ group (wherein $R_{11}$ represents a furanyl group or a pyridyl group)); $R_2$ represents a hydrogen atom or a lower alkanoyl group; $R_3$ represents a methyl group or $-CH_2CHO$ group; $R_4$ represents a hydrogen atom or a hydroxyl group; A represents $O=$,

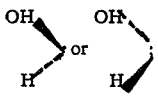

line ⁓ represents a single bond or a double bond; and line ---- represents a single bond, a double bond, or ⟨⊙⟩; however, when said $R_1$ is a hydroxyl group, said $R_3$ is a methyl group and $R_4$ is a hydrogen atom, or said line ---- is ⟨⊙⟩; or when said $R_1$ is a halogen atom, said $R_3$ is a methyl group or said line ---- is ⟨⊙⟩.

In the foregoing tylosin derivatives shown by formula I, the lower alkyl group is a straight or branched alkyl group having 1-6 carbon atoms, such as, for example, methyl group, ethyl group, isopropyl group, butyl group, tert-butyl group, pentyl group, hexyl group, etc. Also, examples of the aryl group are phenyl group, naphthyl group, etc., examples of the aralkyl group are benzyl group, phenethyl group, phenylpropyl group, etc., and examples of the lower alkanoyl group are acetyl group, propionyl group, butyryl group, etc.

The compounds of this invention shown by formula I can be prepared by the following methods:

METHOD 1

The compound shown by general formula I-a

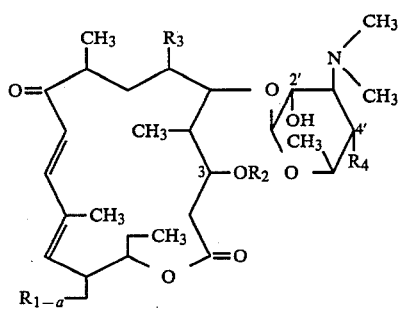

wherein $R_{1-a}$ represents

group (wherein $R_5$ is a hydrogen atom or a lower alkyl group which may be substituted by a hydroxyl group and $R_6'$ is a hydrogen atom, a lower alkyl group which may be substituted by a hydroxyl group, an aryl group, an aralkyl group, or a cycloalkyl group having 3-10 carbon atoms); $-N(CH_2)_n$ group (wherein n is an integer of 2-15) which may be substituted by an oxo group, hydroxyl group, lower alkyl group, or a hydroxy lower alkyl group; or an imidazolyl group, a morpholino group, or a piperazino group each may be substituted by a lower alkyl group, $R_2$ is a hydrogen atom or a lower alkanoyl group; $R_3$ is a methyl group or a $-CH_2CHO$ group; and $R_4$ is a hydrogen atom or a hydroxyl group and can be prepared by reacting a compound shown by formula II

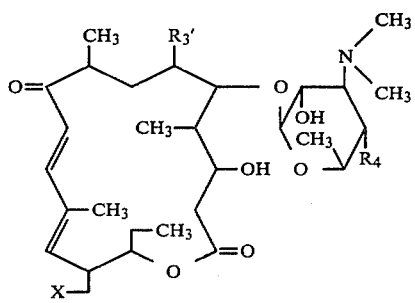

II wherein X represents a halogen atom, $R_3'$ represents a methyl group or a —$CH_2$-protected aldehyde group, and $R_4$ has the same significance as defined in formula I with a compound shown by formula III

III wherein $R_{1-a}$ has the same significance as defined in formula I-a and then, when $R_3'$ of the product is a —$CH_2$-protected aldehyde group, (i) releasing the protective group for the aldehyde group or (ii)-(a) reacting the product with a carboxylic acid compound shown by formula IV

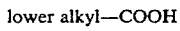

IV or the reactive derivative thereof, (b) treating the reaction product with an alcohol, and (c) releasing the protective group for the aldehyde group.

The foregoing protected aldehyde group is an aldehyde group protected in the form of acetal or thioacetal and, for example, there are dimethylacetal, diethylacetal, diethylthioacetal, ethyleneacetal, ethylenethioacetal, propyleneacetal, and these acetals having a substituent such as a lower alkyl group.

Also, as the reactive derivatives of the carboxylic acid compound of formula IV, an acid anhydride, an acid halide, etc., can be used.

It is preferred that the reaction of the compound of formula II and the compound of formula III be performed in an organic solvent such as tetrahydrofuran, acetonitrile, dioxane, dimethylformamide, dimethyl sulfoxide, etc., at room temperature or under heating.

The release of the protective group for the aldehyde group can be usually performed by treating the product with an inorganic acid such as hydrochloric acid, sulfuric acid, etc., or an organic acid such as trifluoroacetic acid, trichloroacetic acid in the presence of water.

The reaction of the reaction product of the compound of formula II wherein $R_3'$ is a —$CH_2$-protected aldehyde group and the compound of formula III with the compound of formula IV or the reactive derivative thereof can be performed in a basic solvent such as pyridine, triethylamine, collidine, etc., or an organic solvent such as acetone, dimethyl sulfoxide, dimethylformamide in the presence of foregoing pyridine, triethylamine, collidine, etc., at room temperature or under heating. When the compound of formula IV is used in the free acid state, it is preferred to use a condensing agent such as N,N'-dicyclohexylcarbodiimide, N,N'-carbonylimidazole, etc. By the reaction, not only the hydroxyl group at the 3-position but also the hydroxyl group at the 2'-position (and, when $R_4$ is a hydroxyl group, the hydroxyl group at the 4'-position) are simultaneously converted into a lower alkanoyloxy group and hence the reaction product is allowed to stand at room temperature or heated in an alcohol such as methanol, ethanol, etc., to hydrolyze the alkanoyloxy group at the 2'-position (and at the 4'-position).

When $R_{1-a}$ in the compound of formula III is a group having an oxo group, such as a piperidone, it is preferred to use the compound of which the oxo group is protected as a form of dimethylketal, etc.

METHOD 2

The compound shown by formula I-b

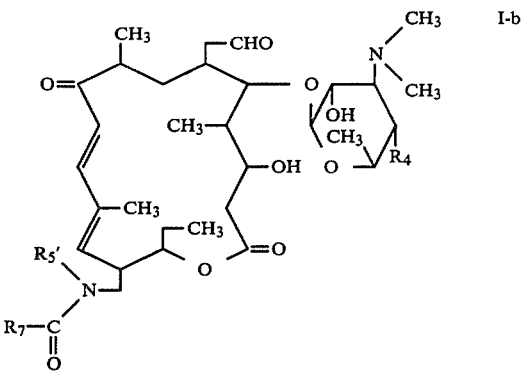

I-b wherein $R_5'$ is a lower alkyl group and $R_4$ and $R_7$ have the same significance as defined above, can be prepared by (a) reacting the compound of formula II wherein $R_3'$ is the protected aldehyde group with the compound of formula IV or the reactive derivative thereof, (b) reacting the product thus obtained with a compound shown by formula V

V wherein $R_5'$ has the same significance as described above, to provide a compound shown by the following formula VI

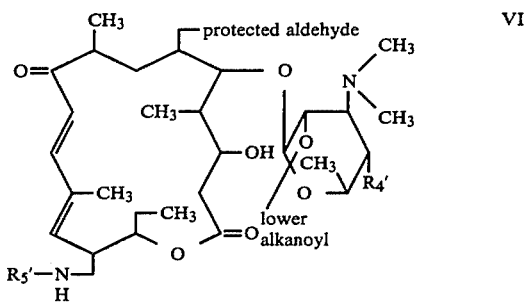

VI wherein $R_4'$ is a hydrogen atom or a lower alkanoyloxy group and $R_5'$ has the same significance as defined above, (c) reacting the product thus obtained with a carboxylic acid compound of formula VII

VII wherein $R_7$ has the same significance as defined above, or the reactive derivative thereof, (d) treating the product with an alcohol, and (e) releasing the protective group for the aldehyde group.

The order of the foregoing reactions (a) and (b) may be reversed.

As the reactive derivative of the carboxylic acid compound of formula VII, an acid anhydride, an acid halide, etc., are usually used.

It is preferred to perform the reaction of the compound of formula II wherein $R_3'$ is the protected aldehyde group with the compound of formula IV or the reactive derivative thereof in a nonprotonic solvent such as acetonitrile, acetone, dimethyl sulfoxide, dioxane, etc., at room temperature or under cooling so that the hydroxyl group at the 3-position is not converted into a lower alkanoyl group.

Then, the reaction of the reaction product and the compound of formula V can be performed in the foregoing solvent under heating, preferably under refluxing.

The reaction of the compound of formula VI and the compound of formula VII or the reactive derivative thereof can be performed in the foregoing solvent at room temperature. In the case of using the compound of formula VII in this reaction, it is preferred to use a condensing agent such as N,N'-dicyclohexylcarbodiimide, N,N'-carbonylimidazole, etc.

The treatment of the product with an alcohol can be performed by allowing the product to stand at room temperature or heating the product in an alcohol such as methanol, ethanol, etc. The protective group for the aldehyde group can be removed in the same manner as Method 1.

METHOD 3

The compound shown by formula I-C

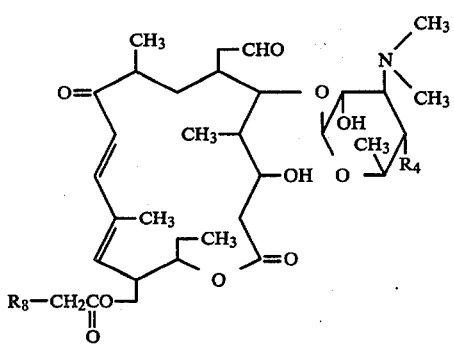

wherein $R_4$ and $R_8$ have the same significance as defined above can be prepared by (a) reacting the compound shown by formula VIII

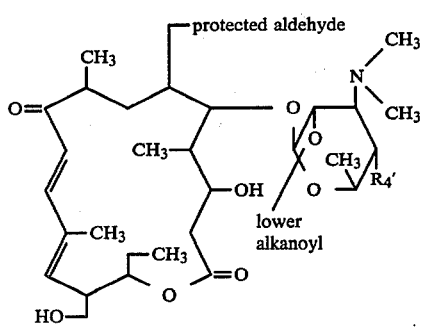

wherein $R_4'$ has the same significance as defined above with the compound shown by formula IX $$X'-COCH_2-X \qquad \text{IX}$$

wherein X and X' represent the same or different halogen atoms, to provide the compound shown by formula X

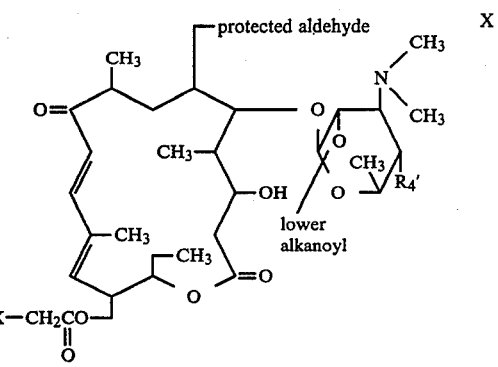

wherein X and $R_4'$ have the same significance as defined above, (b) reacting the compound of foregoing formula X with a compound shown by general formula XI

wherein $R_9$ and $R_{10}$ have the same significance as defined above or a compound shown by formula XII

wherein $R_{11}$ has the same significance as defined above and $R_{12}$ represents an alkali metal atom, (c) treating the product with an alcohol, and (c) releasing the protective group for the aldehyde group.

As the foregoing alkali metal atom, there are illustrated sodium, potassium, etc.

The reaction of the compound of formula VIII and the compound of formula IX can be performed in a basic solvent such as pyridine, triethylamine, etc., under cooling.

The reaction of the compound of formula X and the compound of formula XI or the compound of formula XII can be performed in an organic solvent such as acetonitrile, tetrahydrofuran, dioxane, dimethylformamide, dimethyl sulfoxide, etc. at room temperature.

The treatment of the product with an alcohol, can be preformed in the same manner as in Method 2 and also the release of the protective group for the aldehyde group can be performed in the same manner as in method 1.

METHOD 4

19-Decarbonyl-4'-deoxymycaminosyl tylonolide shown by formula I-d

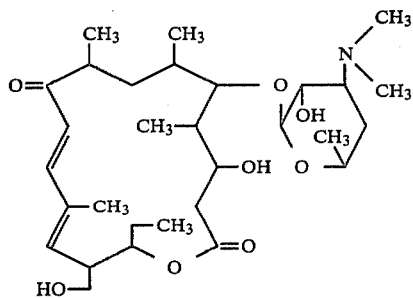

I-d can be prepared by reacting 4'-deoxymycaminosyl tylonolide with chlorotris(triphenylphosphino)rhodium: [(C₆H₅)₃P]₃RhCl.

The reaction can be performed in an organic solvent such as benzene, toluene, xylene, etc., at room temperature or under heating, preferably, in nitrogen stream.

METHOD 5

The compound shown by formula I-e

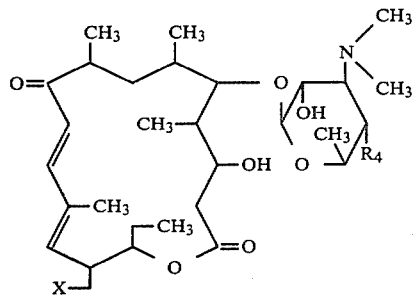

I-e wherein X and $R_4$ have the same significance as defined above, can be prepared by halogenating the compound shown by general formula XIII

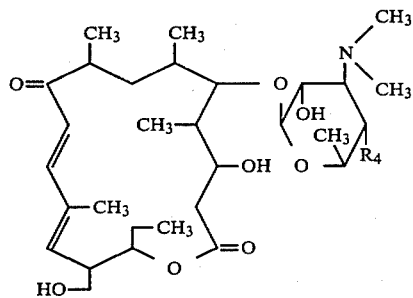

XIII wherein $R_4$ has the same significance as defined above.

The halogenation can be performed using a halogenating agent such as chlorine, bromine, iodine, carbon tetrachloride, carbon tetrabromide, carbon tetraiodide, etc., at room temperature or under cooling, preferably ice-cooling. It is preferred for accelerating the reaction to add triphenyl phosphine and, if necessary, a base such as pyridine, etc., to the reaction system. Some of these additives may act as a solvent but, if necessary, a solvent such as acetonitrile, tetrahydrofuran, dioxane, etc., may be used.

METHOD 6

The compound shown by formula I-f

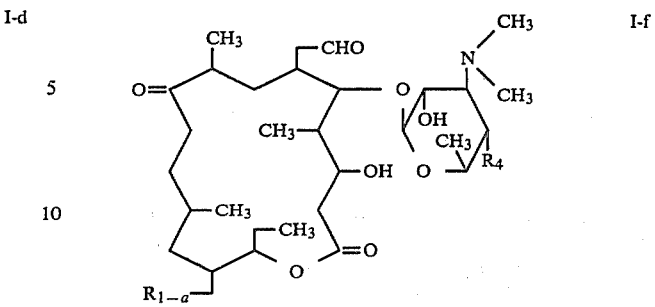

I-f wherein $R_{1-a}$ and $R_4$ have the same significance as defined above can be prepared by (a) catalytically reducing the compound shown by formula XIV

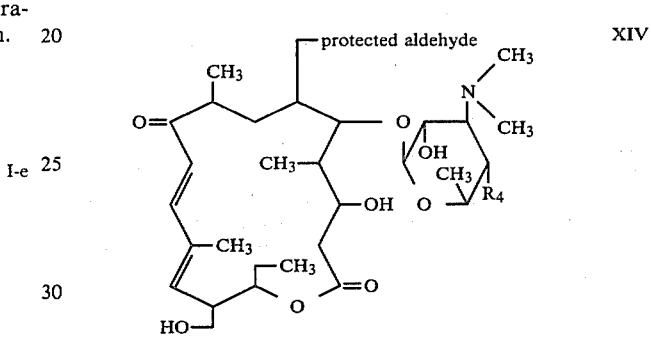

XIV wherein $R_4$ has the same significance as defined above (b) halogenating the product, (c) reacting the halogenated product with the compound of formula III, and (d) releasing the protective group for the aldehyde group.

In this method, the catalytic reduction of the compound of formula XIV can be performed by introducing hydrogen gas in an organic solvent such as methanol, ethanol, diethyl ether, tetrahydrofuran, ethyl acetate, etc., in the presence of a catalyst such as palladium, platinum, platinum black, etc.

The halogenation of the foregoing product can be performed in an organic solvent such as pyridine, acetonitrile, tetrahydrofuran, dioxane, etc., at room temperature or under cooling. In this case, it is particularly preferred to perform the halogenation under ice-cooling in nitrogen stream. As the halogenating agent, the halogenating agents used in method 5 can be used. In the halogenation step, the reaction can be accelerated by adding triphenyl phosphine and, if necessary, a base such as pyridine, etc., to the reaction system.

The reaction of the foregoing compound and the compound of formula III can be performed in an organic solvent such as tetrahydrofuran, acetonitrile, dioxane, dimethylformamide, dimethyl sulfoxide, etc., at room temperature or under heating.

Also, the release of the protective group for the aldehyde group can be performed in the same manner as in method 1.

METHOD 7

The compound shown by formula I-g

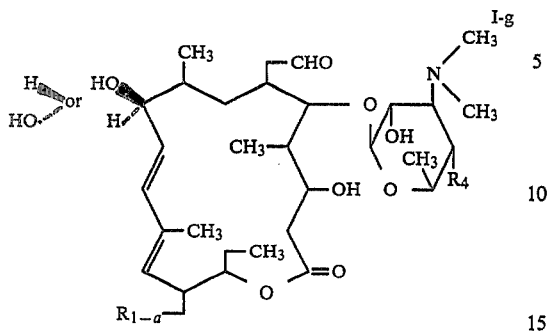

wherein $R_{1-a}$ and $R_4$ have the same significance as defined above, can be prepared by (a) reducing the reaction product of the compound of formula II wherein $R_3'$ is a —CH$_2$-protected aldehyde group and the compound of formula III using a hydrogenated metal complex compound, and (b) releasing the protected group for the aldehyde group.

Suitable examples of the hydrogenated metal complex compound used for the reducing reaction in the method are sodium borohydride, aluminum lithium hydride, etc., and the reducing reaction can be performed in an organic solvent such as methanol, ethanol, tetrahydrofuran, benzene, toluene, etc., under cooling.

The release of the protective group for the aldehyde group can be performed in the same manner as in method 1.

METHOD 8

The compound shown by formula I-h

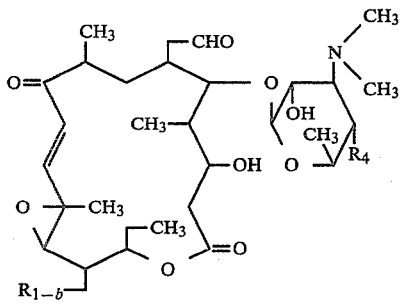

wherein $R_{1-b}$ represents a hydroxyl group or the groups as defined for $R_{1-a}$ and $R_4$ has the same significance as defined above, can be prepared by (a) treating the compound shown by formula XV

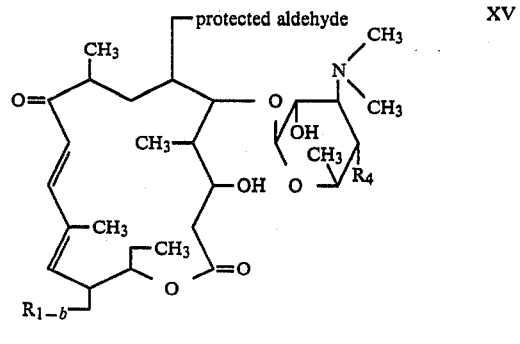

wherein $R_{1-b}$ and $R_4$ have the same significance as defined above, with a peracid, (b) treating the product with triphenylphosphine, and (c) releasing the protective group for the aldehyde group.

Suitable peracids used in the foregoing reaction are performic acid, peracetic acid, perbenzoic acid, etc. The treatment of the compound of formula XV with peracids can be performed in an organic solvent such as chloroform, ethyl acetate, methylene chloride, acetonitrile, dioxane, dimethylformamide, dimethyl sulfoxide, etc.

The treatment of the product with triphenylphosphine can be performed in the foregoing solvent under heating, preferably under refluxing in an argon stream.

The release of the protective group for the aldehyde group can be performed in the same manner as in method 1.

METHOD 9 the compound shown by formula I-i

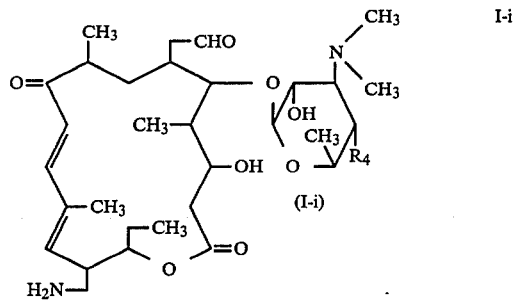

wherein $R_4$ has the same significance as defined above, can be prepared by (a) reacting the compound of formula II wherein $R_3'$ is the protected aldehyde group with sodium azide, (b) treating the product with an aqueous chromium chloride solution and (c) releasing the protective group for the aldehyde group.

The reaction of foregoing step (a) can be performed in an organic solvent such as dimethylformamide, acetone, acetonitrile, tetrahydrofuran, etc., under heating. The treatment of step (b) can be performed in an organic solvent such as acetone, acetonitrile, tetrahydrofuran, methanol, etc., under cooling, preferably in an argon gas atmosphere.

The release of the protective group for the aldehyde group can be performed in the same manner as in method 1.

METHOD 10

The compound shown by formula I-j

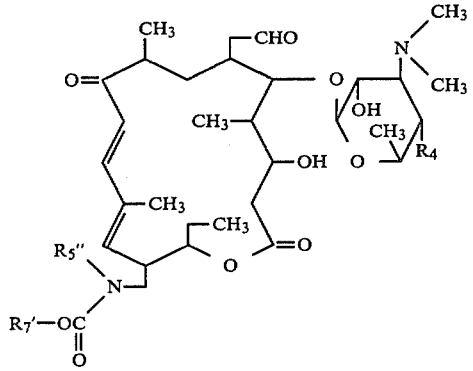

wherein $R_5''$ is a hydrogen atom or a lower alkyl group, $R_7'$ is a lower alkyl group, an aryl group, or an aralkyl group, and $R_4$ has the same significance as defined above, can be prepared by (a) reacting a compound shown by formula XVI

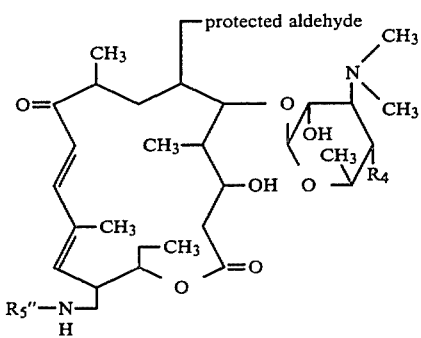

wherein $R_5''$ and $R_4$ have the same significance as defined above, with a compound shown by formula XVII

   XVII wherein $R_7'$ and X have the same significance as defined above, and (b) releasing the protective group for the aldehyde group.

The reaction of the compund of formula XVI and the compound of XVII can be performed in a water-containing organic solvent such as water-containing methanol, water-containing ethanol, water-containing acetone, water-containing tetrahydrofuran, etc., at room temperature. The release of the protective group for the aldehyde group can be performed in the same manner as in method 1.

METHOD 11

The compound shown by formula I-k

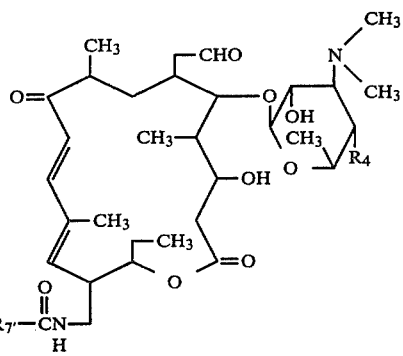

wherein $R_7'$ and $R_4$ have the same significance as defined above, can be prepared by (a) reacting the compound of formula XVI wherein $R_5''$ is a hydrogen atom with a compound shown by formula XVIII

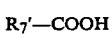   XVIII wherein $R_7'$ has the same significance as defined above, or the reactive derivative thereof and (b) releasing the protective group for the aldehyde group.

As the reactive derivative of the compound of formula XVIII, an acid halide, an acid anhydride, etc., can be used.

The reaction of foregoing step (a) can be performed under the same reaction conditions as in step (a) of method 10. Also, the release of the protective group for the aldehyde group can be performed in the same manner as in method 1.

METHOD 12

The coompound shown by formula I-l

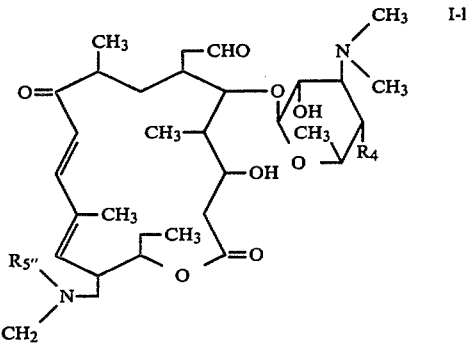

wherein $R_4$, $R_5''$ and $R_{13}$ have the same significance as defined above, can be prepared by (a) reacting the compound of formula XVI with a compound shown by formula XIX

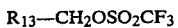   XIX wherein $R_{13}$ has the same significance as defined above, and (b) releasing the protective group for the aldehyde group.

The reaction of the compound of formula XVI and the compound of formula XIX can be performed in an organic solvent such as benzene, dimethylformamide, etc., under heating, preferably in the presence of a base such as triethylamine, pyridine, etc. The release of the protective group for the aldehyde group can be performed in the same manner as in method 1.

METHOD 13

The compound shown by formula I-m

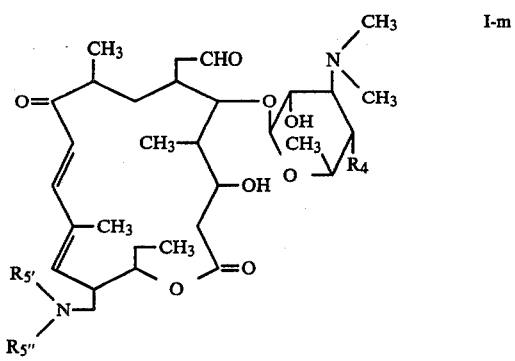

wherein $R_4$, $R_5'$, and $R_5''$ have the same significance as defined above, can be performed by (a) reacting the compound of formula XVI wherein $R_5''$ is a hydrogen atom with a lower alkyl halide and (b) releasing the protective group for the aldehyde group.

As the lower alkyl halide used in the above reaction, there are methyl iodide, ethyl iodide, t-butyl bromide, etc.

The reaction of the compound of formula XVI wherein $R_5''$ is a hydrogen atom and a lower alkyl halide can be performed in an organic solvent such as acetonitrile, acetone, dimethylformamide, etc., under heating.

When an equimolar amount of a lower alkyl halide is used, the compound of formula I-m wherein $R_5''$ is a hydrogen atom is obtained, while when a lower alkyl halide is used in an amount of 2 mole times that of the compound of formula XVI, the compound of formula I-m wherein $R_5''$ is a lower alkyl group is obtained. The release of the protective group for the aldehyde group can be performed in the same manner as in method 1.

The antimicrobial activity (MIC) of the tylosin derivatives of this invention are shown in Tables I and II.

TABLE I

| Microoganism/Example No. | 4 | 5 | 6 | 9 | 10 | 13 | 16 | 17 | 18 | 19 |
|---|---|---|---|---|---|---|---|---|---|---|
| Staph. aureus 193 | 0.39 | 0.78 | <0.2 | <0.2 | <0.2 | 0.39 | 1.56 | 0.78 | <0.2 | 0.2 |
| Staph. aureus 209 P | 0.2 | 0.78 | <0.2 | <0.2 | <0.2 | 0.39 | 0.39 | 0.39 | <0.2 | <0.2 |
| Staph. aureus MS 9861 | 1.56 | 12.5 | 1.56 | 0.39 | 0.78 | 0.78 | 3.12 | 1.56 | 0.78 | 0.78 |
| Sarcina lutea PCI 1001 | <0.2 | <0.2 | <0.2 | 0.2 | <0.2 | <0.2 | <0.2 | <0.2 | <0.2 | <0.2 |
| B. subtilis NRRL B-558 | 0.78 | 0.78 | 0.39 | <0.2 | <0.2 | 0.39 | 0.78 | 0.39 | <0.2 | 0.39 |
| Coryn. bovis 1810 | 0.78 | 0.78 | <0.2 | 0.2 | <0.2 | <0.2 | 0.39 | <0.2 | <0.2 | <0.2 |
| E. coli NIHJ | 0.78 | 1.56 | 0.78 | <0.2 | <0.2 | 0.78 | 1.56 | 0.78 | 0.39 | 0.39 |
| E. coli K-12 | 1.56 | 1.56 | 1.56 | 0.39 | 0.39 | 1.56 | 3.12 | 3.12 | 0.78 | 0.78 |
| E. coli K-12 R-5 | 1.56 | 1.56 | 1.56 | 0.39 | 0.39 | 1.56 | 1.56 | 1.56 | 0.78 | 0.78 |
| E. coli K-12 ML 1410 | 1.56 | 3.12 | 3.12 | 0.39 | 0.39 | 3.12 | 3.12 | 0.78 | 0.78 | 0.78 |
| E. coli K-12 LA 290 R 55 | 0.78 | 3.12 | 1.56 | 0.39 | 0.39 | 1.56 | 1.56 | 0.78 | 0.78 | 0.39 |
| Kleb. pneumoniae PCI 602 | 0.78 | 1.56 | 0.78 | 0.2 | 0.2 | 0.39 | 0.78 | 1.56 | 0.39 | 0.2 |
| Shigella dysenteriae JS 11910 | 0.39 | 1.56 | 0.39 | <0.2 | <0.2 | <0.2 | <0.2 | <0.2 | <0.2 | <0.2 |
| Sal. enteritidis 1891 | 1.56 | 3.12 | 1.56 | <0.2 | 0.39 | 0.78 | 0.39 | 0.39 | <0.2 | <0.2 |
| Pro. vulgaris OX-19 | 1.56 | 1.56 | 1.56 | 0.78 | 0.39 | 1.56 | 1.56 | 0.78 | 0.78 | 0.39 |
| Microoganism/Example No. | 25 | 26 | 27 | 28 | 29 | 31 | 32 | 76 | 78 | 80 |
| Staph. aureus 193 | 0.2 | 0.2 | 0.78 | <0.2 | 0.39 | 0.39 | 1.56 | 0.39 | <0.2 | <0.2 |
| Staph. aureus 209 P | <0.2 | <0.2 | <0.2 | <0.2 | 0.39 | <0.2 | 0.78 | 0.39 | <0.2 | <0.2 |
| Staph. aureus MS 9861 | 0.2 | 12.5 | 3.12 | 0.39 | 0.78 | 0.39 | 6.25 | 0.78 | 0.39 | <0.2 |
| Sarcina lutea PCI 1001 | 0.39 | <0.2 | <0.2 | <0.2 | <0.2 | <0.2 | <0.2 | <0.2 | <0.2 | <0.2 |
| B. subtilis NRRL B-558 | 3.12 | 50 | <0.2 | <0.2 | 0.39 | 0.39 | 1.56 | 0.78 | 0.39 | 0.39 |
| Coryn. bovis 1810 | <0.2 | <0.2 | <0.2 | 0.39 | <0.2 | 0.39 | 6.25 | <0.2 | <0.2 | <0.2 |
| E. coli NIHJ | 1.56 | 3.12 | 0.78 | 3.12 | 3.12 | 0.39 | 3.12 | 3.12 | 3.12 | 3.12 |
| E. coli K-12 | 3.12 | 12.5 | 3.12 | 6.25 | 25 | 0.78 | 25 | 6.25 | 12.5 | 6.25 |
| E. coli K-12 R-5 | 6.25 | 12.5 | 3.12 | 6.25 | 12.5 | 0.78 | 6.25 | 6.25 | 6.25 | 6.25 |
| E. coli K-12 ML 1410 | | | | | | | | | | |
| E. coli K-12 LA 290 R 55 | | | | | | | | | | |
| Kleb. pneumoniae PCI 602 | 0.39 | 0.78 | <0.2 | 1.56 | 3.12 | 0.78 | 25 | 3.12 | 3.12 | 1.56 |
| Shigella dysenteriae JS 11910 | 3.12 | 3.12 | <0.2 | 0.78 | 0.39 | 0.78 | 0.2 | 1.56 | 1.56 | 0.78 |
| Sal. enteritidis 1891 | 1.56 | 3.12 | <0.2 | 6.25 | 12.5 | 0.39 | 6.25 | 3.12 | 3.12 | 1.56 |
| Pro. vulgaris OX-19 | | | | | | | | | | |
| Microoganism/Example No. | 83 | 85 | Tylosin | | | | | | | |
| Staph. aureus 193 | <0.2 | 0.39 | 0.78 | | | | | | | |
| Staph. aureus 209 P | <0.2 | <0.2 | 0.39 | | | | | | | |
| Staph. aureus MS 9861 | 0.39 | 0.39 | 6.25 | | | | | | | |
| Sarcina lutea PCI 1001 | <0.2 | <0.2 | <0.2 | | | | | | | |
| B. subtilis NRRL B-558 | <0.2 | <0.2 | 0.78 | | | | | | | |
| Coryn. bovis 1810 | <0.2 | <0.2 | 0.2 | | | | | | | |
| E. coli NIHJ | 6.25 | 12.5 | 100 | | | | | | | |
| E. coli K-12 | 12.5 | 12.5 | >100 | | | | | | | |
| E. coli K-12 R-5 | 12.5 | 12.5 | >100 | | | | | | | |
| E. coli K-12 ML 1410 | | | >100 | | | | | | | |
| E. coli E. coli K-12 LA 290 R 55 | | | >100 | | | | | | | |
| Kleb. pneumoniae PCI 602 | 12.5 | 3.12 | 25 | | | | | | | |
| Shigella dysenteriae JS 11910 | 1.56 | 0.78 | 12.5 | | | | | | | |
| Sal. enteritidis 1891 | 6.25 | 12.5 | 25 | | | | | | | |

TABLE I-continued

| | MIC (γ/ml) |
|---|---|
| *Pro. vulgaris* OX-19 | >100 |

TABLE II

| | MIC (γ/ml) | | | | | | | | | | |
|---|---|---|---|---|---|---|---|---|---|---|---|
| | Example No. | | | | | | | | | | |
| Microorganism | 21 | 22 | 23 | 24 | 42 | 43 | 45 | 46 | 47 | 51 | 52 |
| *B. subtilis* ATCC 6633 | 0.78 | 0.78 | 1.56 | 0.78 | 0.78 | 0.78 | 0.39 | 1.56 | 0.78 | 0.78 | 1.56 |
| *B. cereus* | 0.39 | 0.39 | 0.78 | 0.39 | 0.39 | 0.39 | 0.39 | 0.39 | 0.39 | 0.39 | 1.56 |
| *Staph. aureus* ATCC 6538P | 0.78 | 0.78 | 0.78 | 0.39 | 0.78 | 0.78 | 0.78 | 1.56 | 0.78 | 0.78 | 0.78 |
| *Staph. aureus* KC-11 | 0.78 | 0.78 | 0.78 | 0.78 | 1.56 | 0.78 | 0.78 | 1.56 | 0.78 | 0.78 | 0.78 |
| *Staph. aureus* 226 | 0.78 | 0.78 | 0.78 | ≦0.2 | 0.78 | 0.78 | 0.78 | 1.56 | 1.56 | 0.78 | 0.78 |
| *Staph. epidermidis* IID 866 | 0.78 | 0.78 | 0.78 | 0.39 | 0.78 | 0.78 | 0.39 | 0.78 | 0.78 | 0.39 | 0.78 |

| | Example No. | | | | | | | | | | |
|---|---|---|---|---|---|---|---|---|---|---|---|
| Microorganism | 53 | 61 | 66 | 67 | 74 | 87 | 88 | 89 | 90 | 96 | Tylosin |
| *B. subtilis* ATCC 6633 | 0.39 | 0.78 | 1.56 | 0.78 | 0.78 | 0.78 | 0.78 | 0.78 | 0.39 | 0.78 | 0.78 |
| *B. cereus* | ≦0.2 | ≦0.2 | ≦0.2 | 0.39 | 0.78 | | | | | 0.39 | 0.78 |
| *Staph. aureus* ATCC 6538P | 0.39 | 0.78 | 0.78 | 0.78 | 0.78 | 0.78 | 0.78 | 0.78 | 0.39 | 0.39 | 1.56 |
| *Staph. aureus* KC-11 | 0.39 | 0.78 | 1.56 | 0.78 | 0.78 | 0.78 | 0.78 | 0.78 | 0.39 | 0.78 | 1.56 |
| *Staph. aureus* 226 | 0.39 | 1.56 | 1.56 | 0.78 | 0.78 | 0.78 | 0.78 | 0.78 | 0.39 | 0.78 | 1.56 |
| *Staph. epidermidis* IID 886 | ≦0.2 | 0.78 | 0.78 | 0.78 | 0.78 | 0.78 | 0.39 | 0.78 | 0.39 | 0.39 | 1.56 |

The compounds of this invention shown by formula I can be orally or parenterally administrated as tablets, capsules, powders, injections, liquids, etc., prepared using ordinary carriers for preparation. The doses of the medicaments are 10–1000 mg per single dose at 1–4 times a day.

Then, this invention will be explained in detail by the following examples.

In addition, in the following examples, NMR means a nuclear magnetic resonance spectrum, Anal. an elemental analytical value, IR an infrared absorption spectrum, UV a ultraviolet absorption spectrum, Mass a mass spectrum, and m.p. a melting point.

EXAMPLE 1

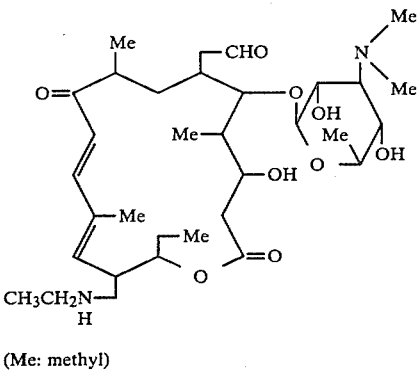

(Me: methyl)

(a) In 2.2 ml of anhydrous acetonitrile was dissolved 110 mg of 23-deoxy-23-iodomycaminosyl tylonolide diethylacetal, after adding 63.5 mg of ethylamine to the solution, the reaction was performed for 5 hours at 80° C., and thereafter, the reaction mixture was concentrated under reduced pressure. The residue was dissolved in 5.5 ml of chloroform, the solution was washed once with 2 ml of a saturated aqueous sodium hydrogen carbonate solution and then 2 ml of a saturated aqueous sodium sulfate solution, and after drying with anhydrous sodium sulfate, the solution was concentrated under reduced pressure. Then, the residue was subjected to a chromatographic treatment by a column of 11 g of silica gel using a solvent system of chloroform-methanol-aqueous ammonia (15:1:0.1) to provide 71.4 mg (yield 72.5%) of 23-deoxy-23-ethylaminomycaminosyl tylonolide diethylacetal.

(b) In 0.6 ml of acetonitrile was dissolved 30.5 mg of the foregoing product and after adding thereto 1.3 ml of 0.1N hydrochloric acid, the reaction was performed for 60 minutes.

After the reaction was over, 15 mg of sodium hydrogen carbonate was added to the reaction mixture and the reaction product was extracted thrice each time with 3 ml of chloroform. The chloroform layers were combined with each other and the mixture was washed twice each time with 1 ml of a saturated aqueous sodium sulfate solution and, after drying with anhydrous sodium sulfate, concentrated under reduced pressure. The residue was subjected to a chromatographic treatment by a column of 4 g of silica gel using a solvent system of chloroform-methanol-concentrated aqueous ammonia (12:1:0.1) to provide 24.0 mg (yield 89%) of 23-deoxy-23-ethylaminomycaminosyl tylonolide.

(i) NMR (CDCl$_3$):

| δ (ppm) | H number | Form | J (Hz) | |
|---|---|---|---|---|
| 2.54 | 6 | s | | 3'-NMe$_2$ |
| 2.80 | 2 | | | 23-NHCH$_2$CH$_3$ |
| 4.28 | 1 | d$_{1',2'}$ | 7.5 | H$_{1'}$ |
| 4.87 | 1 | m | | H$_{15}$ |
| 9.81 | 1 | s | | H$_{20}$ |

(ii) Colorless amorphous solid (reprecipitated from dichloromethane-n-hexane)

(iii) Anal. for C$_{33}$H$_{56}$N$_2$O$_9$:

| | C (%) | H (%) | N (%) |
|---|---|---|---|
| Calculated: | 63.44 | 9.03 | 4.48 |
| Found: | 63.21 | 8.75 | 4.50 |

(iv) $[\alpha]_D^{23}$ + 33° (c 0.7, CHCl$_3$)

EXAMPLE 2

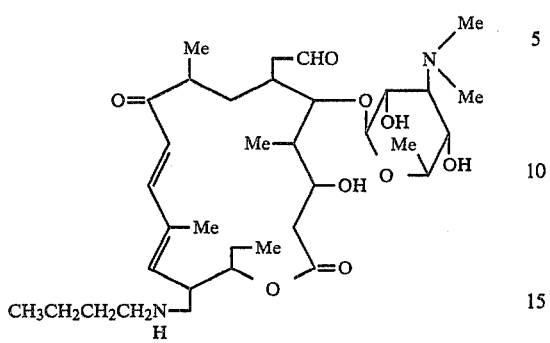

In 3 ml of anhydrous acetonitrile was dissolved 150 mg of 23-deoxy-23-iodomycaminosyl tylonolide diethylacetal, after adding thereto 70 mg of n-butylamine, the reaction was performed for 12 hours at 80° C., and the reaction mixture was concentrated under reduced pressure. The residue was dissolved in 7.5 ml of chloroform, the solution was washed once with 2.5 ml of a saturated aqueous sodium hydrogen carbonate solution and then 2.5 ml of a saturated aqueous sodium sulfate solution, and after drying with anhydrous sodium sulfate, the solution was concentrated under reduced pressure. In 2.4 ml of acetonitrile was dissolved 120 mg of the residue and after adding thereto 4.9 ml of 0.1N hydrochloric acid, the reaction was performed for 60 minutes. After the reaction was over, 64.5 mg of sodium hydrogen carbonate was added to the reaction mixture and the reaction product was extracted three times each time with 2.4 ml of chloroform. The chloroform layers thus obtained were combined with each other and the mixture was washed twice each time with 2.4 ml of a saturated aqueous sodium sulfate solution and, after drying with anhydrous sodium sulfate, concentrated under reduced pressure. The residue was subjected to a chromatographic treatment by a column of 12 g of silica gel using a solvent system of chloroform-methanol-concentrated aqueous ammonia (12:1:0.1) to provide 92.6 mg (yield 86%) of 23-deoxy-23-butylaminomycaminosyl tylonolide.

| (i) | NMR (CDCl$_3$) | | | | |
|---|---|---|---|---|---|
| | δ (ppm) | H number | Form | J (Hz) | |
| | 2.54 | 6 | s | | 3'-NMe$_2$ |
| | ~2.8 | 2 | | | 23-NHCH$_2$CH$_2$CH$_2$CH$_3$ |
| | 4.23 | 1 | d$_{1',2'}$ | 7.5 | H$_{1'}$ |
| | 4.86 | 1 | m | | H$_{15}$ |
| | 9.83 | 1 | s | | H$_{20}$ |
| (ii) | Colorless amorphous solid (reprecipitated from dichloromethane-n-hexane) | | | | |
| (iii) | Anal. for C$_{35}$H$_{60}$N$_2$O$_9$: | | | | |
| | | C (%) | H (%) | N (%) | |
| | Calculated: | 64.39 | 9.26 | 4.29 | |
| | Found: | 64.42 | 9.46 | 4.45 | |
| (iv) | $[\alpha]_D^{23}$ + 45° (c 1.0, CHCl$_3$) | | | | |

EXAMPLE 3

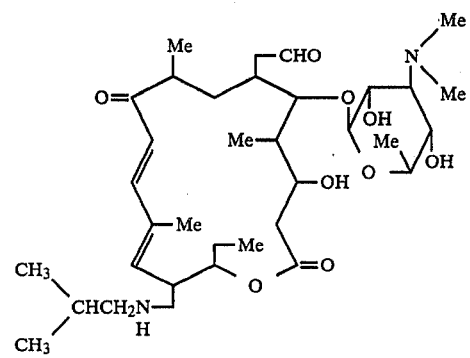

By following the same procedure as in Example 2 using 85.5 mg of 23-deoxy-23-iodomycaminosyl tylonolide diethylacetal and 40.2 mg of isobutylamine, 58.8 mg (yield 82%) of 23-deoxy-23-isobutylaminomycaminosyl tylonolide was obtained.

| (i) | NMR (CDCl$_3$): | | | | |
|---|---|---|---|---|---|
| | δ (ppm) | H number | Form | J (Hz) | |
| | 2.55 | 6 | s | | 3'-NMe$_2$ |
| | ~2.6 | 2 | | | 23-N—CH$_2$CH(CH$_3$)$_2$H |
| | 4.24 | 1 | d$_{1',2'}$ | 7.5 | H$_{1'}$ |
| | 4.85 | 1 | m | | H$_{15}$ |
| | 9.82 | 1 | s | | H$_{20}$ |
| (ii) | Colorless amorphous solid (reprecipitated from dichloromethane-n-hexane) | | | | |
| (iii) | Anal. for C$_{35}$H$_{60}$N$_2$O$_9$: | | | | |
| | | C (%) | H (%) | N (%) | |
| | Calculated: | 64.39 | 9.26 | 4.29 | |
| | Found: | 64.21 | 9.09 | 4.52 | |
| (iv) | $[\alpha]_D^{23}$ + 48° (c 1.0, CHCl$_3$). | | | | |

EXAMPLE 4

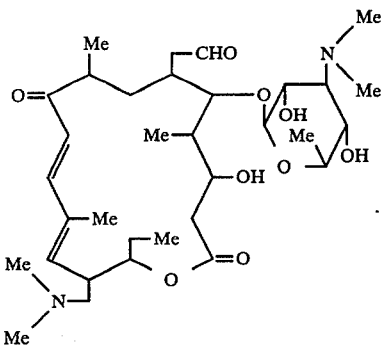

In 3.4 ml of anhydrous acetonitrile was dissolved 170.9 mg of 23-deoxy-23-iodomycaminosyl tylonolide diethylacetal and after adding 0.440 ml of a 4.98M dimethylamine acetonitrile solution to the solution, the reaction was performed for 30 minutes at 80° C. Then, 0.440 ml of a 4.98M dimethylamine acetonitrile solution was added again to the reaction mixture and the reaction was further performed for 30 minutes.

The reaction mixture was concentrated under reduced pressure to remove acetonitrile and after adding thereto chloroform, the mixture was concentrated again. The residue was dissolved in 8 ml of chloroform and the solution was washed once with 2 ml of a saturated aqueous sodium hydrogen carbonate solution and then twice each time with 2 ml of a saturated aqueous sodium sulfate solution, and then concentrated under reduced pressure.

After adding benzene to the residue, the mixture was concentrated and after adding benzene-n-hexane to the residue thus formed, the mixture was allowed to stand to provide 149.7 mg (yield 98%) of the crystals of 23-deoxy-23-dimethylaminomycaminosyl tylonolide diethylacetal.

In 1.8 ml of acetonitrile was dissolved 88.4 mg of the foregoing product and after adding 4.80 ml of 0.1N hydrochloric acid to the solution, the reaction was performed for 75 minutes. After neutralizing the solution by the addition of 44 mg of sodium hydrogencarbonate and 1 ml of a saturated aqueous sodium hydrogen carbonate solution, the reaction product was extracted three times each time with 2 ml of chloroform. The chloroform layers were combined with each other and the mixture was washed twice each time with 2 ml of a saturated aqueous sodium sulfate solution and, after drying with anhydrous sodium sulfate, concentrated under reduced perssure.

The residue was charged in a column, in which 9 g of silica gel was filled with a solution system of chloroform-methanol-concentrated aqueous ammonia (30:1:0.1), using the solvent having the same composition as above and a chromatographic treatment was performed using a solvent system of chloroform-methanol-concentrated aqueous ammonia (15:1:0.1) to provide 67.9 mg (yield 86%) of 23-deoxy-23-dimethylaminomycaminosyl tylonolide.

(i) NMR (CDCl$_3$):

| δ (ppm) | H number | Form | J (Hz) | |
|---|---|---|---|---|
| 2.22 | 6 | s | | 23-NMe$_2$ |
| 2.54 | 6 | s | | 3'-NMe$_2$ |
| 4.28 | 1 | d$_{1',2'}$ | 7.5 | H$_{1'}$ |
| 9.80 | 1 | s | | H$_{20}$ |

(ii) Colorless amorphous solid (reprecipitated from acetone-n-hexane)
(iii) Anal. for C$_{33}$H$_{56}$N$_2$O$_9$:

| | C (%) | H (%) | N (%) |
|---|---|---|---|
| Calculated: | 63.44 | 9.03 | 4.48 |
| Found: | 63.70 | 9.02 | 4.25 |

(iv) $[\alpha]_D^{23}$ + 18° (c 1.0, CHCl$_3$).

EXAMPLE 5

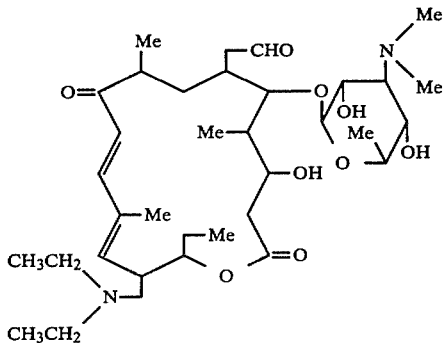

By treating 152.1 mg of 23-deoxy-23-iodomycaminosyl tylonolide diethyl acetal and 0.2 ml of diethylamine as in Example 1-a), 129.7 mg (yield 92%) of 23-deoxy-23-diethylaminomycaminosyl tylonolide diethyl acetal was obtained, and then treating 36.1 mg of the product thus obtained as in Example 1-b), 31.7 mg (yield 98%) of 23-deoxy-23-diethylamino mycaminosyl tylonolide was obtained.

(i) NMR (CDCl$_3$):

| δ (ppm) | H number | Form | J (Hz) | |
|---|---|---|---|---|
| ~2.47 | | | | 23-N(CH$_2$CH$_3$)$_2$ |
| 2.55 | 6 | s | | 3'-NMe$_2$ |
| 4.30 | 1 | d$_{1',2'}$ | 7.5 | H$_{1'}$ |
| 4.78 | 1 | m | | H$_{15}$ |
| 9.80 | 1 | s | | H$_{20}$ |

(ii) Colorless amorphous solid (reprecipitated from (acetone-n-hexane)
(iii) Anal. for C$_{35}$H$_{60}$N$_2$O$_9$:

| | C (%) | H (%) | N (%) |
|---|---|---|---|
| Calculated: | 64.39 | 9.26 | 4.29 |
| Found: | 64.54 | 9.11 | 4.06 |

(iv) $[\alpha]_D^{23}$ + 22° (c 1.0, CHCl$_3$).

EXAMPLE 6

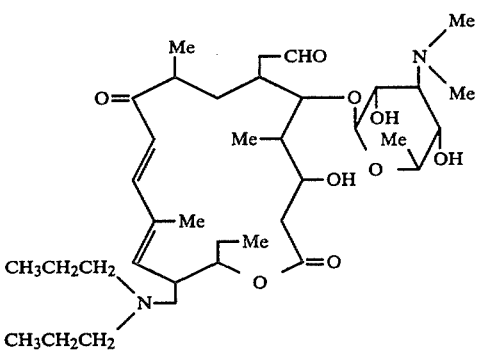

After dissolving 200 mg of 23-deoxy-23-iodomycaminosyl tylonolide diethyl acetal in 4 ml of anhydrous acetonitrile, 0.175 ml of di-n-propylamine was added to the solution and the reaction was performed for one day at 80° C. The reaction mixture was concentrated under reduced pressure to distill off acetonitrile, and after adding chloroform to the residue, the mixture was concentrated under reduced pressure. The residue was dissolved in 10 ml of chloroform, and the solution was washed once with 2 ml of saturated aqueous sodium hydrogencarbonate solution and then twice each time with 2 ml of saturated aqueous sodium sulfate solution, dried over anhydrous sodium sulfate and concentrated under reduced pressure. The residue was azeotropied three times with toluene, and charged to a column filled with 20 g of silica gel and a mixture of chloroform and methanol (50:1) using said mixture. The chromatography was performed using a mixture of chloroform and methanol (6:1) to provide 160.5 mg (yield 80%) of the crude product.

Then, 110 mg of the product thus obtained was chromatographied by silica gel column using a mixture of chloroform, methanol and conc. aqueous ammonia (15:1:0.1) to provide 76.7 mg (yield about 82%) of 23-deoxy-23-dipropylaminomycaminosyl tylonolide diethyl acetal.

After dissolving 51.0 mg of the product thus obtained in 1.0 ml of acetonitrile, 2.03 ml of 0.1N hydrochloric acid was added to the solution and the reaction was performed for 60 minutes. The reaction mixture was neutralized with 22.7 mg of sodium hydrogencarbonate and 1 ml of saturated aqueous sodium hydrogencarbonate solution, and the mixture was extracted three times with chloroform. The extracts were combined, washed twice with saturated aqueous sodium sulfate solution, dried over anhydrous sodium sulfate, and concentrated. The residue was chromatographied by silica gel column using a mixture of chloroform, methanol and conc. aqueous ammonia to provide 32.9 mg (yield 72%) of 23-deoxy-23-dipropylaminomycaminosyl tylonolide.

(i) NMR (CDCl$_3$):

| δ (ppm) | H number | Form | J (Hz) | |
|---|---|---|---|---|
| ~1.57 | | | | 23-N(CH$_2$CH$_2$CH$_3$)$_2$ |
| 2.33 | ~4 | m | | 23-N(CH$_2$CH$_2$CH$_3$)$_2$ |
| 2.54 | 6 | s | | 3'-NMe$_2$ |
| 4.28 | 1 | d$_{1',2'}$ | 7.5 | H$_{1'}$ |
| 4.77 | 1 | m | | H$_{15}$ |
| 9.80 | 1 | s | | H$_{20}$ |

(ii) Colorless amorphous solid (reprecipitated from acetone-n-hexane)
(iii) Anal. for C$_{37}$H$_{64}$N$_2$O$_9$:

| | C (%) | H (%) | N (%) |
|---|---|---|---|
| Calculated: | 65.27 | 9.47 | 4.11 |
| Found: | 65.58 | 9.52 | 3.97 |

(iv) $[\alpha]_D^{23}$ + 31° (c 1.0, CHCl$_3$)

EXAMPLE 7

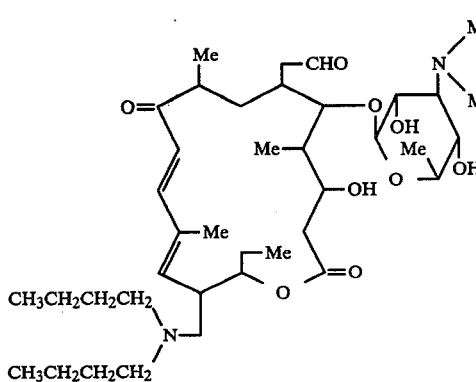

By following the same procedure as in Example 2 using 120.7 mg of 23-deoxy-23-iodomycaminosyl tylonolide diethylacetal and 0.132 ml of di-n-butylamine, 74.7 mg (yield 68.0%) of 23-deoxy-23-dibutylaminomycaminosyl tylonolide was obtained.

(i) NMR (CDCl$_3$):

| δ (ppm) | H number | Form | J (Hz) | |
|---|---|---|---|---|
| ~2.35 | ~4 | m | | 23-N(CH$_2$CH$_2$CH$_2$CH$_3$)$_2$ |
| 2.54 | 6 | s | | 3'-NMe$_2$ |
| 4.32 | 1 | d$_{1',2'}$ | 7.5 | H$_{1'}$ |
| 4.76 | 1 | m | | H$_{15}$ |
| 9.80 | 1 | s | | H$_{20}$ |

(ii) Colorless amorphous solid (reprecipitated from acetone-n-hexane)
(iii) Anal. for C$_{39}$H$_{68}$N$_2$O$_9$:

| | C (%) | H (%) | N (%) |
|---|---|---|---|
| Calculated: | 66.07 | 9.67 | 3.95 |
| Found: | 65.89 | 9.38 | 3.83 |

(iv) $[\alpha]_D^{22}$ + 28° (c 1.0, CHCl$_3$).

EXAMPLE 8

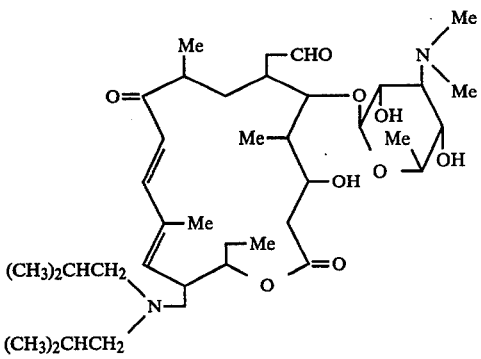

By following the same procedure as in Example 2 using 94.6 mg of 23-deoxy-23-iodomycaminosyl tylonolide diethylacetal and 0.105 ml of diisobutylamine, 63.2 mg (yield 73.6%) of 23-deoxy-23-diisobutylaminomycaminosyl tylonolide.

(i) NMR (CDCl$_3$):

| δ (ppm) | H number | Form | J (Hz) | |
|---|---|---|---|---|
| ~2.04 | ~4 | m | | 23-N[CH$_2$CH(CH$_3$)$_2$]$_2$ |
| 2.53 | 6 | s | | 3'-NMe$_2$ |
| 4.30 | 1 | d$_{1',2'}$ | 7.5 | H$_{1'}$ |
| 4.73 | 1 | m | | H$_{15}$ |
| 9.79 | 1 | s | | H$_{20}$ |

(ii) Colorless amorphous solid (reprecipitated from acetone-n-hexane)
(iii) Anal. for C$_{39}$H$_{68}$N$_2$O$_9$:

| | C (%) | H (%) | N (%) |
|---|---|---|---|
| Calculated: | 66.07 | 9.67 | 3.95 |
| Found: | 65.98 | 9.52 | 3.80 |

(iv) $[\alpha]_D^{21.5}$ + 49° (c 1.0, CHCl$_3$)

EXAMPLE 9

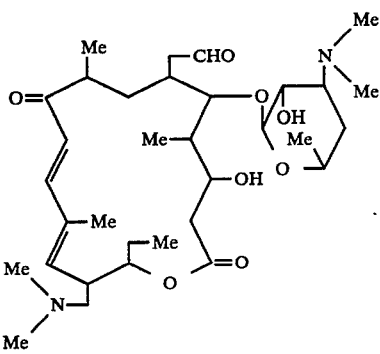

In 0.98 ml of anhydrous acetonitrile was dissolved 49.0 mg of 23,4'-dideoxy-23-iodomycaminosyl tylonolide diethylacetal and after adding thereto 0.1 ml of an about 5M dimethylamineacetonitrile solution, the reaction was performed for 30 minutes at 80° C. in closed state. Then, to the reaction mixture was added 0.1 ml of the dimethylamine-acetonitrile solution as described above and after performing the reaction for 30 minutes, the reaction mixture was concentrated. The residue was dissolved in 2.5 ml of chloroform and the solution was washed once with 1 ml of a saturated aqueous sodium hydrogen carbonate solution and then 1 ml of a saturated aqueous sodium sulfate solution and, after drying with anhydrous sodium sulfate, concentrated under reduced pressure.

The residue was dissolved in 0.98 ml of acetonitrile and after adding thereto 1.9 ml of 0.1N hydrochloric acid, the reaction was performed for 60 minutes at 20° C. To the reaction mixture was added 22 mg of sodium hydrogen carbonate and the product was extracted three times each time with 1 ml of chloroform. The chloroform layers were combined with each other and the mixture was washed once with 1 ml of a saturated aqueous sodium sulfate solution and after drying with anhydrous sodium sulfate, concentrated under reduced pressure. The residue was subjected to a chromatographic treatment by a column of 5 g of silica gel using a solvent system of chloroform-methanol-concentrated aqueous ammonia (18:1:0.1) to provide 31.0 mg (yield 80%) of 23,4'-dideoxy-23-dimethylaminomycaminosyl tylonolide.

| (i) | NMR (CDCl$_3$) | | | | |
|---|---|---|---|---|---|
| | δ (ppm) | H number | Form | J (Hz) | |
| | 2.22 | 6 | s | | 23-NMe$_2$ |
| | 2.31 | 6 | s | | 3'-NMe$_2$ |
| | 4.23 | 1 | d$_{1',2'}$ | 7.5 | H$_{1'}$ |
| | 4.78 | 1 | m | | H$_{15}$ |
| | 9.83 | 1 | s | | H$_{20}$ |
| (ii) | Colorless amorphous solid (reprecipitated from acetone-n-hexane) | | | | |
| (iii) | Anal. for C$_{31}$H$_{56}$N$_2$O$_9$: | | | | |
| | | C (%) | H (%) | N (%) | |
| | Calculated: | 65.10 | 9.27 | 4.60 | |
| | Found: | 66.21 | 9.16 | 4.37 | |
| (iv) | $[\alpha]_D^{23}$ + 23° (c 1.0, CHCl$_3$) | | | | |

EXAMPLE 10

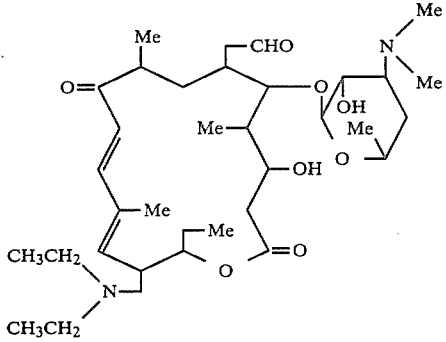

In 1.0 ml of anhydrous acetonitrile was dissolved 51.0 mg of 23,4'-dideoxy-23-iodomycaminosyl tylonolide diethylacetal and after adding thereto 24.3 mg of diethylamine, the reaction was performed for 3 hours at 80° C. under a closed state. Then, to the reaction mixture was further added 24.3 mg of diethylamine and after performing the reaction for 3 hours, the reaction mixture was concentrated. The residue was dissolved in 2.5 ml of chloroform and the solution was washed once with 1 ml of a saturated aqueous sodium hydrogen carbonate solution and then 1 ml of a saturated aqueous sodium sulfate solution and, after drying with anhydrous sodium sulfate, concentrated under reduced pressure.

The residue was dissolved in 1.0 ml of acetonitrile and after adding thereto 20 ml of 0.1N hydrochloric acid, the reaction was performed for 60 minutes at 20° C. To the reaction mixture was added 22.4 mg of sodium hydrogen carbonate and the product was extracted three times each time with 1 ml of chloroform. The chloroform layers were combined with each other and the mixture was washed once with 1 ml of a saturated aqueous sodium sulfate solution and then concentrated under reduced pressure. The residue was subjected to chromatographic treatment by a column of 5 g of silica gel using a solvent system of chloroform-methanol-concentrated aqueous ammonia (20:1:0.1) to provide 25.7 mg (yield 61%) of 23,4'-dideoxy-23-diethylaminomycaminosyl tylonolide.

| (i) | NMR (CDCl$_3$): | | | | |
|---|---|---|---|---|---|
| | δ (ppm) | H number | Form | J (Hz) | |
| | 2.31 | 6 | s | | 3'-NMe$_2$ |
| | ~2.53 | ~4 | | | 23-N(CH$_2$CH$_3$)$_2$ |
| | 4.25 | 1 | d$_{1',2'}$ | 7.5 | H$_{1'}$ |
| | 4.78 | 1 | m | | H$_{15}$ |
| | 9.83 | 1 | s | | H$_{20}$ |
| (ii) | Colorless amorphous solid (reprecipitated from acetone-n-hexane) | | | | |
| (iii) | Anal. for C$_{35}$H$_{60}$N$_2$O$_8$: | | | | |
| | | C (%) | H (%) | N (%) | |
| | Calculated: | 66.01 | 9.50 | 4.40 | |
| | Found: | 65.71 | 9.44 | 4.32 | |
| (iv) | $[\alpha]_D^{23}$ + 28° (c 1.0, CHCl$_3$). | | | | |

EXAMPLE 11

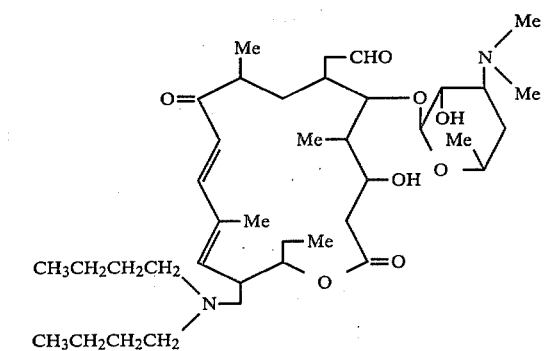

By following the same procedure as in Example 2 using 98.0 mg of 23,4'-dideoxy-23-iodomycaminosyl tylonolide diethylacetal and 82.6 mg of di-n-butylamine, 74.4 mg (yield 84%) of 23,4'-dideoxy-23-dibutylaminomycaminosyl tylonolide was obtained.

| (i) | NMR (CDCl$_3$): | | | | |
|---|---|---|---|---|---|
| | δ (ppm) | H number | Form | J (Hz) | |
| | 2.55 | 6 | s | | 3'-NMe$_2$ |
| | ~2.3 | ~4 | m | | 23-N(CH$_2$CH$_2$CH$_2$CH$_3$)$_2$ |
| | 4.26 | 1 | d$_{1',2'}$ | 7.5 | H$_{1'}$ |
| | 4.77 | 1 | m | | H$_{15}$ |
| | 9.88 | 1 | s | | H$_{20}$ |
| (ii) | Colorless amorphous solid (reprecipitated from acetone-n-hexane) | | | | |
| (iii) | Anal. for C$_{39}$H$_{68}$N$_2$O$_8$: | | | | |
| | | C (%) | H (%) | N (%) | |
| | Calculated: | 67.60 | 9.89 | 4.04 | |
| | Found: | 67.32 | 9.71 | 4.01 | |
| (iv) | $[\alpha]_D^{25}$ + 37° (c 1.0, CHCl$_3$). | | | | |

EXAMPLE 12

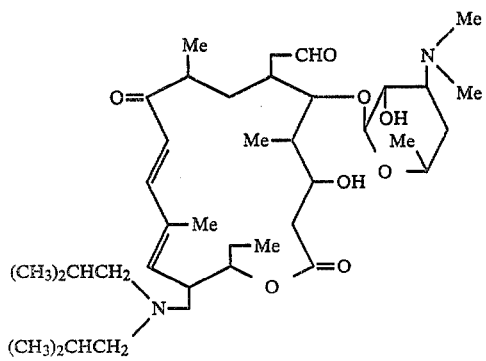

By following the same procedure as in Example 2 using 118 mg of 23,4'-dideoxy-23-iodomycaminosyl tylonolide diethylacetal and 99.1 mg of diisobutylamine, 75.0 mg (yield 71%) of 23,4'-dideoxy-23-diisobutylaminomycaminosyl tylonolide was obtained.

(i) NMR (CDCl$_3$):

| δ (ppm) | H number | Form | J (Hz) | |
|---|---|---|---|---|
| 2.32 | 6 | s | | 3'-NMe$_2$ |
| ~2.04 | ~4 | | | 23-[CH$_2$CH(CH$_3$)$_2$]$_2$ |
| 4.24 | 1 | d$_{1',2'}$ | 7.5 | H$_1$' |
| 4.78 | 1 | m | | H$_{15}$ |
| 9.83 | 1 | s | | H$_{20}$ |

(ii) Colorless amorphous solid (reprecipitated from acetone-n-hexane)
(iii) Anal. for C$_{39}$H$_{68}$N$_2$O$_8$:

|  | C (%) | H (%) | N (%) |
|---|---|---|---|
| Calculated: | 67.60 | 9.89 | 4.04 |
| Found: | 67.38 | 9.82 | 4.16 |

(iv) $[\alpha]_D^{25}$ + 55° (c 1.0, CHCl$_3$)

EXAMPLE 13

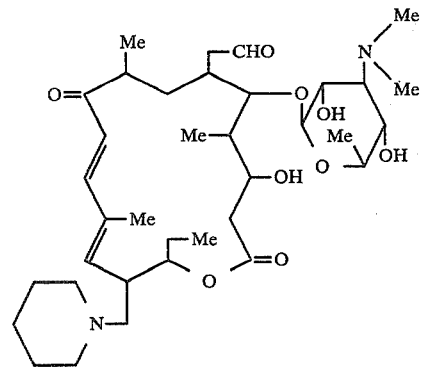

By following the same procedure as in Example 1(a) using 199.9 mg of 23-deoxy-23-iodomycaminosyl tylonolide diethylacetal and 0.13 ml of piperidine, 179.5 mg (yield 95%) of 23-deoxy-23-piperidinomycaminosyl tylonolide diethylacetal was obtained, and then by following the same procedure as in Example 1(b) using 91.9 mg of the product thus obtained, 76.1 mg (yield 92%) of 23-deoxy-23-piperidinomycaminosyl tylonolide was obtained.

(i) NMR (CDCl$_3$):

| δ (ppm) | H number | Form | J (Hz) | |
|---|---|---|---|---|
| ~1.58 | ~6 | m | | 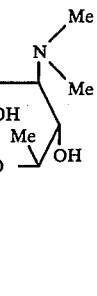 |
| ~2.37 | ~4 | m | | |
| 2.54 | 6 | s | | 3'-NMe$_2$ |
| 4.30 | 1 | d$_{1',2'}$ | 7.5 | H$_1$' |
| 4.78 | 1 | m | | H$_{15}$ |
| 9.80 | 1 | s | | H$_{20}$ |

(ii) Colorless amorphous solid (reprecipitated from acetone-n-hexane)
(iii) Anal. for C$_{36}$H$_{60}$N$_2$O$_9$:

|  | C (%) | H (%) | N (%) |
|---|---|---|---|
| Calculated: | 65.03 | 9.10 | 4.21 |
| Found: | 64.80 | 8.99 | 3.98 |

(iv) $[\alpha]_D^{23}$ + 28° (c 1.0, CHCl$_3$)

EXAMPLE 14

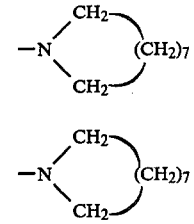

By following the same procedure as in Example 2 using 60.0 mg of 23-deoxy-23-iodomycaminosyl tylonolide diethylacetal and 48.4 mg of nonamethyleneimine, 50.3 mg (yield 91%) of 23-deoxy-23-nonamethyleneiminomycaminosyl tylonolide was obtained.

(i) NMR (CDCl$_3$):

| δ (ppm) | H number | Form | J (Hz) | |
|---|---|---|---|---|
| ~1.5 | ~14 | s | | 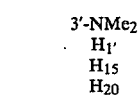 |
| ~2.5 | 4 | | | |
| 2.55 | 6 | s | | 3'-NMe$_2$ |
| 4.28 | 1 | d$_{1',2'}$ | 7.5 | H$_1$' |
| 4.78 | 1 | m | | H$_{15}$ |
| 9.80 | 1 | s | | H$_{20}$ |

(ii) Colorless amorphous solid (reprecipitated from

-continued acetone-n-hexane)
(iii) Anal. for $C_{40}H_{68}N_2O_9$:

| | C (%) | H (%) | N (%) |
|---|---|---|---|
| Calculated: | 66.64 | 9.51 | 3.89 |
| Found: | 66.82 | 9.63 | 3.61 |

(iv) $[\alpha]_D^{24} + 22°$ (c 1.0, CHCl$_3$)

EXAMPLE 15

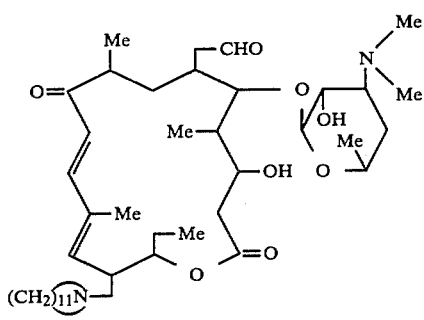

By following the same procedure as in Example 2 using 90.0 mg of 23-deoxy-23-iodomycaminosyl tylonolide diethylacetal and 97.2 mg of undecamethyleneimine, 71.5 mg (yield 83%) of 23-deoxy-23-undecamethyleneiminomycaminosyl tylonolide was obtained.

(i) NMR (CDCl$_3$):

| δ (ppm) | H number | Form | J (Hz) | |
|---|---|---|---|---|
| ~1.5 | 18 | s | | 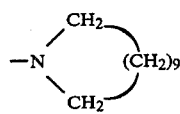 |
| 2.54 | 6 | s | | 3'-NMe$_2$ |
| ~2.5 | 4 | | | 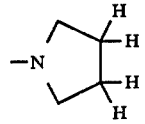 |
| 4.27 | 1 | d$_{1',2'}$ | 7.5 | H$_{1'}$ |
| 4.76 | 1 | m | | H$_{15}$ |
| 9.81 | 1 | s | | H$_{20}$ |

(ii) Colorless amorphous solid (reprecipitated from acetone-n-hexane)
(iii) Anal. for $C_{42}H_{72}N_2O_9$:

| | C (%) | H (%) | N (%) |
|---|---|---|---|
| Calculated: | 67.35 | 9.69 | 3.74 |
| Found: | 67.10 | 9.43 | 3.82 |

(iv) $[\alpha]_D^{24} + 20°$ (c 1.0, CHCl$_3$).

EXAMPLE 16

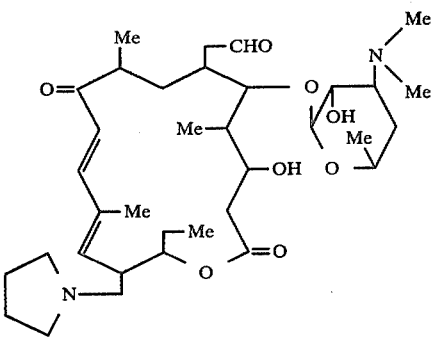

By following the same procedure as in Example 2 using 93.0 mg of 23,4'-dideoxy-23-iodomycaminosyl tylonolide diethylacetal and 43.3 mg of pyrrolidine, 69.6 mg (yield 90%) of 23,4'-dideoxy-23-pyrrolidinomycaminosyl tylonolide was obtained.

(i) NMR (CDCl$_3$):

| δ (ppm) | H number | Form | H (Hz) | |
|---|---|---|---|---|
| ~1.8 | ~4 | m | | 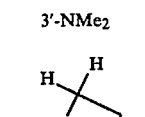 |
| 2.31 | 6 | s | | 3'-NMe$_2$ |
| 2.6 | 4 | m | | 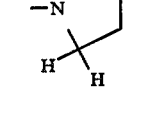 |
| 4.25 | 1 | d$_{1',2'}$ | 7.5 | H$_{1'}$ |
| 4.80 | 1 | m | | H$_{15}$ |
| 9.83 | 1 | s | | H$_{20}$ |

(ii) Anal. for $C_{35}H_{58}N_2O_8$:

| | C (%) | H (%) | N (%) |
|---|---|---|---|
| Calculated: | 66.42 | 9.33 | 4.34 |
| Found: | 66.22 | 9.21 | 4.41 |

(iii) $[\alpha]_D^{22} + 38°$ (c 0.5, CHCl$_3$).

EXAMPLE 17

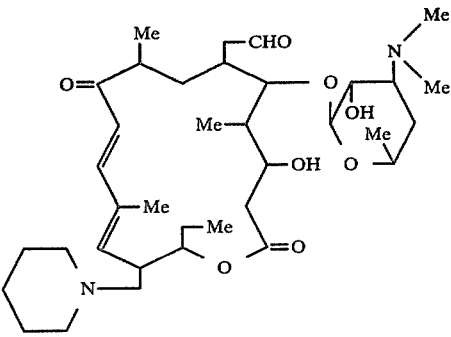

By following the same procedure as in Example 2 using 92.3 mg of 23,4'-dideoxy-23-iodomycaminosyl tylonolide diethylacetal and 51.4 mg of piperidine, 73.0 mg (yield 93%) of 23,4'-dideoxy-23-piperidinomycaminosyl tylonolide was obtained.

(i) NMR (CDCl₃):

| δ (ppm) | H number | Form | J (Hz) | |
|---|---|---|---|---|
| ~1.5 | 6 | m | | 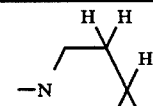 |
| 2.30 | 6 | s | | 3'-NMe₂ |
| ~2.4 | 4 | m | | 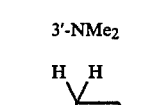 |
| 4.25 | 1 | d₁',₂' | 7.5 | H₁' |
| 4.78 | 1 | m | | H₁₅ |
| 9.83 | 1 | s | | H₂₀ |

(ii) Anal. for C₃₆H₆₀N₂O₈:

| | C (%) | H (%) | N (%) |
|---|---|---|---|
| Calculated: | 66.64 | 9.32 | 4.32 |
| Found: | 66.93 | 9.05 | 4.20 |

(iii) [α]_D²² + 36° (c 1.0, CHCl₃)

EXAMPLE 18

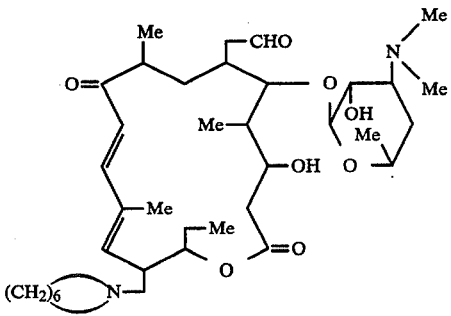

By following the same procedure as in Example 2 using 62.5 mg of 23,4'-dideoxy-23-iodomycaminosyl tylonolide and 40.5 mg of hexamethyleneimine, 52.4 mg (yield 97%) of 23,4'-dideoxy-23-hexamethyleneiminomycaminosyl tylonolide was obtained.

(Recrystallized from acetone-n-hexane, recrystallization yield 80%)

(i) NMR (CDCl₃):

| δ(ppm) | H number | Form | J(Hz) | |
|---|---|---|---|---|
| 1.57 | ~8 | broad s | | 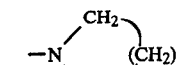 |
| 2.31 | 6 | s | | 3'-NMe₂ |
| ~2.63 | 4 | m | | 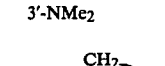 |
| 4.25 | 1 | d₁',₂' | 7.5 | H₁' |
| 4.80 | 1 | m | | H₁₅ |
| 9.83 | 1 | s | | H₂₀ |

(ii) Colorless platy crystal (recrystallized from acetone-n-hexane)
(iii) M.p. 195–198° C.
(iv) Anal. for C₃₇H₆₂N₂O₈:

| | C (%) | H (%) | N (%) |
|---|---|---|---|
| Calculated: | 67.03 | 9.43 | 4.23 |
| Found: | 66.91 | 9.21 | 4.03 |

(iv) [α]_D²³ + 36° (c 1.0, CHCl₃).

EXAMPLE 19

By following the same procedure as in Example 2 using 70.0 mg of 23,4'-dideoxy-23-iodomycaminosyl tylonolide diethylacetal and 51.8 mg of heptamethyleneimine, 58.5 mg (yield 95%) of 23,4'-dideoxy-23-heptamethyleneiminomycaminosyl tylonolide was obtained.

(i) NMR (CDCl₃):

| δ(ppm) | H number | Form | J(Hz) | |
|---|---|---|---|---|
| 1.52 | ~8 | broad s | | 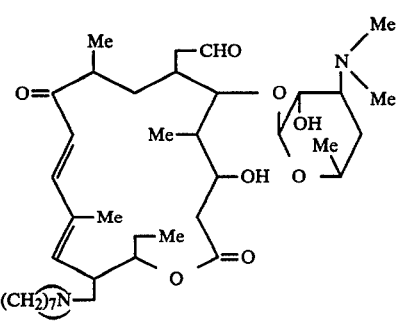 |
| 2.31 | 6 | s | | 3'-NMe₂ |
| ~2.53 | 4 | m | | |
| 4.23 | 1 | d₁',₂' | 7.5 | H₁' |
| 4.77 | 1 | m | | H₁₅ |
| 9.83 | 1 | s | | H₂₀ |

(ii) Colorless amorphous solid (reprecipitated from acetone-n-hexane)
(iii) Anal. for C₃₈H₆₄N₂O₈:

| | C (%) | H (%) | N (%) |
|---|---|---|---|
| Calculated: | 67.42 | 9.53 | 4.14 |
| Found: | 67.25 | 9.26 | 4.12 |

(iv) [α]_D²³ + 32° (c 1.0, CHCl₃)

EXAMPLE 20

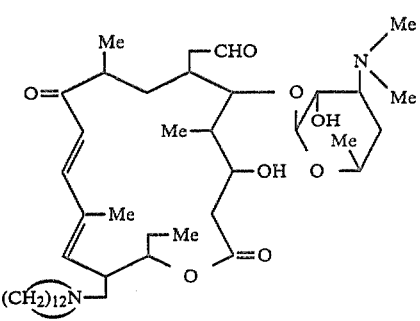

By following the same procedure as in Example 2 using 64.0 mg of 23,4'-dideoxy-23-iodomycaminosyl tylonolide diethylacetal and 76.8 mg of dodecamethyleneimine, 50.2 mg (yield 80%) of 23,4'-dideoxy-23-dodecamethyleneiminomycaminosyl tylonolide was obtained.

(i) NMR (CDCl₃):

| δ(ppm) | H number | Form | J(Hz) | |
|---|---|---|---|---|
| ~1.3 | 20 | m | | $-N\begin{pmatrix}CH_2\\CH_2\end{pmatrix}(CH_2)_{10}$ |
| 2.31 | 6 | s | | 3'-NMe₂ |
| ~2.5 | 4 | m | | $-N\begin{pmatrix}CH_2\\CH_2\end{pmatrix}(CH_2)_{10}$ |
| 3.23 | 1 | $d_{1',2'}$ | 7.5 | $H_{1'}$ |
| 4.78 | 1 | m | | $H_{15}$ |
| 9.83 | 1 | s | | $H_{20}$ |

(iii) Colorless amorphous solid (reprecipitated from acetone-n-hexane)
(iii) Anal. for $C_{43}H_{74}N_2O_8$:

| | C (%) | H (%) | N (%) |
|---|---|---|---|
| Calculated: | 69.13 | 9.98 | 3.75 |
| Found: | 68.92 | 9.76 | 3.62 |

(iv) $[\alpha]_D^{24} + 66°$ (c 1.0, CHCl₃).

EXAMPLE 21

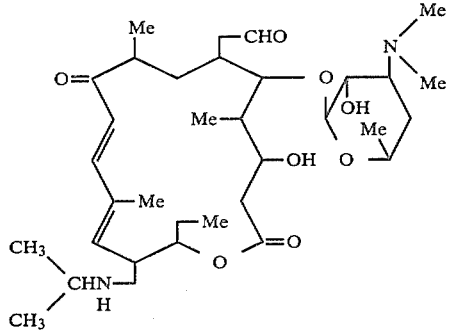

By following the same procedure as in Example 2 using 970 mg of 23,4'-dideoxy-23-iodomycaminosyl tylonolide diethylacetal and 375 mg of isopropylamine, 280 mg (yield 35%) of 23,4'-dideoxy-23-isopropylaminomycaminosyl tylonolide was obtained.

(i) NMR (CDCl₃):

| δ (ppm) | H number | Form | J (Hz) | |
|---|---|---|---|---|
| 1.02 | 6 | d | | 23-NH—CH(CH₃)₂ |
| 1.81 | 1 | s | | Me(22) |
| 2.28 | 6 | s | | NMe₂ |
| 4.22 | 1 | $d_{1',2'}$ | 7.5 | $H_{1'}$ |
| 4.82 | 1 | m | | $H_{15}$ |
| 5.68 | 1 | $d_{13,14}$ | 10 | $H_{13}$ |
| 6.32 | 1 | $d_{10,11}$ | 16 | $H_{10}$ |
| 7.34 | 1 | d | | $H_{11}$ |
| 9.72 | 1 | s | | $H_{20}$ |

(ii) Anal. for $C_{34}H_{58}N_2O_8$:

| | C (%) | H (%) | N (%) |
|---|---|---|---|
| Calculated: | 65.57 | 9.39 | 4.50 |
| Found: | 65.64 | 9.52 | 4.27 |

(iii) Mass (m/z):
622(M⁺), 551, 494, 448, 400, 281, 174, 158, 98, 72.
(iv) IR (KBr) (cm⁻¹):
2970, 2940, 1720, 1680, 1595.

EXAMPLE 22

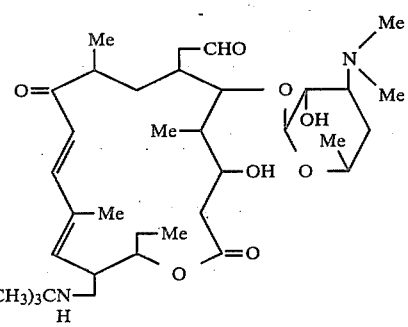

By following the same procedure as in Example 2 using 2 g of 23,4'-dideoxy-23-iodomycaninosyl tylonolide diethylacetal and 953 mg of t-butylamine, 1.12 g (yield 67%) of 23,4'-dideoxy-23-(t-butylamino)-mycaminosyl tylonolide was obtained.

(i) NMR (CDCl₃):

| δ (ppm) | H number | Form | J (Hz) | |
|---|---|---|---|---|
| 1.05 | 9 | s | | NHC(CH₃)₃ |
| 1.80 | 3 | s | | Me(22) |
| 2.24 | 6 | s | | NMe₂ |
| 4.20 | 1 | $d_{1',2'}$ | 7.5 | $H_{1'}$ |
| 4.82 | 1 | m | | $H_{15}$ |
| 5.64 | 1 | $d_{13,14}$ | 10 | $H_{13}$ |
| 6.31 | 1 | $d_{10,11}$ | 16 | $H_{10}$ |
| 7.34 | 1 | d | | $H_{11}$ |
| 9.72 | 1 | s | | $H_{20}$ |

(ii) Anal. for $C_{35}H_{60}N_2O_8$:

| | C (%) | H (%) | N (%) |
|---|---|---|---|
| Calculated: | 66.01 | 9.50 | 4.40 |
| Found: | 65.82 | 9.41 | 4.65 |

(iii) Mass (m/z):
636(M⁺), 551, 507, 462, 174, 158, 98, 86
(iv) IR (KBr) (cm⁻¹):
2970, 2940, 1720, 1680, and 1596.

EXAMPLE 23

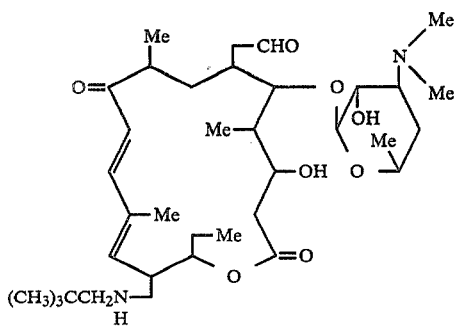

By following the same procedure as in Example 2 using 1.28 g of 23,4'-dideoxy-23-iodomycaminosyl tylonolide diethylacetal and 730 mg of neopentylamine, 480 mg (yield 44%) of 23,4'-dideoxy-23-neopentylaminocaminosyl tylonolide was obtained.

(i) NMR (CDCl$_3$):

| δ (ppm) | H number | Form | J (Hz) | |
|---|---|---|---|---|
| 0.89 | 9 | s | | NH—CH$_2$C(CH$_3$)$_3$ |
| 1.83 | 3 | s | | Me(22) |
| ~2.3 | 8 | | | NH—CH$_2$C(CH$_3$)$_2$, NMe$_2$ |
| 4.21 | 1 | d$_{1',2'}$ | 7.5 | H$_{1'}$ |
| 4.84 | 1 | m | | H$_{15}$ |
| 5.71 | 1 | d$_{13,14}$ | 10 | H$_{13}$ |
| 6.30 | 1 | d$_{10,11}$ | 16 | H$_{10}$ |
| 7.31 | 1 | d | | H$_{11}$ |
| 9.71 | 1 | s | | H$_{20}$ |

(ii) Anal for C$_{36}$H$_{62}$N$_2$O$_8$:

| | C (%) | H (%) | N (%) |
|---|---|---|---|
| Calculated: | 66.43 | 9.60 | 4.30 |
| Found: | 66.15 | 9.32 | 4.54 |

(iii) Mass (m/z):
650(M$^+$), 594, 476, 377, 174, 158, 100, and 71
(iv) IR (KBr) (cm$^{-1}$):
2970, 2940, 1720, 1680, and 1595.

EXAMPLE 24

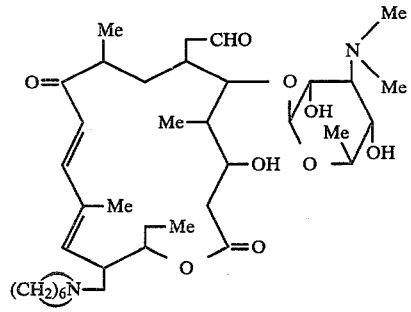

By following the same procedure as in Example 2 using 190 mg of 23-deoxy-23-iodomycaminosyl tylonolide diethylacetal and 120 mg of hexamethyleneimine, 128 mg (yield 78%) of 23-deoxy-23-hexamethyleneiminomycaminosyl tylonolide was obtained.

(i) NMR (CDCl$_3$):

| δ(ppm) | H number | Form | J(Hz) | |
|---|---|---|---|---|
| 1.57 | 8 | broad s | | (azepane ring) |
| 1.83 | 3 | s | | H$_{22}$ |
| 2.53 | 6 | s | | 3'-NMe$_2$ |
| 4.25 | 1 | d$_{1',2'}$ | 7.5 | H$_{1'}$ |
| 4.68 | 1 | m | | H$_{15}$ |
| 5.78 | 1 | d$_{13,14}$ | 10 | H$_{13}$ |
| 6.25 | 1 | d$_{10,11}$ | 16 | H$_{10}$ |
| 7.34 | 1 | d | 16 | H$_{11}$ |
| 9.72 | 1 | d | | H$_{20}$ |

(ii) Colorless amorphous solid
(iii) IR (KBr) (cm$^{-1}$):

| 2970 | —CH$_3$ |
|---|---|
| 2440 | —CH$_2$— |
| 1720 | —COO—, —CHO |
| 1680 | \>C=O |
| 1595 | —C=C—C=C— |

(iv) Mass (m/z):
678(M$^+$), 579, 331, 174, 112, 87
(v) [α]$_D^{22}$ + 31° (c 1.0, CHCl$_3$).

EXAMPLE 25

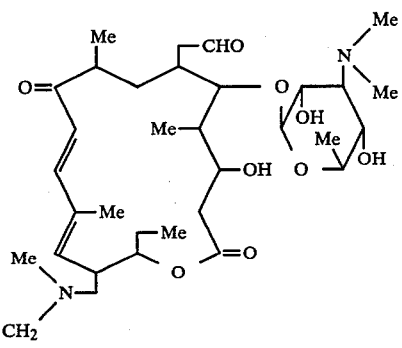

By following the same procedure as in Example 2 using 60.0 mg of 23-deoxy-23-iodomycaminosyl tylonolide diethylacetal and 46.5 mg of N-methylbenzylamine, 44.7 mg (yield 83%) of 23-deoxy-23-(N-methylbenzylamino)mycaminosyl tylonolide was obtained.

(i) NMR (CDCl$_3$):

| δ(ppm) | H number | Form | J(Hz) | |
|---|---|---|---|---|
| 1.84 | 3 | s | | H$_{22}$(12-CH$_3$) |
| 2.20 | 3 | s | | 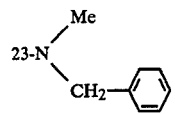 |
| 2.53 | 6 | s | | 3'-NMe$_2$ |

-continued

| | | | | |
|---|---|---|---|---|
| ~3.5 | 2 | | | 23-N(Me)(CH2-Ph) |
| 4.28 | 1 | d1',2' | 7.5 | H1' |
| 4.78 | 1 | m | | H15 |
| 5.77 | 1 | d13,14 | 10.0 | H13 |
| 6.31 | 1 | d10,11 | 16.0 | H10 |
| 7.36 | 5 | s | | 23-N(Me)(CH2-Ph) |
| 7.43 | 1 | d11,10 | 16.0 | H11 |
| 9.80 | 1 | s | | H20 |

(ii) IR (KBr) (cm⁻¹):
  2975 —CH₃
  2950 —CH₂—
  1730 —COO, —CHO
  1680 \C=O/
  1595 —C=C—C=C—

(iii) Colorless amorphous solid (reprecipitated from acetone-n-hexane)

(iv) Anal. for $C_{39}H_{60}N_2O_9$:

| | C (%) | H (%) | N (%) |
|---|---|---|---|
| Calculated: | 66.83 | 8.63 | 4.00 |
| Found: | 68.55 | 8.61 | 3.84 |

(v) $[\alpha]_D^{25}$ − 4° (c 1.0, CHCl₃)
(vi) UV $\lambda_{max}^{MeOH}$ 286 nm (ε = 25,000)
(vii) Rf 0.45 Wako gel B-5 (trade name, made by Wako Pure Chemical Industries, Ltd.) chloroform-methanol (6:1)

EXAMPLE 26

By following the same procedure as in Example 2 using 63.5 mg of 23-deoxy-23-iodomycaminosyl tylonolide diethylacetal and 62.9 mg of N-methylphenethylamine, 36.5 mg (yield 63%) of 23-deoxy-23-(N-methylphenethylamino)mycaminosyl tylonolide was obtained.

(i) NMR (CDCl₃):

| δ (ppm) | H number | Form | J (Hz) | |
|---|---|---|---|---|
| 1.82 | 3 | s | | H22(12-CH3) |

-continued

| | | | | |
|---|---|---|---|---|
| 2.28 | 3 | s | | 23-N(Me)(CH2CH2-Ph) |
| 2.55 | 6 | s | | 3'-NMe2 |
| 4.30 | 1 | d1',2' | 7.5 | H1' |
| 4.82 | 1 | m | | H15 |
| 5.77 | 1 | d13,14 | 10.0 | H13 |
| 6.28 | 1 | d10,11 | 16.0 | H10 |
| 7.30 } dupd.* | ~5 | m | | 23-N(Me)(CH2CH2-Ph) |
| 7.40 } | ~1 | d11,10 | 16.0 | H11 |
| 9.82 | 1 | s | | H20 |

(ii) IR (KBr) (cm⁻¹):
  2980 —CH₃
  2950 —CH₂—
  1730 —COO—, —CHO
  1680 \C=O/
  1595 —C=C—C=C—

(iii) Colorless amorphous solid
(iv) Anal. for $C_{40}H_{62}N_2O_9$:

| | C (%) | H (%) | N (%) |
|---|---|---|---|
| Calculated: | 67.20 | 8.74 | 3.92 |
| Found: | 66.98 | 8.57 | 3.71 |

(v) $[\alpha]_D^{25}$ + 30° (c 1.0, CHCl₃)
(vi) UV $\lambda_{max}^{MeOH}$ (ε = 24,000)
(vii) Rf 0.56 Wako gel B-5 chloroform-methanol (6:1)

(dupd*: duplicated)

EXAMPLE 27

By following the same procedure as in Example 2 using 60.0 mg of 23-deoxy-23-iodomycaminosyl tylonolide diethylacetal and 43.4 mg of N-methylcyclohexylamine, 45.7 mg (yield 86%) of 23-deoxy-23-(N-methylcyclohexylamino)mycaminosyl tylonolide was obtained.

(i) NMR (CDCl₃):

| δ (ppm) | H number | Form | J (Hz) | |
|---|---|---|---|---|
| 1.83 | 3 | s | | H₂₂(12-Me) |
| 2.21 | 3 | s | | 23-N(cyclohexyl)Me |
| 2.52 | 6 | s | | 3'-NMe₂ |
| 3.50 | 1 | dd$_{2',3'}^{2',1'}$ | 7.5, 10.0 | H₂' |
| 4.28 | 1 | d₁',₂' | 7.5 | H₁' |
| 4.77 | 1 | m | | H₁₅ |
| 5.77 | 1 | d₁₃,₁₄ | 10.0 | H₁₃ |
| 6.27 | 1 | d₁₀,₁₁ | 16.0 | H₁₀ |
| 7.40 | 1 | d₁₁,₁₀ | 16.0 | H₁₁ |
| 9.80 | 1 | s | | H₂₀ |

(ii) IR (KBr) (cm⁻¹):

| 2970 | —CH₃ |
|---|---|
| 2940 | —CH₂— |
| 1720 | —COO—, —CHO |
| 1680 | \C=O/ |
| 1595 | —C=C—C= |

(iii) Colorless amorphous solid (acetone-n-hexane)
(iv) Anal. for C₃₈H₆₅N₂O₉:

| | C (%) | H (%) | N (%) |
|---|---|---|---|
| Calculated: | 65.77 | 9.44 | 4.04 |
| Found: | 65.40 | 9.09 | 3.61 |

(v) $[\alpha]_D^{25}$ + 20° (c 1.0, CHCl₃)

(vi) UV $\lambda_{max}^{MeOH}$ 284.5 nm (ε = 25,000)

(vii) Rf 0.39 Wako gel B-5
chloroform-methanol (6:1).

EXAMPLE 28

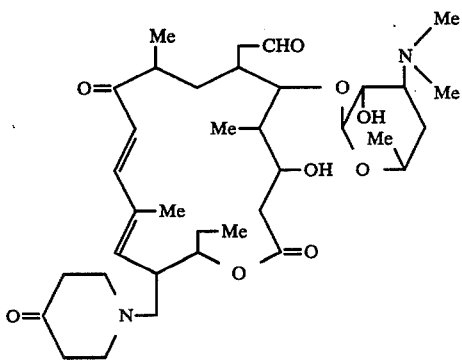

By following the same procedure as in Example 2 using 74.5 mg of 23,4'-dideoxy-23-iodomycaminosyl tylonolide diethylacetal and 70.6 mg of 4-piperidone dimethylketal, 49.1 mg (yield 76%) of 23,4'-dideoxy-23-(4-pipridone)mycaminosyl tylonolide was obtained. (Recrystallized from chloroform-n-hexane).

(i) NMR (CDCl₃):

| δ (ppm) | H number | Form | J (Hz) | |
|---|---|---|---|---|

-continued

| 1.85 | 3 | s | | H₂₂ |
|---|---|---|---|---|
| 2.30 | 6 | s | | 3'-NMe |
| H₂.₆₀ | ~8 | m | | 23-N(piperidone) |
| 4.25 | 1 | d₁',₂' | 7.5 | H₁' |
| 4.81 | 1 | m | | H₁₅ |
| 5.83 | 1 | d₁₃,₁₄ | 10.0 | H₁₃ |
| 6.35 | 1 | d₁₀,₁₁ | 16.0 | H₁₀ |
| 7.43 | 1 | d₁₁,₁₀ | 16.0 | H₁₁ |
| 9.83 | 1 | s | | H₂₀ |

(ii) IR (KBr) (cm⁻¹):

| 2970 | —CH₃ |
|---|---|
| 2940 | —CH₂— |
| 1740 | —N(piperidone)=O, —COO— |
| 1720 | —CHO |
| 1680 | \C=O/ |
| 1595 | —C=C—C=C— |

(iii) Colorless acicular crystal (recrystallized from chloroform-hexane)
(iv) m.p. 120–123° C.
(v) Anal. for C₃₆H₅₈N₂O₉·CHCl₃·H₂O:

| | C (%) | H (%) | N (%) | Cl (%) |
|---|---|---|---|---|
| Calculated: | 55.39 | 7.92 | 3.49 | 13.26 |
| Found: | 55.47 | 7.96 | 3.58 | 14.26 |

(vi) $[\alpha]_D^{23}$ + 39° (c 1.0, CHCl₃)

(vii) UV $\lambda_{max}^{MeOH}$ 284.5 nm (ε = 22,000)

(viii) Rf 0.33 Wako gel B-5
Chloroform-methanol-concentrated aqueous ammonia (18:1:0.1)

EXAMPLE 29

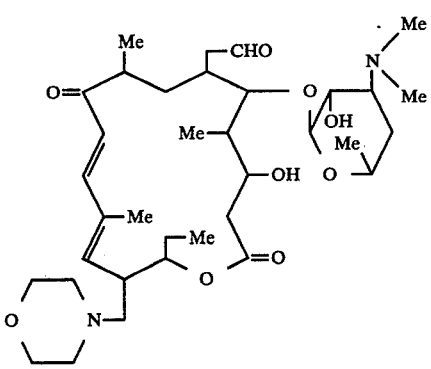

By following the same procedure as in Example 2 using 69.6 mg of 23,4'-dideoxy-23-iodomycaminosyl tylonolide diethylacetal and 0.039 ml of morpholine, 512 mg (yield 87%) of 23,4'-dideoxy-23-morpholinomycaminosyl tylonolide was obtained.

(i) NMR (CDCl₃):

| δ (ppm) | H number | Form | J (Hz) | |
|---|---|---|---|---|
| 2.31 | 6 | s | | 3'-NMe₂ |
| ~2.43 | ~4 | m | | 23-N(CH₂CH₂)₂O |
| 3.67 | 4 | m | | 23-N(CH₂CH₂)₂O |
| 4.28 | 1 | d₁',₂' | 7.5 | H₁' |
| 4.82 | 1 | m | | H₁₅ |
| 9.83 | 1 | s | | H₂₀ |

(ii) Anal. for $C_{35}H_{58}N_2O_9$:

| | C (%) | H (%) | N (%) |
|---|---|---|---|
| Calculated: | 64.59 | 8.98 | 4.30 |
| Found: | 64.33 | 8.86 | 4.07 |

(iii) $[\alpha]_D^{22}$ + 32° (c 1.0, CHCl₃)

EXAMPLE 30

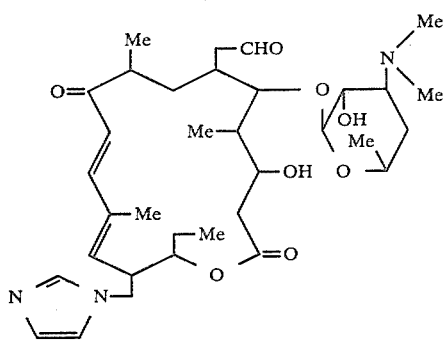

By following the same procedure as in Example 2 using 62.5 mg of 23,4'-dideoxy-4'-iodomycaminosyl tylonolide diethylacetal and 27.8 mg of imidazole, 24.5 mg (yield 48%) of 23,4'-dideoxy-23-(imidazol-1-yl)mycaminosyl tylonolide was obtained.

(i) NMR (CDCl₃):

| δ (ppm) | H number | Form | J (Hz) | |
|---|---|---|---|---|
| 2.30 | 6 | s | 7.5 | 3'-NMe₂ |
| 4.23 | 1 | d₁',₂' | 7.5 | H₁' |
| 4.92 | 1 | m | | H₁₅ |
| 6.90 | 1 | | | imidazole |
| 7.07 | 1 | | | |
| 7.48 | 1 | | | |
| 9.82 | 1 | s | | H₂₀ |

(ii) Anal. for $C_{34}H_{53}N_3O_8$:

| | C (%) | H (%) | N (%) |
|---|---|---|---|

-continued

| | | | |
|---|---|---|---|
| Calculated: | 64.64 | 8.46 | 6.65 |
| Found: | 64.76 | 8.54 | 6.55 |

(iii) $[\alpha]_D^{22}$ + 88° (c 1.0, CHCl₃)

EXAMPLE 31

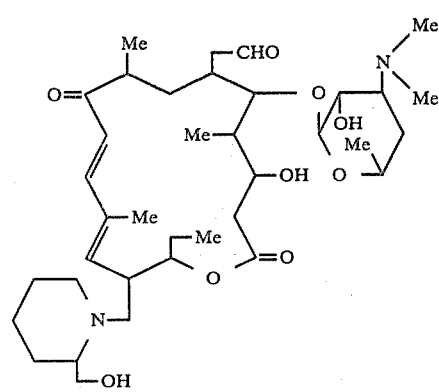

By following the same procedure as in Example 2 using 50.0 mg of 23,4'-dideoxy-23-iodomycaminosyl tylonolide diethylacetal and 37.6 mg of 2-(hydroxymethyl)piperidine, 27.9 mg (yield 65%) of 23,4'-dideoxy-23-[2-(hydroxymethyl)piperidino]mycaminosyl tylonolide was obtained.

(i) NMR (CDCl₃):

| δ (ppm) | H number | Form | J (Hz) | |
|---|---|---|---|---|
| 1.83 | 3 | s | | H₂₂ |
| 2.31 | 6 | s | | 3'-NMe₂ |
| 4.25 | 1 | d₁',₂' | 7.5 | H₁' |
| 4.80 | 1 | | | H₁₅ |
| 5.82 | 1 | d₁₃,₁₄ | 10.0 | H₁₃ |
| 6.37 | 1 | d₁₀,₁₁ | 16.0 | H₁₀ |
| 7.47 | 1 | d₁₁,₁₀ | 16.0 | H₁₁ |
| 9.82 | 1 | s | | H₂₀ |

(ii) IR (KBr) (cm⁻¹):

| | |
|---|---|
| 2940 | —CH₂— |
| 1720 | —COO—, —CHO |
| 1680 | >C=O |
| 1590 | —C=C—C=C— |

(iii) Colorless amorphous solid (reprecipitated from acetone-n-hexane)

(iv) Anal. for $C_{36}H_{62}N_2O_9$:

| | C (%) | H (%) | N (%) |
|---|---|---|---|
| Calculated: | 64.84 | 9.37 | 4.20 |
| Found: | 64.62 | 9.08 | 3.92 |

(v) $[\alpha]_D^{23}$ + 40° (c 1.0, CHCl₃)

(vi) UV: $\lambda_{max}^{MeOH}$ 285 nm ($\epsilon$ = 26,000)

(vii) Rf 0.22 Wako gel B-5 chloroform-methanol (10:1)

EXAMPLE 32

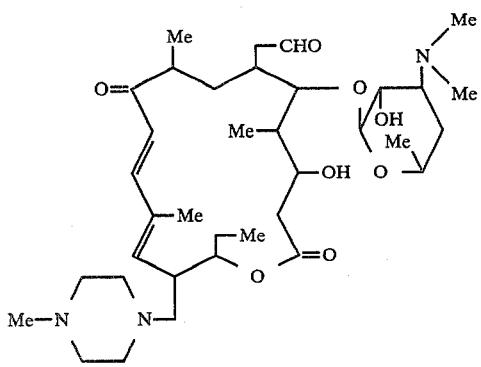

By following the same procedure as in Example 2 using 66.0 mg of 23,4'-dideoxy-23-iodomycaminosyl tylonolide diethylacetal and 0.048 ml of N-methylpiperazine, 44.6 mg (yield 76%) of 23,4'-dideoxy-23-(4-methylpiperazin-1-yl)mycaminosyl tylonolide was obtained.

(i) NMR (CDCl$_3$):

| δ (ppm) | H number | Form | J (Hz) | |
|---|---|---|---|---|
| 2.30 | 6 | s | | 3'—NMe$_2$ |
| | 3 | s | | Me—N‾‾N— |
| ~2.4 | 8 | m | | Me—N‾‾N— |
| 4.22 | 1 | d$_{1',2'}$ | 7.5 | H$_{1'}$ |
| 4.77 | 1 | m | | H$_{15}$ |
| 9.82 | 1 | s | | H$_{20}$ |

(ii) Anal. for C$_{36}$H$_{61}$N$_3$O$_8$:

| | C (%) | H (%) | N (%) |
|---|---|---|---|
| Calculated: | 65.13 | 9.26 | 6.33 |
| Found: | 65.35 | 9.04 | 6.11 |

(iii) $[\alpha]_D^{22}$ + 42° (c 0.5, CHCl$_3$).

EXAMPLE 33

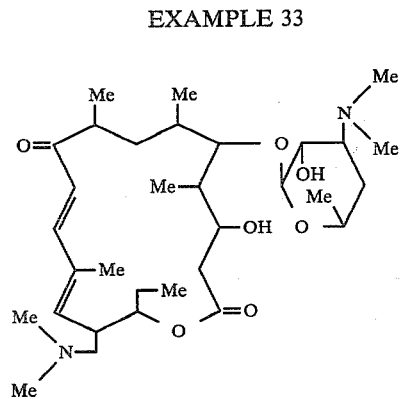

In 1.3 ml of anhydrous acetonitrile was dissolved 63.6 mg of 19-decarbonyl-22,4'-dideoxy-22-iodomycaminosyl tylonolide and then 0.24 ml of an about 4M dimethylamine-acetonitrile solution was added to the solution. After sealing the vessel and heating the mixture at 80° C. for 30 minutes, 0.24 ml of the aforesaid solution was further added thereto and the mixture was heated for 30 minutes. After distilling off the solvent under reduced pressure, the residue thus formed was dissolved in chloroform and the chloroform solution was washed with a saturated aqueous sodium hydrogen carbonate solution and then a saturated aqueous sodium sulfate solution and after drying the solution with anhydrous sodium sulfate, the solvent was distilled off. The residue was purified by a silica gel column using a solvent system of chloroform-methanol-28% aqueous ammonia (25:1:0.1) to provide 47.8 mg (yield 86%) of 19-decarbonyl-22,4'-dideoxy-22-dimethylaminomycaminosyl tylonolide was obtained.

(i) NMR (CDCl$_3$):

| δ (ppm) | H number | Form | J (Hz) | |
|---|---|---|---|---|
| 1.83 | 3 | s | | H$_{21}$(12-CH$_3$) |
| 2.21 | 6 | s | | 22-NMe$_2$ |
| 2.30 | 6 | s | | 3'-NMe$_2$ |
| 4.27 | 1 | d$_{1',2'}$ | 7.5 | H$_{1'}$ |
| 4.77 | 1 | m | | H$_{15}$ |
| 6.33 | 1 | d$_{10,11}$ | 16.0 | H$_{10}$ |
| 7.39 | 1 | d$_{11,10}$ | 16.0 | H$_{11}$ |

(ii) IR (KBr) (cm$^{-1}$):

| | |
|---|---|
| 2980 | —CH$_3$ |
| 2950 | —CH$_2$— |
| 1730 | —COO— |
| 1680 | \C=O / |
| 1595 | —C=C—C=C— |

(iii) Colorless amorphous solid (reprecipitated from acetone-n-hexane)

(iv) Anal. for C$_{32}$H$_{56}$N$_2$O$_7$:

| | C (%) | H (%) | N (%) |
|---|---|---|---|
| Calculated: | 66.18 | 9.72 | 4.82 |
| Found: | 65.94 | 9.43 | 4.60 |

(v) $[\alpha]_D^{25}$ + 74° (c 1.0, CHCl$_3$)

(vi) UV: $\lambda_{max}^{MeOH}$ 283 nm (ε = 22,000)

EXAMPLE 34

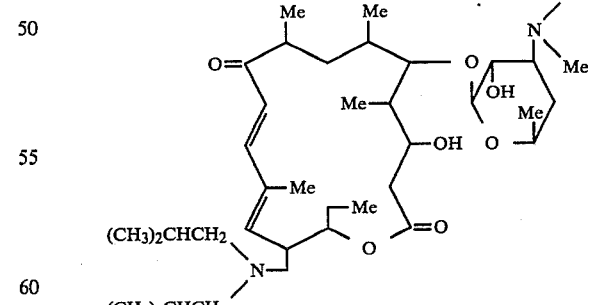

In 1.6 ml of anhydrous acetonitrile was dissolved 78.5 mg of 19-decarbonyl-22,4'-dideoxy-22-iodomycaminosyl tylonolide and after adding thereto 76 mg of diisobutylamine, the mixture was heated at 80° C. for 2 days. After distilling off the solvent under reduced pressure, the residue was dissolved in 4 ml of chloroform and the chloroform solution was washed with 2 ml of a saturated aqueous sodium hydrogen carbonate solution and then water and after drying with anhydrous sodium sulfate, the solvent was distilled off. Then, the residue was purified by a silica gel column using a solvent system of chloroform-methanol-28% aqueous ammonia (25:1:0.1) to provide 59.5 mg (yield 76%) of 19-decarbonyl-22,4'-dideoxy-22-diisobutylaminomycaminosyl tylonolide was obtained.

(i) NMR (CDCl₃):

| δ (ppm) | H number | Form | J (Hz) | |
|---|---|---|---|---|
| about 0.8 | about 12 | d | | —N[CH₂CH(CH₃)₂]₂ |
| 1.83 | 3 | s | | Me(21) |
| 2.30 | 6 | s | | 3'-NMe₂ |
| 4.28 | 1 | d₁',₂' | 7.5 | H₁' |
| 4.72 | 1 | m | | H₁₅ |
| 6.33 | 1 | d₁₀,₁₁ | 16 | H₁₀ |
| 7.40 | 1 | d₁₁,₁₀ | 16 | H₁₁ |

(ii) IR (KBr) (cm⁻¹):

| | | |
|---|---|---|
| 2980 | | —CH₃ |
| 2950 | | —CH₂— |
| 1730 | | —COO— |
| 1680 | |  |
| 1595 | | —C=C—C=C— |

(iii) Anal. for C₃₆H₆₈N₂O₇:

| | C (%) | H (%) | N (%) |
|---|---|---|---|
| Calculated: | 68.64 | 10.31 | 4.21 |
| Found: | 68.52 | 10.21 | 4.33 |

(iv) $[\alpha]_D^{23}$ + 55° (c 1.0, CHCl₃)

(v) UV $\lambda_{max}^{MeOH}$ 285 nm (ε = 23,000)

EXAMPLE 35

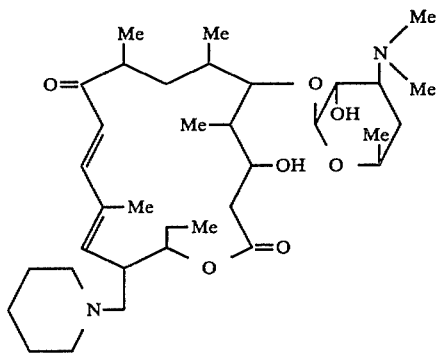

By following the same procedure as in Example 34 using 82.5 mg of 19-decarbonyl-22,4'-dideoxy-22-iodomycaminosyl tylonolide and 52.3 mg of piperidine, 70.7 mg (yield 92%) of 19-decarbonyl-22,4'-dideoxy-22-piperidinomycaminosyl tylonolide was obtained.

(i) NMR (CDCl₃)

| δ (ppm) | H number | Form | J (Hz) | |
|---|---|---|---|---|
| 1.82 | 3 | s | | Me(21) |
| 2.31 | 6 | s | | 3'-NMe₂ |
| about 2.4 | 4 | m | | 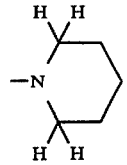 |
| 4.25 | 1 | d₁',₂' | 7.5 | H₁' |
| 4.78 | 1 | m | | H₁₅ |
| 6.30 | 1 | d₁₀,₁₁ | 16 | H₁₀ |
| 7.40 | 1 | d₁₁,₁₀ | 16 | H₁₁ |

(ii) IR (KBr) (cm⁻¹):

| | |
|---|---|
| 2980 | —CH₃ |
| 2950 | —CH₂— |
| 1730 | —COO— |
| 1680 | >C=O |
| 1600 | —C=C—C=C— |

(iii) Colorless solid (iv) Anal. for C₃₅H₆₀N₂O₇:

| | C (%) | H (%) | N (%) |
|---|---|---|---|
| Calculated: | 67.71 | 9.74 | 4.51 |
| Found: | 67.65 | 9.62 | 4.66 |

(v) $[\alpha]_D^{22}$ + 42° (c 1.0, CHCl₃)

(vi) UV $\lambda_{max}^{MeOH}$ 284 nm (ε = 25,000)

EXAMPLE 36

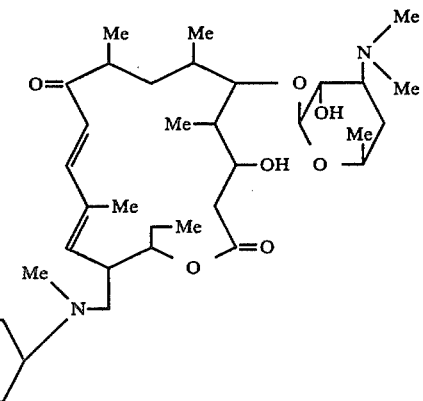

By following the same procedure as in Example 34 using 84 mg of 19-decarbonyl-22,4'-dideoxy-22-iodomycaminosyl tylonolide and 72 mg of N-methylcyclohexylamine, 77.7 mg (yield 92%) of 19-decarbonyl-22,4'-dideoxy-22-(N-methylcyclohexylamine)-mycaminosyl tylonolide was obtained.

(i) NMR (CDCl₃):

| δ (ppm) | H number | Form | J (Hz) | |
|---|---|---|---|---|
| 1.83 | 3 | s | | Me(21) |
| 2.20 | 3 | s | | (Me-N-cyclohexyl) |
| 2.30 | 6 | s | | 3'-NMe₂ |

-continued

| | | | | |
|---|---|---|---|---|
| 4.27 | 1 | $d_{1',2'}$ | 7.5 | $H_{1'}$ |
| 4.77 | 1 | m | | $H_{15}$ |
| 6.32 | 1 | $d_{10,11}$ | 16 | $H_{10}$ |
| 7.39 | 1 | $d_{11,10}$ | 16 | $H_{11}$ |

(ii) IR (KBr) (cm$^{-1}$):

| | |
|---|---|
| 2980 | —CH$_3$ |
| 2950 | —CH$_2$— |
| 1730 | —COO— |
| 1680 |  |
| 1600 | —C=C—C=C— |

(iii) Colorless solid (iv) Anal. for $C_{37}H_{65}N_2O_7$:

| | C (%) | H (%) | N (%) |
|---|---|---|---|
| Calculated: | 68.49 | 9.94 | 4.32 |
| Found: | 68.27 | 9.83 | 4.51 |

(v) $[\alpha]_D^{22}$ + 77° (c 1.0, CHCl$_3$)

(vi) UV $\lambda_{max}^{MeOH}$ 284 nm ($\epsilon$ = 25,000)

EXAMPLE 37

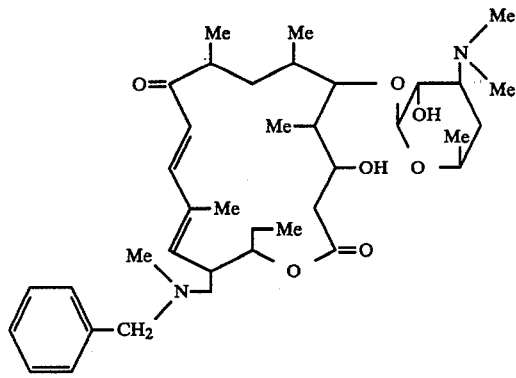

By following the same procedure as in Example 34 using 94.3 mg of 19-decarbonyl-22,4'-dideoxy-22-iodomycaminosyl tylonolide and 86 mg of N-methylbenzylamine, 81 mg (yield 87%) of 19-decarbonyl-22,4'-dideoxy-22-(N-methylbenzylamino)mycaminosyl tylonolide was obtained.

(i) NMR (CDCl$_3$):

| δ (ppm) | H number | Form | J (Hz) | |
|---|---|---|---|---|
| 1.83 | 3 | s | | Me(21) |
| 2.20 | 3 | s | | 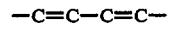 |
| 2.30 | 6 | s | | 3'-NMe$_2$ |
| 4.24 | 1 | $d_{1',2'}$ | 7.5 | $H_{1'}$ |
| 4.77 | 1 | m | | $H_{15}$ |
| 6.33 | 1 | $d_{10,11}$ | 16 | $H_{10}$ |
| 7.35 | 5 | s | | 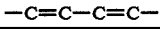 |

(ii) IR (KBr) (cm$^{-1}$):

| | |
|---|---|
| 2980 | —CH$_3$ |
| 2950 | —CH$_2$— |
| 1730 | —COO— |
| 1680 |  |
| 1595 | —C=C—C=C— |

(iii) Colorless solid (iv) Anal. for $C_{38}H_{60}N_2O_7$:

| | C (%) | H (%) | N (%) |
|---|---|---|---|
| Calculated: | 69.48 | 9.21 | 4.26 |
| Found: | 69.20 | 9.11 | 4.32 |

(v) $[\alpha]_D^{23}$ + 32° (c 1.0, CHCl$_3$)

(vi) UV $\lambda_{max}^{MeOH}$ 284 nm ($\epsilon$ = 26,000).

EXAMPLE 38

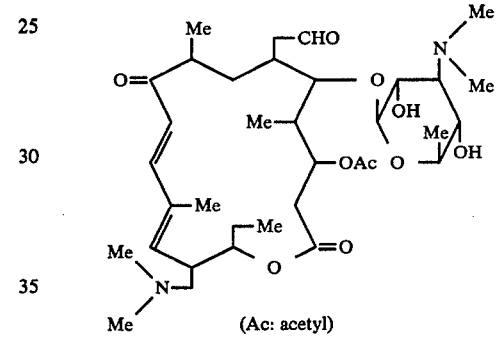

(Ac: acetyl)

In 1.1 ml of anhydrous pyridine was dissolved 55.4 mg of 23-deoxy-23-dimethylaminomycaminosyl tylonolide diethylacetal and after thereto 0.14 ml of acetic anhydride, the mixture was heated at 60° C. for 36 hours. The reaction was, then, stopped by the addition of a small amount of water and after distilling off the solvent, chloroform was added to the reaction mixture. The reaction mixture was washed with a saturated aqueous sodium hydrogencarbonate solution and then a saturated aqueous sodium sulfate solution, and after drying with anhydrous sodium sulfate, the solvent was distilled off.

The residue thus formed was dissolved in 2.8 ml of methanol and the solution was heated at 50° C. for 6 hours. Then, the solvent was distilled off, the residue thus obtained was dissolved in chloroform and the solution was washed with a saturated aqueous sodium hydrogencarbonate solution and then a saturated aqueous sodium sulfate solution, and after drying the solution with anhydrous sodium sulfate, the solvent was distilled off. The residue was dissolved in 1.1 ml of acetonitrile and after adding thereto 2.5 ml of hydrochloric acid, the mixture was allowed to stand for 60 minutes at room temperature. To the reaction system was added 28 mg of sodium hydrogencarbonate to stop the reaction and then the product was extracted three times each time with chloroform. The chloroform layers were combined with each other and the mixture was washed with a saturated aqueous sodium sulfate solution and dried with anhydrous sodium sulfate.

The solvent was distilled off and the residue thus formed was purified by a silica gel column using a developing system composed of chloroform-methanol-concentrated aqueous ammonia (18:1:0.1) to provide 36.4 mg (yield 66%) of 3-O-acetyl-23-deoxy-23-dimethylaminomycaminosyl tylonolide.

(i) NMR (CDCl₃):

| δ (ppm) | H number | Form | J (Hz) | |
|---|---|---|---|---|
| 1.86 | 3 | s | | H$_{22}$ |
| 2.14 | 3 | s | | 3-O—Ac |
| 2.21 | 6 | s | | 23-NMe$_2$ |
| 2.53 | 6 | s | | 3'-NMe$_2$ |
| 4.23 | 1 | d$_{1',2'}$ | 7.5 | H$_{1'}$ |
| 4.68 | 1 | m | | H$_{15}$ |
| 5.20 | 1 | d$_{3,2a}$ | ~10 | H$_3$ |
| 5.87 | 1 | d$_{13,14}$ | 10.0 | H$_{13}$ |
| 6.30 | 1 | d$_{10,11}$ | 16.0 | H$_{10}$ |
| 7.50 | 1 | d$_{11,10}$ | 16.0 | H$_{11}$ |
| 9.74 | 1 | s | | H$_{20}$ |

(ii) IR (KBr) (cm⁻¹):

| | |
|---|---|
| 2970 | —CH$_3$ |
| 2940 | —CH$_2$— |
| ~1740 | —COO—, —CHO |
| 1680 |  |
| 1595 | —C=C—C=C— |

(iii) Colorless amorphous solid (reprecipitated from acetone-hexane)

(iv) Anal. for C₃₅H₅₈N₂O₁₀:

| | C (%) | H (%) | N (%) |
|---|---|---|---|
| Calculated: | 63.04 | 8.77 | 4.20 |
| Found: | 62.89 | 8.82 | 4.27 |

(v) $[\alpha]_D^{25}$ + 43° C. (c 1.0, CHCl₃)

(vi) UV $\lambda_{max}^{MeOH}$ 283 nm (ε = 23,000)

(vii) Rf: 0.38   Wako gel B-5
chloroform-methanol (9:1).

EXAMPLE 39

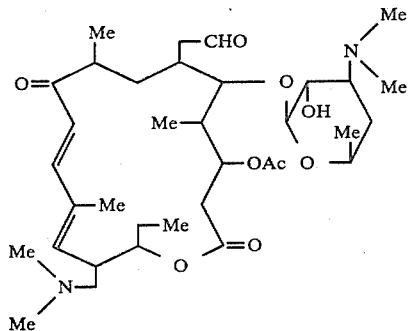

By following the same procedure as in Example 38 using 44.8 mg of 23,4'-dideoxy-23-dimethylaminomycaminosyl tylonolide diethylacetal, 25.6 mg (yield 60%) of 3-O-acetyl-23,4'-dideoxy-23-dimethylaminomycaminosyl tylonolide was obtained.

(i) NMR (CDCl₃):

| δ (ppm) | H number | Form | J (Hz) | |
|---|---|---|---|---|
| 1.85 | 3 | s | | H$_{22}$ |
| 2.12 | 3 | s | | 3-O—Ac |
| 2.21 | 6 | s | | 23-NMe$_2$ |
| 2.31 | 6 | s | | 3'-NMe$_2$ |
| 4.22 | 1 | d$_{1',2'}$ | 7.5 | H$_{1'}$ |
| 4.67 | 1 | m | | H$_{15}$ |
| 5.20 | 1 | d$_{3,2a}$ | ~10 | H$_3$ |
| 5.87 | 1 | d$_{13,14}$ | 10.0 | H$_{13}$ |
| 6.33 | 1 | d$_{10,11}$ | 16.0 | H$_{10}$ |
| 7.53 | 1 | d$_{11,10}$ | 16.0 | H$_{11}$ |
| 9.74 | 1 | s | | H$_{20}$ |

(ii) IR (KBr) (cm⁻¹):

| | |
|---|---|
| 2970 | —CH$_3$ |
| 2940 | —CH$_2$— |
| ~1740 | —COO— |
| | —CHO |
| 1680 |  |
| 1595 | —C=C—C=C— |

(iii) Colorless amorphous solid (reprecipitated from acetone-hexane)

(iv) Anal. for C₃₅H₅₈N₂O₉:

| | C (%) | H (%) | N (%) |
|---|---|---|---|
| Calculated: | 64.59 | 8.98 | 4.30 |
| Found: | 64.26 | 8.77 | 4.25 |

(v) $[\alpha]_D^{25}$ + 47° (c 1.0, CHCl₃)

(vi) UV $\lambda_{max}^{MeOH}$ 283.5 nm (ε = 24,000)

(vii) Rf: 0.31   Wako gel B-5
chloroform-methanol (10:1).

EXAMPLE 40

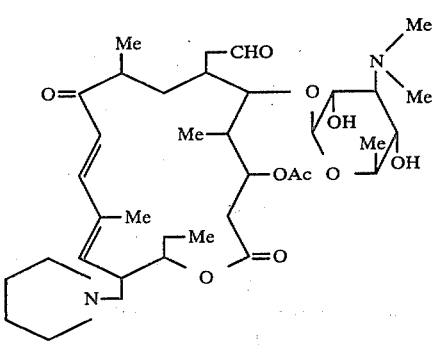

By following the same procedure as in Example 38 using 49.9 mg of 23-deoxy-23-pyrrolidinomycaminosyl tylonolide diethylacetal, 28.9 mg (yield 60.5%) of 23-deoxy-3-O-acetyl-23-pyrrolidinomycaminosyl tylonolide was obtained.

Reprecipitated amount: 24.5 mg (reprecipitation yield 84.8%)

(i) NMR (CDCl₃):

| δ (ppm) | H number | Form | J (Hz) | |
|---|---|---|---|---|
| 1.83 | 3 | s | | H$_{22}$(12-CH$_3$) |
| 2.13 | 3 | s | | 3-O—Ac |
| 2.51 | 6 | s | | 3'-NMe$_2$ |
| 4.22 | 1 | d$_{1',2'}$ | 7.5 | H$_{1'}$ |
| 4.68 | 1 | m | | H$_{15}$ |
| 5.22 | 1 | m | | H$_3$ |
| 5.92 | 1 | d$_{13,14}$ | 10.0 | H$_{13}$ |
| 6.30 | 1 | d$_{10,11}$ | 16.0 | H$_{10}$ |
| 7.50 | 1 | d$_{11,10}$ | 16.0 | H$_{11}$ |

-continued

| 9.71 | 1 | s | H$_2$O |
|---|---|---|---|

(ii) IR (KBr) (cm$^{-1}$):

| 2970 | —CH$_3$ |
|---|---|
| 2940 | —CH$_2$— |
| 1740 | —COO—, —CHO |
| 1680 | $\diagdown$C=O$\diagup$ |
| 1595 | —C=C—C=C— |

(iii) Colorless amorphous solid (reprecipitated from n-hexane-acetone)

(iv) Anal. for C$_{37}$H$_{60}$N$_2$O$_{10}$:

| | C (%) | H (%) | N (%) |
|---|---|---|---|
| Calculated: | 64.14 | 8.73 | 4.04 |
| Found: | 63.98 | 8.65 | 4.32 |

(v) $[\alpha]_D^{22.5}$ + 42° (c 1.0, CHCl$_3$):

(vi) UV $\lambda_{max}^{MeOH}$ 281 nm ($\epsilon$ = 22,000)

(vii) Rf: 0.45 Wako gel B-5
chloroform-methanol-concentrated
aqueous ammonia (12:1:0.1)

EXAMPLE 41

In 50 ml of acetonitrile was dissolved 10.2 g of 23-deoxy-23-iodomycaminosyl tylonolide and after adding thereto 5 ml of acetic anhydride, the mixture was allowed to stand for one hour. Acetonitrile was distilled off under reduced pressure, and after adding 500 ml of benzene and 300 ml of a saturated aqueous sodium hydrogencarbonate solution to the residue, the mixture was shaked. An organic layer thus formed was recovered, washed with water, and after drying with anhydrous magnesium sulfate, benzene was distilled off under reduced pressure to provide 10.1 g of crude 23-deoxy-23-iodo-2',4'-di-O-acetylmycaminosyl tylonolide diethylacetal.

The foregoing reaction product (10.1 g) was dissolved in 300 ml of acetonitrile containing 10.5 g of diethylamine and the solution was heated at 70°-80° C. for 3 hours in a closed tube. After cooling, acetonitrile was distilled off under reduced pressure and the residue thus formed was dissolved in 300 ml of chloroform. The solution was washed with water, dried with anhydrous magnesium sulfate, and then chloroform was distilled off. The red-brown residue thus obtained was purified by column chromatography using 800 ml of silica gel and an eluate consisting of chloroform and methanol (10:1) to provide 4.4 g of 23-deoxy-23-ethylamino-2',4'-O-acetylmycaminosyl tylonolide diethylacetal as a lemmon yellow caramel.

The foregoing product (600 mg) was dissolved in 12 ml of acetonitrile and after adding thereto 79.5μ liter of acetic anhydride at room temperature, the mixture was allowed to stand for one hour at room temperature. After distilling off acetonitrile under reduced pressure, 10 ml of a saturated aqueous sodium hydrogencarbonate solution was added to the residue and the product was extracted with 50 ml of chloroform. The chloroform extract was washed with water and after drying with anhydrous magnesium sulfate, chloroform was distilled off to provide crude 23-N-acetylethylamino-23-deoxy-2',4'-di-O-acetylmycaminosyl tylonolide diethylacetal.

The foergoing product was dissolved in 30 ml of methanol and after maintaining the solution at 50°-55° C. for 6 hours, methanol was distilled off under reduced pressure. To the residue were added 10 ml of a saturated aqueous sodium hydrogen-carbonate solution and 30 ml of chloroform followed by shaking well, the chloroform layer was recovered. The aqueous layer thus formed was extracted with 20 ml of chloroform and the chloroform layer was combined with the foregoing chloroform layer. The resultant chloroform solution was washed with water, dried with anhydrous magnesium sulfate, and then chloroform was distilled off under reduced pressure to provide a yellowish caramel.

The caramel was purified by column chromatography using 70 ml of silica gel and an eluate comprising chloroform, methanol, and concentrated aqueous ammonia (15:1:0.1) to provide 260 mg of 23-N-acetylethylamino-23-deoxymycaminosyl tylonolide.

(i) NMR (CDCl$_3$) δ(ppm):

$$\overset{CH_2CH_3}{|}$$

1.76 (3H, s, H$_{22}$), 2.02 (3H, s, NCOCH$_3$), 2.56 (6H, s, NMe$_2$), 4.28 (1H, d, H$_{1'}$), 4.80 (1H, m, H$_{16}$), 5.73 (1H, d, H$_{13}$).
6.30 (1H, d, H$_{10}$), 7.28 (1H, d, H$_{11}$), 9.70 (1H, s, CHO).

(ii) Mass (m/z):
666(M$^+$), 566(M$^+$ −100), 522(M$^+$ −144), 476(M$^+$ −190).

(iii) IR (KBr) (cm$^{-1}$):
3400, 2950, 2900, 2850, 1710, 1670, 1630, 1620, 1580.

EXAMPLE 42

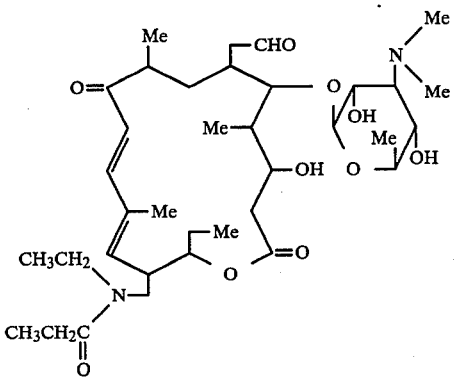

In 12 ml of acetonitrile was dissolved 600 mg of 23-deoxy-23-ethylamino-2',4'-di-O-acetylmycaminosyl tylonolide diethylacetal obtained as an intermediate in Example 41, and after adding thereto 112μ liters of chloropropionic anhydride, the mixture was allowed to stand for one hour at room temperature. After distilling off acetonitrile from the reaction mixture under reduced pressure, 10 ml of a saturated aqueous sodium hydrogencarbonate solution and 50 ml of chloroform were added to the residue followed by shaking, the mixture was allowed to stand to provide a chloroform layer. The chloroform layer was washed with water, dried with anhydrous sodium sulfate, and chloroform was distilled off.

The residue was dissolved in 30 ml of methanol and after maintaining the solution at 50°–55° C. for 6 hours, methanol was distilled off under reduced pressure and the residue thus obtained was dissolved in 50 ml of chloroform.

The chloroform solution was washed with 20 ml of a saturated aqueous sodium hydrogencarbonate solution and then 20 ml of water, dried with anhydrous sodium sulfate, and then chloroform was was distilled off under reduced pressure. The residue thus obtained was dissolved in a mixture of 25 ml of 0.1N-hydrochloric acid and 13 ml of acetonitrile and the solution was allowed to stand for 2 hours at room temperature.

The solution was alkalified by sodium hydrogencarbonate and extracted with 30 ml, 20 ml, and then 10 ml of chloroform. The extracts were washed with water, dried with anhydrous magnesium sulfate, and then chloroform was distilled off under reduced pressure. The residue was purified by column chromatography using 70 ml of silica gel and an eluate comprising chloroform, methanol, and concentrated aqueous ammonia (15:1:0.1) to provide 278 mg of yellowish amorphous powder of 23-deoxy-23-N-ethylpropionylaminomycaminosyl tylonolide.

(i) NMR (CDCl$_3$) δ(ppm):
1.75 (3H, s, H$_{22}$), 2.55 (6H, s, —NMe$_2$), 4.27 (1H, d, H$_{1'}$), 4.80 (1H, m, H$_{16}$), 5.72 (1H, d, H$_{13}$), 6.26, (1H, d, H$_{10}$), 7.27 (1H, d, H$_{11}$), 9.70 (1H, s, —CHO)
(ii) Mass (m/z):
680 (M$^+$), 662(M$^+$ −18), 566 (M$^+$ −114), 536 (M$^+$ −144), 490 (M$^+$ −190).
(iii) IR (KBr) (cm$^{-1}$):
3400, 2950, 2920, 2850, 1710, 1670, 1630, 1620, 1580

EXAMPLE 43

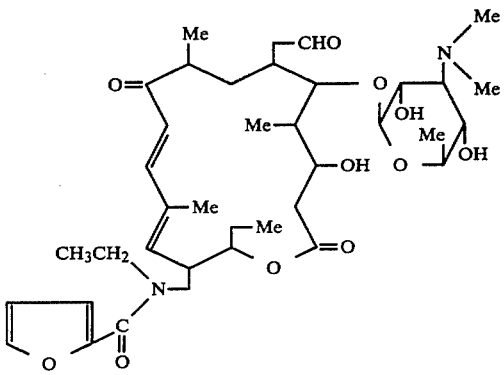

By following the same procedure as in Example 42 using 600 mg of 23-deoxy-23-ethylamino-2',4'-di-O-acetylmycaminosyl tylonolide diethylacetal obtained in Example 41 as an intermediate and 110.1 mg of furoic acid chloride, 397 mg of yellowish amorphous powder of 23-deoxy-23-N-(2-furoyl)ethylaminomycaminosyl tylonolide.

(i) NMR (CDCl$_3$) δ(ppm):
1.71 (3H, s, H$_{22}$), 2.48 (6H, s, NMe$_2$), 4.25 (1H, d, H$_{1'}$), 4.80 (1H, m, H$_{15}$), 5.74 (1H, d, H$_{13}$), 6.21 (1H, d, H$_{10}$),

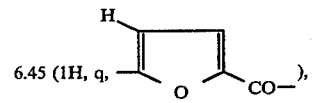
6.45 (1H, q, ),

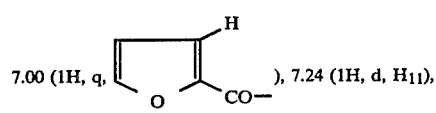
7.00 (1H, q, ), 7.24 (1H, d, H$_{11}$),

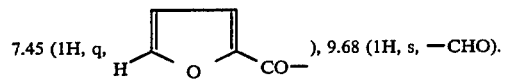
7.45 (1H, q, ), 9.68 (1H, s, —CHO).

(ii) Mass (m/z):
718 (M$^+$), 710 (M$^+$ −18), 574 (M$^+$ −144), 528 (M$^+$ −190).
(iii) IR (KBr) (cm$^{-1}$):
3410, 2950, 2910, 2860, 1710, 1670, 1610, 1585.

EXAMPLE 44

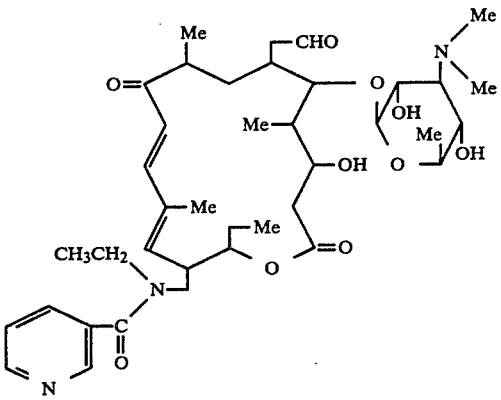

In 12 ml of acetonitrile was dissolved 600 mg of 23-deoxy-23-ethylamino-2',4'-di-O-acetylmycaminosyl tylonolide diethylacetal and after adding thereto 150.2 mg of nicotinic acid chloride hydrochloride at room temperature, the mixture was allowed to stand for 30 minutes. Then, 85.2 mg of triethylamine was added to the mixture and the resultant mixture was allowed to stand for 30 minutes. Acetonitrile was distilled off under reduced pressure and the residue was dissolved in 50 ml of chloroform. Then, 20 ml of a saturated aqueous sodium hydrogen-carbonate solution was added to the solution and after shaking and then allowed to stand the mixture, the chloroform layer was recovered, washed with water, and dried. Thereafter, chloroform was distilled off under reduced pressure to provide a brownish amorphous powder. The product was dissolved in 30 ml of methanol and after allowing to stand the solution at 50°–55° C. for 4 hours, methanol was distilled off under reduced pressure. The residue was dissolved in 50 ml of chloroform and the solution was washed with 20 ml of a saturated aqueous sodium hydrogenchloride solution and then 20 ml of water. Then, after drying the solution with anhydrous magnesium sulfate, chloroform was distilled off under reduced pressure.

The residue was dissolved in a mixture of 25 ml of 0.1N-hydrochloric acid and 13 ml of acetonitrile and the solution was allowed to stand for 2 hours at room temperature. Then, the solution was alkalified with sodium hydrogencarbonate and extracted with 30 ml, 20 ml, and 10 ml of chloroform. The extracts were combined with each other, washed with water, dried with anhydrous magnesium sulfate, and chloroform was distilled off under reduced pressure. The residue thus obtained was purified by column chromatography using 70 ml of silica gel and an eluate consisting of chloroform, methanol, and concentrated aqueous ammonia (10:1:0.1) to provide 347 mg of yellowish amorphous powder of 23-deoxy-23-N-nicotinoylethylaminomycaminosyl tylonolide.

(i) NMR (CDCl$_3$) δ(ppm):
1.84 (3H, s, H$_{22}$), 2.53 (6H, s, NMe$_2$), 4.28 (1H, d, H$_{1'}$), 4.89 (1H, m, H$_{15}$), 5.80 (1H, d, H$_{13}$), 6.32 (1H, d, H$_{10}$),

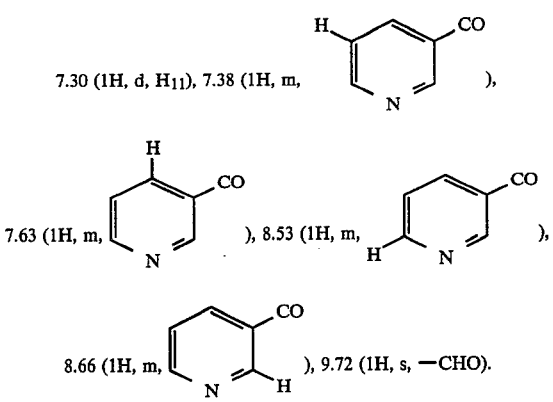

7.30 (1H, d, H$_{11}$), 7.38 (1H, m, ...), 7.63 (1H, m, ...), 8.53 (1H, m, ...), 8.66 (1H, m, ...), 9.72 (1H, s, —CHO).

(ii) Mass (m/z):
729 (M$^+$), 711 (M$^+$ −18), 585 (M$^+$ −144), 539 (M$^+$ −190).
(iii) IR (KBr) (cm$^{-1}$):
3400, 2950, 2910, 2860, 1710, 1665, 1625, 1620, 1580.

EXAMPLE 45

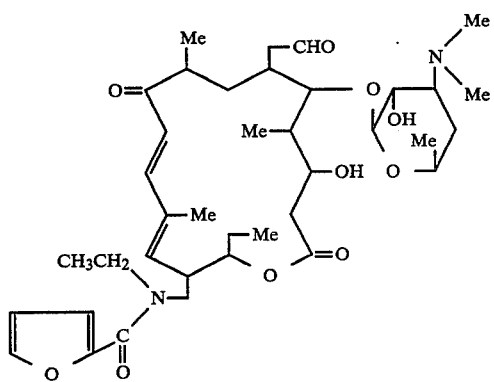

In 20 ml of acetonitrile was dissolved 4 g of 23,4'-dideoxy-23-iodomycaminosyl tylonolide diethylacetal and after adding thereto 800 mg of acetic anhydride at room temperature, the mixture was allowed to stand for one hour. Thereafter, acetonitrile was distilled off under reduced pressure, 200 ml of benzene and 100 ml of a saturated aqueous sodium hydrogencarbonate solution were added to the residue, and the mixture was shaken. Then, the benzene layer thus formed was recovered, washed with water, dried with anhydrous sodium sulfate, and benzene was distilled off under reduced pressure to provide crude 23,4'-dideoxy-23-iodo-2'-O-acetylmycaminosyl tylonolide diethylacetal. The product was dissolved in 75 ml of acetonitrile and after adding thereto 75 ml of a 2M ethylamine acetonitrile solution, the resultant mixture was heated at 70°–80° C. for 2 hours in a closed tube. After cooling the reaction mixture, acetonitrile was distilled off under reduced pressure and the residue was dissolved in 200 ml of chloroform. The solution thus obtained was washed with water, dried by anhydrous magnesium sulfate, and then chloroform was distilled off under reduced pressure. The brownish residue thus obtained was purified by column chromatography using 300 ml silica gel and an eluate consisting of chloroform and methanol (20:1) and then an eluate consisting of chloroform and methanol (10:1) to provide 2.8 g of a lemmon yellow amorphous powder of 23,4'-dideoxy-23-ethylamino-2'-O-acetylmycaminosyl tylonolide diethylacetal.

In 6 ml of acetonitrile was dissolved 300 mg of the foregoing product and after adding thereto 59.4 mg of furoic acid chloride, the mixture was allowed to stand for one hour at room temperature. Acetonitrile was distilled off under reduced pressure and after adding 20 ml of a saturated aqueous sodium hydrogencarbonate solution and 40 ml of chloroform to the residue, the mixture was shaken and then allowed to stand. The chloroform layer thus formed was recovered, washed with water, dried, and then chloroform was distilled off under reduced pressure to provide crude 23,4'-dideoxy-23-N-(2-furoyl)ethylamino-2'-O-acetylmycaminosyl tylonolide diethylacetal. The product was dissolved in 20 ml of methanol and after allowing to stand the solution for 7 hours at 50°–60° C., methanol was distilled off under reduced pressure. The residue was dissolved in 40 ml of chloroform, the solution was washed with 20 ml of a saturated aqueous sodium hydrogencarbonate solution and then 20 ml of water, dried by anhydrous magnesium sulfate, and then chloroform was distilled off under reduced pressure to provide crude 23,4'-dideoxy-23-N-(2-furoyl)ethylaminomycaminosyl tylonolide diethylacetal.

The product was dissolved in a mixture of 13 ml of 0.1N hydrochloric acid and 7 ml of acetonitrile and the solution was allowed to stand for 2 hours at room temperature. The reaction product was alkalified with sodium hydrogencarbonate and extracted with 30 ml, 20 ml, and then 10 ml of chloroform. The chloroform extracts were combined with each other, washed with water, dried by anhydrous magnesium sulfate, and then chloroform was distilled off under reduced pressure. The residue was purified by column chormatography using 40 ml of silica gel and an eluate consisting of chloroform, methanol, and concentrated aqueous ammonia (15:1:0.1) to provide 183 mg of yellowish amorphous powder of 23,4'-dideoxy-23-N-(2-furoyl)ethylaminomycaminosyl tylonolide.

(i) NMR (CDCl$_3$) δ(ppm):
1.74 (3H, s, H$_{22}$), 2.27 (6H, s, NMe$_2$), 4.23 (1H, d, H$_{11}$), 4.84 (1H, m, H$_{15}$), 5.79 (1H, d, H$_{13}$), 6.29 (1H, d, H$_{10}$),

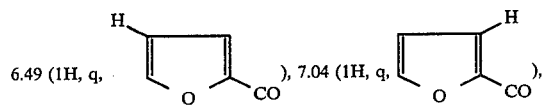

6.49 (1H, q, ...), 7.04 (1H, q, ...), 7.28 (1H, d, H₁₁), 7.49 (1H, q, 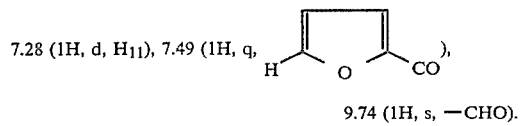), 9.74 (1H, s, —CHO).

(ii) Mass (m/z):
702 (M⁺), 684 (M⁺ −18), 574 (M⁺ −128), 528 (M⁺ −174).
(iii) IR (KBr) (cm⁻¹):
3410, 2950, 2910, 1850, 1710, 1670, 1615, 1585.

EXAMPLE 46

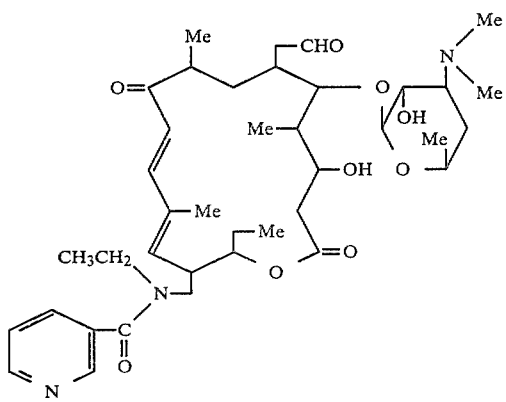

In 6 ml of acetonitrile was dissolved 300 mg of 23,4′-dideoxy-23-ethylamino-2′-O-acetylmycaminosyl tylonolide diethylacetal obtained in Example 45 as an intermediate and after adding thereto 81.1 mg of nicotinic acid chloride hydrochloride and 63.3 μl of triethylamine, the mixture was allowed to stand for 3 hours at room temperature. Thereafter, acetonitrile was distilled off under reduced pressure, 20 ml of a saturated aqueous sodium hydrogencarbonate solution and 40 ml of chloroform were added to the residue, and after shaking the mixture followed by allowing to stand, the chloroform layer thus formed was recovered, washed with water, and dried by anhydrous magnesium sulfate. Then, chloroform was distilled off under reduced pressure to provide 23,4′-dideoxy-23-N-nicotinoylethylamino-2′-O-acetylmycaminosyl tylonolide diethylacetal as the crude product. The product was dissolved in 20 ml of methanol and after allowing to stand the mixture for 7 hours at 50°–55° C., methanol was distilled off under reduced pressure. The residue was dissolved in 40 ml of chloroform and the solution was washed with 20 ml of a saturated sodium hydrogencarbonate solution and then 10 ml of water, dried by anhydrous magnesium sulfate, and then chloroform was distilled off under reduced pressure to provide crude 23,4′-dideoxy-23-N-nicotinoylethylaminomycaminosyl tylonolide diethylacetal. The product was dissolved in a mixture of 13 ml of 0.1N aqueous hydrochloric acid and 7 ml of acetonitrile and the solution was allowed to stand for 2 hours at room temperature. The solution was alkalified with sodium hydrogencarbonate and extracted with 20 ml, 10 ml, and then 10 ml of chloroform. The extracts were combined with each other, washed with water, dried with anhydrous magnesium sulfate, and then chloroform was distilled off under reduced pressure. The residue was purified by column chromatography using 40 ml of silica gel and an eluate consisting of chloroform, methanol, and concentrated aqueous ammonia (15:1:0.1) to provide 162 mg of yellowish noncrystalline powder of 23,4′-dideoxy-23-N-nicotinoylethylaminomycaminosyl tylonolide.

(i) NMR (CDCl₃) δ(ppm):
1.81 (3H, s, H₂₂), 2.27 (6H, s, NMe₂), 4.23 (1H, d, H₁·),
4.87 (1H, m, H₁₅), 5.80 (1H, d, H₁₃), 6.35 (1H, d, H₁₀), 7.34 (1H, d, H₁₁), 7.38 (1H, m, 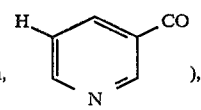), 7.63 (1H, m, 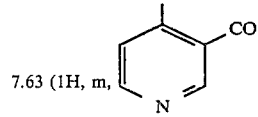), 8.53 (1H, m, 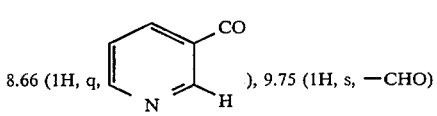

8.66 (1H, q, ), 9.75 (1H, s, —CHO)

(ii) Mass (m/z):
713 (M⁺), 695 (M⁺ −18), 585 (M⁺ −128), 539 (M⁺ −174).
(iii) IR (KBr) (cm⁻¹):
3410, 2950, 2910, 2850, 1710, 1620, 1580.

EXAMPLE 47

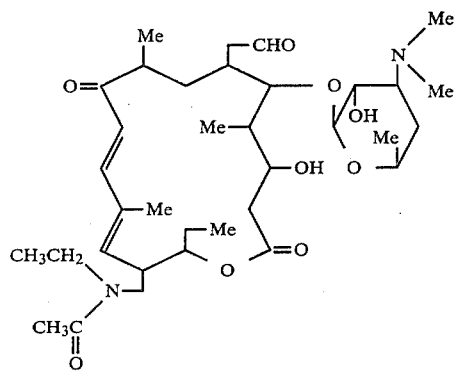

In 60 ml of acetonitrile was dissolved in 3 g of 23,4′-dideoxy-23-iodomycaminosyl tylonolide diethylacetal and after adding thereto 1.77 g of ethylamine, the mixture was heated at 70°–80° C. for 3 hours in a closed tube. After cooling, acetonitrile was distilled off under reduced pressure, the residue was dissolved in 200 ml of chloroform, and the solution was washed with water, dried with anhydrous magnesium sulfate, and then chloroform was distilled off under reduced pressure to provide 2.0 g of a brownish amorphous powder of 23,4′-dideoxy-23-ethylaminomycaminosyl tylonolide diethylacetal. The product (1.8 g) thus obtained was dissolved in 18 ml of acetonitrile and after adding thereto 0.55 ml of acetic anhydride at room temperature and allowing to stand the mixture for one hour, acetonitrile was distilled off under reduced pressure. The residue was dissolved in 200 ml of chloroform, the solution was washed with a satruated aqueous sodium hydrogencarbonate solution, water, and then a saturated aqueous sodium chloride solution, and dried with anhydrous magnesium sulfate, and then chloroform was distilled off under reduced pressure to provide crude 23-N- acetylethylamino-23,4'-dideoxy-2'-O-acetylmycaminosyl tylonolide. The product was dissolved in 90 ml of methanol and the solution was heated at 50°-60° C. for 7 hours. Methanol was, then, distilled off, the residue was dissolved in 200 ml of chloroform, the solution was washed with a saturated aqueous sodium hydrogencarbonate solution, water, and then a saturated aqueous sodium chloride solution, and after drying with anhydrous magnesium sulfate, chloroform was distilled off to provide the foregoing compound from which the 2'-O-acetyl group was removed.

The crude product was dissolved in a mixture of 46 ml of 0.1N HCl and 30 ml of acetonitrile and the solution was allowed to stand for 3 hours at room temperature. The solution was alkalified with sodium hydrogencarbonate, extracted with 100 ml, 30 ml, and then 20 ml of chloroform, the extracts were combined with each other, washed with water, and dried with anhydrous magnesium sulfate, and then chloroform was distilled off under reduced pressure to provide a crude product of the desired compound.

The product was purified by column chromatography using 200 ml of silica gel and an eluate consisting of chloroform, methanol, and concentrated aqueous ammonia (18:1:0.1) to provide 980 mg of 23-N-acetylethylamino-23,4'-dideoxymycaminosyl tylonolide.

(i) NMR (CDCl$_3$) δ(ppm):
1.73 (3H, s, H$_{22}$), 2.00 (3H, s, NCOCH$_3$), 2.23 (6H, s, NMe$_2$), 4.18 (1H, d, H$_{1'}$), 4.76 (1H, m, H$_{15}$), 5.71 (1H, d, H$_{13}$), 6.27 (1H, d, H$_{10}$), 7.27 (1H, d, H$_{11}$), 9.69 (1H, s, CHO)
(ii) IR (KBr) (cm$^{-1}$):
3450, 2960, 2930, 2860, 1720, 1680, 1640, 1590.
(iii) Mass (m/z):
650 (M$^+$), 550 (M$^+$−100), 522 (M$^+$−128), 476 (M$^+$−174).

EXAMPLE 48

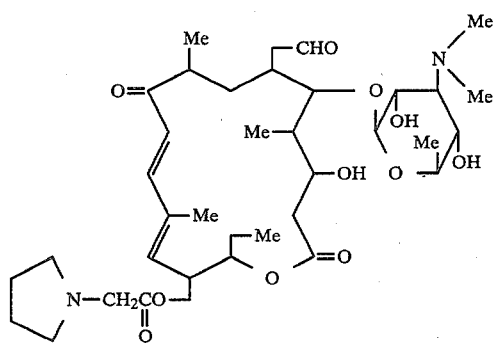

(a) In 34 ml of anhydrous pyridine was dissolved 3.4 g of 2',4'-di-O-acetylmycaminosyl tylonolide diethylacetal and after cooling the solution to −20° C. and adding gradually 1.08 g of chloroacetyl chloride to the solution, the mixture was stirred for 3 hours. The reaction mixture was poured into 100 ml of a saturated aqueous sodium hydrogencarbonate solution and extracted twice each time with 100 ml of benzene. The extract was washed with 100 ml of water and then 100 ml of a saturated aqueous sodium hydrogencarbonate solution, dried by anhydrous magnesium sulfate, and benzene was distilled off under reduced pressure. The black-brown oil thus obtained was purified by column chromatography using 400 ml of silica gel and an eluate consisting of benzene and acetone (2:1) to provide 3.0 g of yellow-brown amorphous powder of 23-O-chloroacetyl-2',4'-di-O-acetylmycaminosyl tylonolide diethylacetal.

(b) foregoing product (400 mg) was dissolved in 10 ml of acetonitrile and after adding thereto 69.6 mg of pyrrolidine, the mixture was stirred for 3 hours at room temperature. Acetonitrile was distilled off under reduced pressure, the residue was dissolved in 50 ml of benzene, washed with 20 ml of a saturated aqueous sodium hydrogencarbonate solution, 20 ml of water, and then 20 ml of a saturated aqueous sodium chloride solution, dried by anhydrous magnesium sulfate, and then benzene was distilled off under reduced pressure. The residue thus obtained was dissolved in 15 ml of methanol and the solution was allowed to stand for 20 hours at room temperature. Then, methanol was distilled off under reduced pressure, the residue was dissolved in a mixture of 7 ml of acetonitrile and 14 ml of 0.1N HCl and after allowing to stand the solution for 2 hours at room temperature, the solution was alkalified with sodium hydrogencarbonate and extracted thrice each time with 20 ml of chloroform. The chloroform extracts were combined with each other, washed with 20 ml of water and then 20 ml of a saturated aqueous sodium chloride solution, dried by anhydrous magnesium sulfate, and then chloroform was distilled off under reduced pressure to provide a black-brown caramel. The product was purified by column chromatography using 50 ml of silica gel and an eluate consisting of chloroform, methanol, and concentrated aqueous ammonia (15:1:0.1) to provide 103.8 mg of a yellowish amorphous powder of 23-O-pyrrolidinoacetylmycaminosyl tylonolide.

(i) NMR (CDCl$_3$) δ(ppm):
1.82 (3H, s, H$_{22}$), 2.51 (3H, s, NMe$_2$), 3.36 (2H, s, —OCOCH$_2$N), 4.10–4.40 (3H, m, H$_{1'}$, —CH$_2$OCOCH$_2$N), 4.94 (1H, m, H$_{15}$), 5.80 (1H, d, H$_{13}$), 6.30 (1H, d, H$_{10}$), 7.32 (1H, d, H$_{11}$), 9.71 (1H, s, —CHO).
(ii) IR (KBr) (cm$^{-1}$):
3430, 2950, 2910, 2860, 1715, 1670, 1620, 1585.
(iii) Mass (m/z):
708 (M$^+$), 639 (M$^+$-69), 504 (M$^+$-144), 534 (M$^+$-174), 518 (M$^+$-190).

EXAMPLE 49

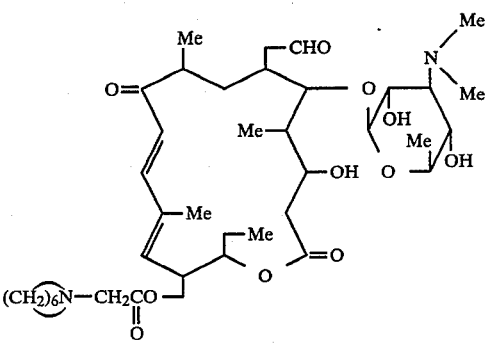

By following the same procedure as in Example 48-(b) using 400 mg of 23-O-chloroacetyl-2',4'-di-O-acetylmycaminosyl tylonolide diethylacetal and 97 mg of hexamethyleneimine, 96.9 mg of yellowish amorphous powder of 23-O-hexamethyleneiminoacetylmycaminosyl tylonolide was obtained.

(i) NMR (CDCl₃) δ(ppm):

1.84 (3H, s, H$_{22}$), 2.52 (6H, s, NMe$_2$), 3.43 (2H, s, COCH$_2$N 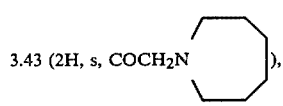), 4.10–4.40 (3H, m, H$_{11}$, —CH$_2$OCOCH$_2$N ), 4.98 (1H, m, H$_{15}$), 5.82 (1H, d, H$_{13}$), 6.32 (1H, d, H$_{10}$),
7.33 (1H, d, H$_{11}$), 9.73 (1H, s, —CHO).

(ii) IR (KBr) (cm⁻¹):
3420, 2950, 2910, 2860, 1715, 1670, 1620, 1585.

(iii) Mass (m/z):
736 (M⁺), 718 (M⁺ −18), 639 (M⁺ −97),
592 (M⁺ −144), 562 (M⁺ −174), 546 (M⁺ −190).

EXAMPLE 50

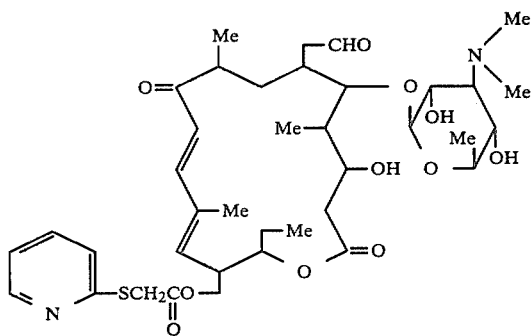

In 10 ml of acetonitrile was dissolved 65.3 mg of 2-mercaptopyridine and then 28.3 mg of 50% sodium hydride was added to the solution. When the generation of hydrogen stopped, 400 mg of 23-O-chloroacetyl-2',4'-di-O-acetylmycaminosyl tylonolide diethylacetal was added to the mixture at room temperature and the resultant mixture was stirred for one hour. Then, acetonitrile was distilled off under reduced pressure, the reisdue was dissolved in 50 ml of benzene, the solution thus formed was washed with 20 ml of a saturated aqueous sodium hydrogencarbonate solution, 20 ml of water, and then 20 ml of a saturated aqueous sodium chloride solution and dried by anhydrous magnesium sulfate, and then benzene was distilled off under reduced pressure. The residue was dissolved in 15 ml of methanol and after allowing to stand the solution for 20 hours at room temperature, methanol was distilled off under reduced pressure. The residue was dissolved in a mixture of 7 ml of acetonitrile and 14 ml of 0.1N hydrochloric acid and the solution was allowed to stand for 22 hours at room temperature, alkalified by the addition of sodium hydrogencarbonate, and extracted three times each time with 20 ml of chloroform. The extract was washed with 20 ml of water and then 20 ml of a saturated aqueous sodium chloride solution, dried by anhydrous magnesium sulfate, and then chloroform was distilled off under reduced pressure to provide a black-brown caramel. The product was purified by column chromatography using 50 ml of silica gel and eluate consisting of chloroform, methanol, and concentrated aqueous ammonia (15:1:0.1) to provide a yellowish amorphous powder of 23-O-(pyridine-2-thioyl)acetyl-mycaminosyl tylonolide.

(i) NMR (CDCl₃) δ(ppm):
1.79 (3H, s, H$_{22}$), 2.52 (6H, s, NMe$_2$), 4.00 (2H, s, OCOCH$_2$S—),
4.10–4.40 (3H, m, H$_{1'}$, —CH$_2$OCO—), 4.93 (1H, m, H$_{15}$),
5.66 (1H, d, H$_{13}$), 6.28 (1H, d, H$_{10}$), 7.20 (1H, d, H$_{11}$), 6.90–7.40 (2H, s, 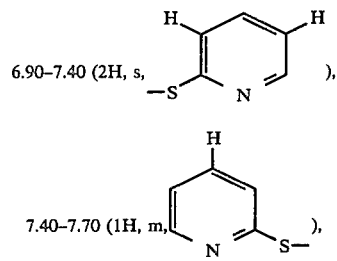 ), 7.40–7.70 (1H, m, ), 8.30–8.50 (1H, m, 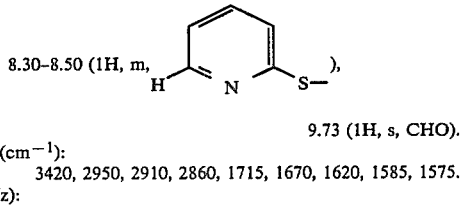 ), 9.73 (1H, s, CHO).

(ii) IR (KBr) (cm⁻¹):
3420, 2950, 2910, 2860, 1715, 1670, 1620, 1585, 1575.

(iii) Mass (m/z):
748 (M⁺), 637 (M⁺ −111), 597 (M⁺ −151), 558 (M⁺ −190).

EXAMPLE 51

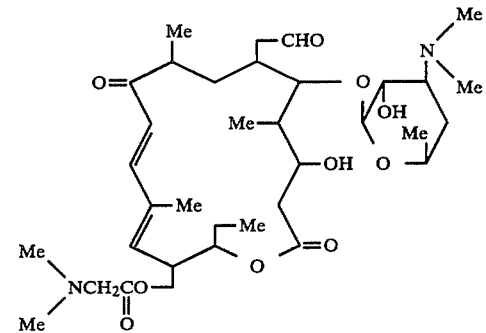

In 20 ml of anhydrous pyridine was dissolved 2 g of 2'-O-acetyl-4'-deoxymycaminosyl tylonolide diethylacetal and after cooling the solution to −20° C. and adding gradually 648.5 mg of chloroacetyl chloride to the solution, the mixture was stirred for 2 hours at the same temperature as above. The reaction mixture was added to 100 ml of a saturated aqueous sodium hydrogencarbonate solution and extracted twice each time with 100 ml of benzene. The extract was washed with 100 ml of water and then 100 ml of a saturated aqueous sodium chloride solution, dried by anhydrous magnesium sulfate, and then benzene was distilled off under reduced pressure.

The black-brown oil thus obtained was purified by column chromatography using 300 ml of silica gel and an eluate consisting of benzene and acetone (2:1) to provide 1.56 g of a yellow-brown amorphous powder of 23-O-chloroacetyl-2'-O-acetyl-4'-deoxymycaminosyl tylonolide diethylacetal.

In 40 mg of acetonitrile was dissolved 1.5 g of the foregoing product and after adding thereto 349 mg of dimethylamine, the mixture was stirred for 2 hours at room temperature. Acetonitrile was distilled off under reduced pressure, the residue was dissolved in 200 ml of benzene, and the solution was washed with 100 ml of a saturated aqueous sodium hydrogencarbonate solution, 100 ml of water, then 100 ml of a saturated aqueous sodium chloride solution and dried by anhydrous magnesium sulfate, and then benzene was distilled off under reduced pressure. The residue thus obtained was purified by column chromatography using 200 ml of silica gel and an eluate consisting of benzene and acetone (3:2) to provide 900 mg of a yellow-brown amorphous powder.

In 30 ml of methanol was dissolved 850 mg of the powder thus obtained and after allowing to stand overnight the solution at room temperature, methanol was distilled off under reduced pressure. The residue was dissolved in a mixture of 32 ml of 0.1N hydrochloric acid and 16 ml of acetonitrile and the solution was allowed to stand for 2 hours at room temperature, alkalified by the addition of sodium hydrogencarbonate, and then extracted three times each time with 50 ml of chloroform. The chloroform extracts were combined with each other, washed with 50 ml of water and then 50 ml of a saturated sodium chloride solution, and dried by anhydrous magnesium sulfate. Then, chloroform was distilled off under reduced pressure and the residue was purified by column chromatography using 150 ml of silica gel and an eluate consisting of chloroform, methanol, and concentrated aqueous ammonia (15:1:0.1) to provide 620 mg of yellowish amorphous powder of 23-O-dimethylaminoacetyl-4'-deoxymycaminosyl tylonolide.

---

(i) NMR (CDCl$_3$) δ(ppm):

1.77 (3H, s, H$_{22}$), 2.24 (6H, s, OCOCH$_2$NMe$_2$), 2.32 (6H, s, —NMe$_2$), 3.16 (2H, s, —OCOCH$_2$N⟨ ), 4.08–4.30 (3H, m, H$_{1'}$, —CH$_2$OCOCH$_2$N⟨ ), 4.90 (1H, m, H$_{15}$), 5.77 (1H, d, H$_{13}$), 6.28 (1H, d, H$_{10}$), 7.29 (1H, d, H$_{11}$), 9,68 (1H, s, —CHO)

(ii) IR (KBr) (cm$^{-1}$):

3440, 2950, 2920, 2860, 1720, 1670, 1620, 1585.

(iii) Mass (m/z):

666 (M$^+$), 623 (M$^+$ −43), 538 (M$^+$ −128), 492 (M$^+$ −174).

EXAMPLE 52

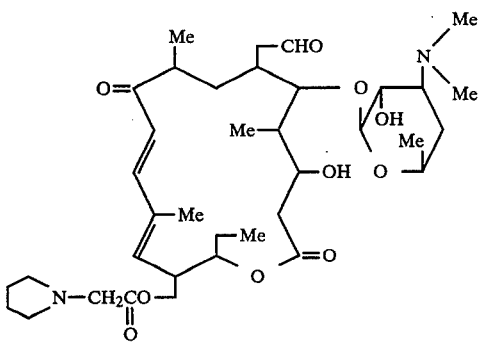

In 20 ml of acetonitrile was dissolved 773.5 mg of 23-O-chloroacetyl-2'-O-acetyl-4'-deoxymycaminosyl tylonolide diethylacetal obtained in Example 51 as an intermediate and after adding thereto 284 mg of pyrrolidine at room temperature, the mixture was stirred for 3 hours. Acetonitrile was distilled off under reduced pressure, the residue was dissolved in 70 ml of chloroform, the solution was washed with 30 ml of a saturated aqueous sodium hydrogencarbonate solution and then 20 ml of water and dried by anhydrous magnesium sulfate, and then chloroform was distilled off under reduced pressure. The residue was dissolved in 36 ml of methanol and after allowing to stand the solution for 20 hours at room temperature, methanol was distilled off under reduced pressure. The residue was dissolved in a mixture of 30 ml of 0.1N hydrochloric acid and 15 ml of acetonitrile, the solution was allowed to stand for 2 hours at room temperature, alkalified by the addition of sodium hydrogencarbonate, and extracted thrice each time with 20 ml of chloroform. The extracts were combined with each other, washed with 20 ml of water and then 20 ml of a saturated aqueous sodium chloride solution and dried by anhydrous magnesium sulfate. Chloroform was distilled off under reduced pressure and the residue was purified by column chromatography using 150 ml of silica gel and an eluate consisting of chloroform, methanol, and concentrated aqueous ammonia (14:1:0.1) to provide 220 mg of yellowish amorphous powder of 23-O-pyrrolidinoacetyl-4'-deoxymycaminosyl tylonolide.

---

(i) NMR (CDCl$_3$) δ(ppm):

1.80 (3H, s, H$_{22}$), 2.27 (6H, s, —NMe$_2$), 3.6 (2H, s, OCOCH$_2$N⟩ ), 4.10–4.40 (2H, m, H$_{1'}$,

—CH$_2$OCOCH$_2$N⟩ ), 4.94 (1H, m, H$_{15}$), 5.83 (1H, d, H$_{13}$), 6.33 (1H, d, H$_{10}$), 7.33 (1H, d, H$_{11}$), 9.74 (1H, s, CHO).

(ii) IR (KBr) (cm$^{-1}$):

3430, 2950, 2920, 2860, 1720, 1670, 1620, 1585.

(iii) Mass (m/z):

692 (M$^+$), 622 (M$^+$ −70), 563 (M$^+$ −129),

EXAMPLE 53

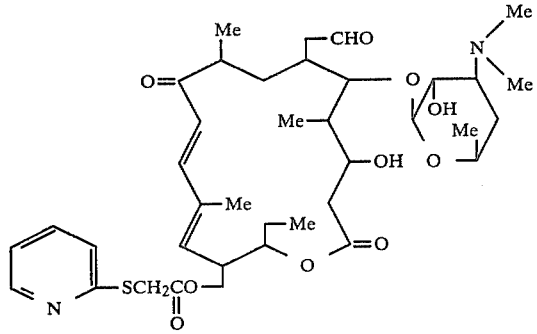

By following the same procedure as in Example 50 using 1 g of 23-O-chloroacetyl-2'-O-acetyl-4'-deoxymycaminosyl tylonolide diethylacetal obtained in Example 51 as an intermediate and 174 mg of 2-mercaptopyridine, 311.8 mg of a lemmon yellow amorphous powder of 23-O-(pyridine-2-thioyl)acetyl-4'-deoxymycaminosyl tylonolide.

(i) NMR (CDCl$_3$) δ(ppm):

1.74 (3H, s, H$_{22}$), 2.28 (6H, s, —NMe$_2$), 3.97 (2H, s, —OCOCH$_2$S—), 4.10–4.30 (3H, m, H$_{1'}$, —CH$_2$OCOCH$_2$S—), 4.93 (1H, m, H$_{15}$), 5.66 (1H, d, H$_{13}$), 6.26 (1H, d, H$_{10}$), 7.20 (1H, d, H$_{11}$), 6.90–7.30 (2H, m, 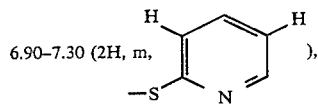 ), 7.40–7.70 (1H, m, 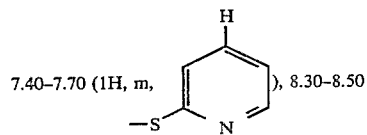 ), 8.30–8.50

(1H, m, 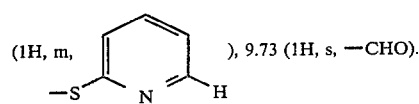 ), 9.73 (1H, s, —CHO).

(ii) IR (KBr) (cm$^{-1}$):

3430, 2950, 2920, 2860, 1720, 1670, 1620, 1585, 1575.

(iii) Mass (m/z):

732 (M$^+$), 714 (M$^+$ −18), 621 (M$^+$ −111), 558 (M$^+$ −174).

533 (M$^+$ −158), 517 (M$^+$ −174).

EXAMPLE 54

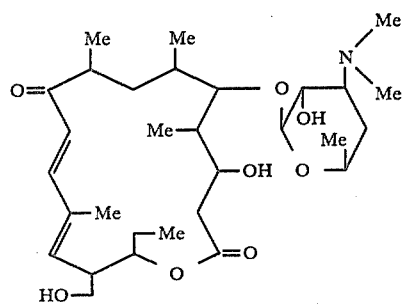

In 8.6 ml of anhydrous benzene was dissolved 344 mg of 4'-deoxymycaminosyl tylonolide and after suspending therein chlorotris(triphenylphosphin)rhodium in nitrogen stream, the suspension was heated at 80° C. for 12 hours with stirring. The reaction mixture was filtered and the filtrate was extracted three times each time with 9 ml of 1N hydrochloric acid and further an aqueous layer was alkalified with an 10% aqueous sodium hydroxide solution and extracted thrice each time with 10 ml of chloroform. The chloroform layers were combined with each other, washed three times each time with 10 ml of a saturated aqueous sodium sulfate solution and after drying with anhydrous sodium sulfate, the solvent was distilled off. The residue was purified by a silica gel column using a solvent system of chloroform and methanol (10:1) to provide 166.1 mg (yield 51%) of 19-decarbonyl-4'-deoxymycaminosyl tylonolide.

(Recrystallized from acetone-n-hexane)

(i) NMR (CDCl$_3$)

| δ(ppm) | H number | Form | J(Hz) | |
|---|---|---|---|---|
| 1.83 | 3 | s | | H$_{21}$ |
| 2.31 | 6 | s | | 3'-NMe$_2$ |
| 4.27 | 1 | d$_{1', 2'}$ | d | H$_{1'}$ |
| 5.02 | 1 | m | | H$_{15}$ |
| 6.37 | 1 | d$_{10, 11}$ | 16.0 | H$_{10}$ |
| 7.36 | 1 | d$_{11, 10}$ | 16.0 | H$_{11}$ |

(aldehyde proton in starting material lost).

(ii) IR (KBr) (cm$^{-1}$):

| | |
|---|---|
| 2970 | —CH$_3$ |
| 2940 | —CH$_2$— |
| 1700 | —COO— |
| 1675 | $\diagdown$C=O$\diagup$ |
| 1590 | —C=C—C=C— |

(iii) Colorless prism crystal (iv) m.p.: 181–183° C.

(v) Anal. for C$_{30}$H$_{51}$NO$_8$·H$_2$O:

| | C (%) | H (%) | N (%) |
|---|---|---|---|
| Calculated: | 63.02 | 9.34 | 2.45 |
| Found: | 62.95 | 9.14 | 2.34 |

(vi) [α]$_D^{25}$ +35° (c 1.0, CHCl$_3$)

(vii) UV λ$_{max}^{MeOH}$ 282 nm (ε = 23,000)

EXAMPLE 55

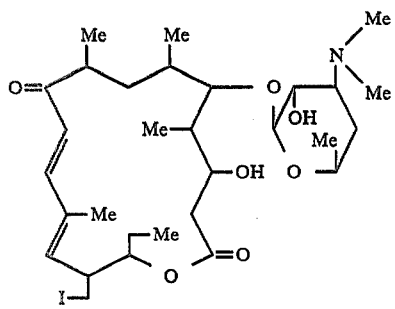

In 4.4 ml of anhydrous pyridine was dissolved 88.7 mg of 19-decarbonyl-4'-deoxymycaminosyl tylonolide obtained in Example 54, 92.2 mg of triphenylphosphin was added to the solution, and after adding thereto 91.3 mg of carbon tetraiodide with stirring under ice-cooling, the mixture was stirred for 90 minutes under ice-cooling. After stopping the reaction by adding 0.06 ml of methanol to the reaction mixture, the solvent was distilled off. (Pyridine was removed by azeotropically distilling several times with toluene). The residue was dissolved in chloroform, the insoluble materials were filtered off, the chloroform layer was washed once with a saturated aqueous sodium hydrogencarbonate solution, a 0.1M aqueous sodium thiosulfate solution, and then a saturated aqueous sodium sulfate solution, and dried by anhydrous sodium sulfate, and then the solvent was distilled off. The residue was purified by a silica gel column chromatography using a solvent system of chloroform and methanol to provide 94.4 mg (yield 89%) of 19-decarbonyl-22,4'-dideoxy-22-iodomycaminosyl tylonolide.

(Recrystallized from acetone-n-hexane).

| (i) | NMR (CDCl$_3$) | | | |
|---|---|---|---|---|
| | δ(ppm) | H number | Form | J(Hz) | |
| | 1.83 | 3 | s | | H$_{21}$(12-CH$_3$) |
| | 2.32 | 6 | s | | 3'-NMe$_2$ |
| | 4.27 | 1 | d$_{1',2'}$ | 7.5 | H$_{2'}$ |
| | 4.88 | 1 | m | | H$_{15}$ |
| | 5.71 | 1 | d$_{13,14}$ | 10.0 | H$_{13}$ |
| | 6.41 | 1 | d$_{11,10}$ | 16.0 | H$_{10}$ |
| | 7.38 | 1 | d$_{11,10}$ | 16.0 | H$_{11}$ |
| (ii) | IR (KBr) (cm$^{-1}$): | | | |
| | 2970 | | —CH$_3$ | |
| | 2940 | | —CH$_2$— | |
| | 1710 | | —COO— | |
| | 1680 | | $\diagdown$C=O$\diagup$ | |
| | 1590 | | —C=C—C=C— | |
| (iii) | Colorless acicular crystal | | | |
| (iv) | Melting point: 209–210° C. | | | |
| (v) | Anal. for C$_{30}$H$_{50}$NO$_7$I: | | | |

| | C (%) | H (%) | N (%) | I (%) |
|---|---|---|---|---|
| Calculated: | 54.30 | 7.59 | 2.11 | 19.12 |
| Found: | 54.58 | 7.51 | 2.31 | 19.25 |

(ii) $[\alpha]_D^{25} + 97°$ (c 1.0, CHCl$_3$)

(vii) UV $\lambda_{max}^{MeOH}$ 282 nm (ε = 24,000)

EXAMPLE 56

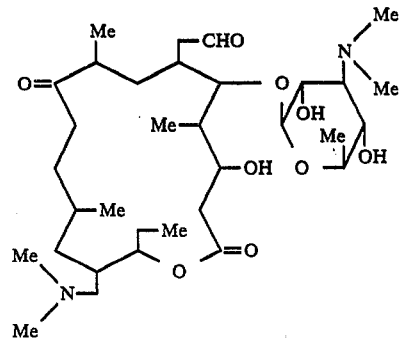

In 10 ml of ethanol was dissolved 499 mg of mycaminosyl tylonolide diethylacetal and after displacing the atmosphere of the reaction system with nitrogen, platinum black was added to the reaction system to perform the reaction while blowing hydrogen into the reaction system for 3 hours. The reaction mixture was filtered to remove platinum black and the filtrate was concentrated under reduced pressure. The residue was subjected to chromatography using a column filled with 60 g of silica gel by chloroform-methanol (50:1) using a solvent system of chloroform-methanol (6:1) to provide 499.7 mg (99.5%) of 10,11,12,13-tetrahydromycaminosyl tylonolide diethylacetal.

In 25 ml of anhydrous pyridine was dissolved the foregoing product and then 493.2 mg of triphenylphosphin was completely dissolved in the solution. After ice-cooling the solution, 459.3 mg of carbon tetrachloride was added to the solution with stirring in a nitrogen stream to perform the reaction for 30 minutes. Then, the reaction system was allowed to stand for raising the temperature to room temperature and the reaction was further continued for 60 minutes. After stopping the reaction by adding thereto 5.5 ml of methanol under ice-cooling, the reaction mixture was concentrated under reduced pressure and the residue was azeotropically distilled with toluene. The product was dissolved in 25 ml of ethyl acetate and the solution was filtered by glass wool filter. The filtrate was washed with 8 ml of a saturated aqueous sodium hydrogencarbonate solution, a 0.1M aqueous sodium thiosulfate solution, and then a saturated aqueous sodium sulfate solution and then the ethyl acetate layer was dried with anhydrous sodium sulfate and concentrated under reduced pressure.

The residue was subjected to chromatographic treatment by charging it in a column filled with 5 g of silica gel by chloroform-methanol (50:1) with the same solvent system using a solvent system of chloroform-methanol (6:1) to provide 436.9 mg (yield 75.2%) of 23-deoxy-23-iodo-10,11,12,13-tetrahydromycaminosyl tylonolide diethylacetal.

In 2.25 ml of anhydrous acetonitrile was dissolved 112.7 mg of the product obtained in the foregoing step and after adding thereto 0.3 ml of 4.9M dimethylamine, the mixture was heated at 80° C. for 30 minutes. Then, 0.3 ml of 4.9M dimethylamine was added again to the mixture and the resultant mixture was further heated for 90 minutes. The reaction mixture was concentrated to remove acetonitrile and the residue was azeotropically distilled off with chloroform.

The product was dissolved in 10 ml of chloroform and the solution was washed once with 1 ml of a saturated aqueous sodium hydrogencarbonate solution and then twice each time with a saturated aqueous sodium sulfate solution, dried with anhydrous sodium sulfate, and then concentrated under reduced pressure. Thereafter, 100.8 mg (theoretical amount) of the residue (i.e., 23-deoxy-23-dimethylamino-10,11,12,13-tetrahydromycaminosyl tylonolide diethylacetal was dissolved in 2 ml of acetonitrile and after adding thereto 5.8 ml of 0.1N hydrochloric acid, the reaction was performed for 90 minutes. The reaction mixture was neutralized by the addition of 62.1 mg of sodium hydrogencarbonate and 0.8 ml of a saturated aqueous sodium hydrogencarbonate solution and then extracted three times each time with 2 ml of chloroform. The chloroform layers were combined with each other, washed twice each time with 2 ml of a saturated aqueous sodium sulfate solution, dried with anhydrous sodium sulfate, and concentrated under reduced pressure. The residue was subjected to chromatographic treatment by a column filled with chloroform-methanol-concentrated aqueous ammonia (30:1:0.1) using a solvent system of chloroform-methanol, and concentrated aqueous ammonia (12:1:0.1) to provide 73.3 mg (yield 81.3%) of 23-deoxy-23-dimethylamino-10,11,12,13-tetrahydromycaminosyl tylonolide.

| (i) | NMR (CDCl₃): | | | |
|---|---|---|---|---|
| | δ(ppm) | H number | Form | J(Hz) | |
| | 2.18 | 6 | s | | 23-NMe₂ |
| | 2.51 | 6 | s | | 3'-NMe₂ |
| | 4.31 | 1 | d₁', ₂' | 7.5 | H₁' |
| | 5.09 | 1 | | | H₁₅ |
| | 9.74 | 1 | s | | H₂₀ |
| (ii) | IR (KBr) (cm⁻¹): | | | |
| | 2970 | | | —CH₃ |
| | 2940 | | | —CH₂— |
| | 1720 | | | —CHO |
| | 1710 | | | \CO/ |

EXAMPLE 57

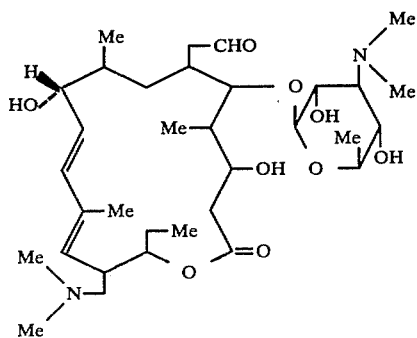

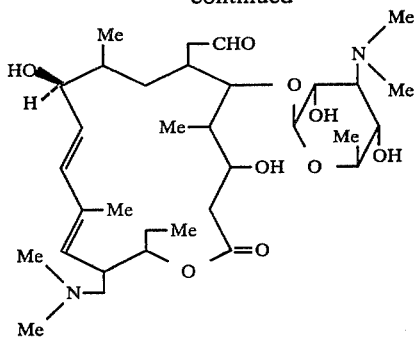

-continued (a) In 0.8 ml of methanol was dissolved 80.9 mg of 23-deoxy-23-dimethylaminomycaminosyl tylonolide diethylacetal and after ice-cooling the solution and adding thereto 13.2 mg of sodium borohydride, the reaction was performed under ice-cooling. After continuing the reaction for 3 hours and 30 minutes, 4.5 mg of sodium borohydride was added again to the reaction system and the reaction was further continued. Then, for decomposing excessive sodium borohydride, 1.5 ml of acetone was added to the reaction mixture, the mixture was concentrated under reduced pressure, the residue was dissolved in chloroform, and after filtering the solution, the solution was concentrated again under reduced pressure. The residue was dissolved in 10 ml of chloroform and the solution was washed twice each time with 2 ml of a saturated aqueous sodium sulfate solution. Then, the solution was charged into a column, in which 8 g of silica gel had been filled with chloroform-methanol-concentrated aqueous ammonia (30:1:0.1), using the solvent having the same composition as above and chromatographically treated with a solvent system of chloroform-methanol-concentrated aqueous ammonia (15:1:0.1) to provide 29.2 mg of 9-deoxo-(9R)-hydroxy-23-deoxy-23-dimethylaminomycaminosyl tylonolide diethylacetal and 30.7 mg of 9-deoxo-(9S)-hydroxy-23-deoxy-23-dimethylaminomycaminosyl tylonolide diethylacetal.

In addition, the former was obtained by filtering in hot state by the addition of acetone and recrystallized from n-hexane and the latter was obtained by reprecipitating from acetone-n-hexane.

(Yield: 76.7% for both products)

(b)-1. In 0.59 ml of acetonitrile was dissolved 29.2 mg of 9-deoxo-(9R)-hydroxy-23-deoxy-23-dimethylaminomycaminosyl tylonolide diethylacetal and after adding thereto 1.25 ml of 0.1N hydrochloric acid at room temperature, the reaction was performed for 90 minutes. The reaction mixture was neutralized by the addition of 16.6 mg of sodium hydrogencarbonate and 0.5 ml of a saturated aqueous sodium hydrogencarbonate solution, and extracted three times each time with 2 ml of chloroform. The chloroform layers were combined with each other, washed twice each time with 2 ml of a saturated aqueous sodium sulfate solution, dried by anhydrous sodium sulfate, and then concentrated under reduced pressure. The residue was charged into a column, in which 3 g of silica gel had been filled with chloroform-methanol-concentrated aqueous ammonia (30:1:0.1), by the solvent having the same composition as above and chromatographically treated with a solvent system of chloroform-methanol-concentrated aqueous ammonia (12:1:0.1) to provide 24.8 mg (yield 94.9%) of 9-deoxo-(9R)-hydroxy-23-deoxy-23-dimethylaminomycaminosyl tylonolide (Compound A).

Then, the product was re-precipitated from acetone-n-hexane. The reprecipitated amount was 23.0 mg.

(i) NMR (CDCl$_3$):

| δ(ppm) | H number | Form | J(Hz) | |
|---|---|---|---|---|
| 1.79 | 3 | s | | H$_{22}$(12-Me) |
| 2.20 | 6 | s | | 23-NMe$_2$ |
| 2.52 | 1 | s | | 3'-NMe$_2$ |
| 4.20 | 1 | 9,8 | 4 | |
| | | dd$_{9,10}$ | 8 | |
| 4.37 | 1 | d$_{1',2'}$ | 7.5 | H$_{1'}$ |
| 4.75 | 1 | m | | H$_{15}$ |
| 5.25 | 1 | d$_{13,14}$ | 10.0 | H$_{13}$ |
| 5.69 | 1 | 10,9 | 8 | H$_{10}$ |
| | | dd$_{10,11}$ | 16.0 | |
| 6.25 | 1 | d$_{11,10}$ | 16.0 | H$_{11}$ |
| 9.85 | 1 | s | | H$_{20}$ |

(ii) IR (KBr) (cm$^{-1}$):

| | |
|---|---|
| 2970 | —CH$_3$ |
| 2940 | —CH$_2$— |
| 1720 | —CHO |

(iii) Colorless amorphous solid (iv) Anal. for C$_{33}$H$_{58}$N$_2$O$_9$:

| | C (%) | H (%) | N (%) |
|---|---|---|---|
| Calculated: | 63.23 | 9.33 | 4.47 |
| Found: | 63.93 | 9.25 | 4.61 |

(v) $[\alpha]_D^{22.6} + 56°$ (c 1.0, CHCl$_3$)
(vi) UV $\lambda_{max}^{MeOH}$ 237.5 nm ($\epsilon = 25,000$)
(vii) Rf 0.18 Wako gel B-5 chloroform-methanol (6:1)

(b)-2. In 0.62 ml of acetonitrile was dissolved 30.7 mg of 9-deoxo-(9S)-hydroxy-23-deoxy-23-dimethylaminomycaminosyl tylonolide diethylacetal and after adding thereto 1.3 ml of 0.1N hydrochloric acid at room temperature, the reaction was performed for 90 minutes. The reaction mixture was neutralized by the addition of 158 mg of sodium hydrogencarbonate and 0.5 ml of a saturated aqueous sodium hydrogencarbonate solution and extracted three times each time with 1.5 ml of chloroform. The chloroform layers were combined with each other, washed twice each time with a saturated aqueous sodium sulfate solution, dried with anhydrous sodium sulfate, and then concentrated under reduced pressure. The residue was charged into a column, in which 3.5 g of silica gel had been packed by chloroform-methanol-concentrated aqueous ammonia (30:1:0.1), with the solvent having the same composition as above and chromatographically treated by a solvent system of chloroform-methanol-concentrated aqueous ammonia (12:1:0.1) to provide 27.4 mg (yield 99.6%) of 9-deoxo-(9S)-hydroxy-23-deoxy-23-dimethylaminomycaminosyl tylonolide (Compound B).

(i) NMR (CDCl$_3$):

| δ(ppm) | H number | Form | J(Hz) | |
|---|---|---|---|---|
| 1.77 | 3 | s | | H$_{22}$(12-Me) |
| 2.18 | 6 | s | | 23-NMe$_2$ |
| 2.50 | 6 | s | | 3'-NMe$_2$ |
| 4.38 | 1 | d$_{1',2'}$ | 7.5 | H$_{1'}$ |
| 4.72 | 1 | m | | H$_{15}$ |
| 5.27 | 1 | d$_{13,14}$ | 10.0 | H$_{13}$ |
| 5.90 | 1 | 10,9 | 4 | H$_{10}$ |
| | | dd$_{10,11}$ | 16.0 | |
| 6.53 | 1 | d$_{11,10}$ | 16.0 | H$_{11}$ |
| 9.81 | 1 | s | | H$_{20}$ |

(ii) IR (KBr) (cm$^{-1}$):

| | |
|---|---|
| 2070 | —CH$_3$ |
| 2940 | —CH$_2$— |
| 1720 | —COO—, —CHO |

(iii) Colorless amorphous solid (reprecipitated from acetone-n-hexane)

(iv) Anal. for C$_{33}$H$_{58}$N$_2$O$_9$:

-continued

| | C (%) | H (%) | N (%) |
|---|---|---|---|
| Calculated | 63.23 | 9.33 | 4.47 |
| Found: | 63.10 | 9.41 | 4.52 |

(v) $[\alpha]_D^{23} + 60°$(c 1.0, CHCl$_3$)
(vi) UV $\lambda_{max}^{MeOH}$ 237 nm ($\epsilon = 25,000$)
(vii) Rf 0.48 Wako gel B-5 chloroform-methanol-concentrated

EXAMPLE 58

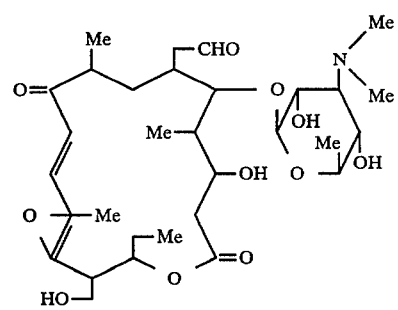

In 10 ml of chloroform was dissolved in 1.08 g of mycaminosyl tylonolide diethylacetal and then 8.4 ml of a chloroform solution containing 840 mg of m-chloroperbenzoic acid was added dropwise to the solution under ice-cooling over a period of 15 minutes. After allowing to raise the temperature thereof to room temperature, the mixture was allowed to stand for 24 hours. The mixture was washed once with an 10% aqueous sodium sulfite solution, a saturated aqueous sodium hydrogencarbonate solution, and then a saturated aqueous sodium sulfate solution, and then dried with anhydrous sodium sulfate. The solvent was distilled off and the residue thus obtained was dissolved in 20 ml of ethyl acetate. Then, after adding 634 mg of triphenylphosphin to the solution, the mixture was refluxed in argon stream for 6 hours. The reaction mixture was washed once with a saturated aqueous sodium hydrogencarbonate solution and then a saturated aqueous sodium sulfate solution and dried with anhydrous sodium sulfate. The solvent was distilled off and the residue thus obtained was subjected to chromatographic treatment on 50 g of a silica gel column using a solvent system of chloroform-methanol-28% aqueous ammonia (15:1:0.1) to provide 820 mg of 12,13-epoxymycaminosyl tylonolide diethylacetal.

In 4.1 ml of acetonitrile was dissolved the foregoing product and after adding thereto 24 ml of 0.1N hydrochloric acid, the mixture was allowed to stand for 60 minutes. Then, 240 mg of sodium hydrogencarbonate was added to the reaction mixture and the mixture was extracted three times each time with chloroform. The chloroform layers were combined with each other, washed with a saturated aqueous sodium sulfate solution, and dried by anhydrous sodium sulfate. The solvent was distilled and the residue thus obtained was purified by column chromatography on a column of 40 g of silica gel using a solvent system of chloroform-methanol-28% aqueous ammonia (10:1:0.1) to provide 617 mg (yield 63%) of a colorless solid of 12,13-epoxymycaminosyl tylonolide.

(i) NMR (CDCl$_3$):

-continued

| | δ(ppm) | H number | Form | J(Hz) | |
|---|---|---|---|---|---|
| | 1.45 | 3 | s | | Me(22) |
| | 2.50 | 6 | s | | $NMe_2$ |
| | 4.30 | 1 | $d_{1', 2'}$ | 7.5 | $H_{1'}$ |
| | 5.26 | 1 | m | | $H_{15}$ |
| | 6.44 | 1 | $d_{10, 11}$ | 16 | $H_{10}$ |
| | 6.64 | 1 | $d_{11, 10}$ | | $H_{11}$ |
| | 9.72 | 1 | s | | $H_{20}$ |
| (ii) | Mass (m/z): 613 (M+) | | | | |
| (iii) | IR (KBr) ($cm^{-1}$): | | | | |
| | 2970 | | | | $-CH_3$ |
| | 2940 | | | | $-CH_2-$ |
| | 1720 | | | | $-COO-, -CHO$ |
| | 1620 | | | | $\underset{\underset{O}{\parallel}}{-C}-C=C-$ |

(iv) Anal. for $C_{31}H_{51}NO_{11}$:

| | C (%) | H (%) | N (%) |
|---|---|---|---|
| Calculated: | 60.67 | 8.38 | 2.28 |
| Found: | 60.32 | 8.24 | 2.26 |

EXAMPLE 59

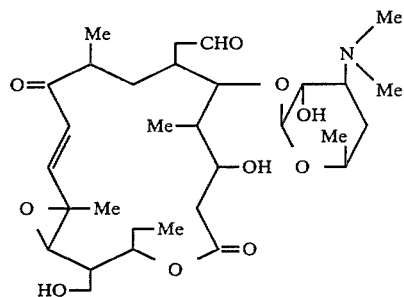

By following the same procedure as in Example 58 using 1.03 g of 4'-deoxymycaminosyl tylonolide diethylacetal, 572 mg (yield 61%) of 12,13-epoxy-4'-deoxymycaminosyl tylonolide was obtained.

| | NMR ($CDCl_3$): | | | | |
|---|---|---|---|---|---|
| (i) | δ(ppm) | H number | Form | J(Hz) | |
| | 1.45 | 3 | s | | Me(22) |
| | 2.28 | 6 | s | | $NMe_2$ |
| | 4.26 | 1 | $d_{1', 2'}$ | 7.5 | $H_{1'}$ |
| | 5.27 | 1 | m | | $H_{15}$ |
| | 6.44 | 1 | $d_{10, 11}$ | 16 | $H_{10}$ |
| | 6.64 | 1 | d | | $H_{11}$ |
| | 9.75 | 1 | s | | $H_{20}$ |
| (ii) | Mass (m/z): 597 (M+) | | | | |
| (iii) | IR (KBr) ($cm^{-1}$): | | | | |
| | 2970 | | | | $-CH_3$ |
| | 2940 | | | | $-CH_2-$ |
| | 1720 | | | | $-COO-, -CHO$ |
| | 1620 | | | | $-C-C=C-$ $\underset{O}{\parallel}$ |

(iv) Anal. for $C_{31}H_{51}NO_{10}$:

| | C (%) | H (%) | N (%) |
|---|---|---|---|
| Calculated: | 62.29 | 8.60 | 2.34 |
| Found: | 61.98 | 8.32 | 2.16 |

EXAMPLE 60

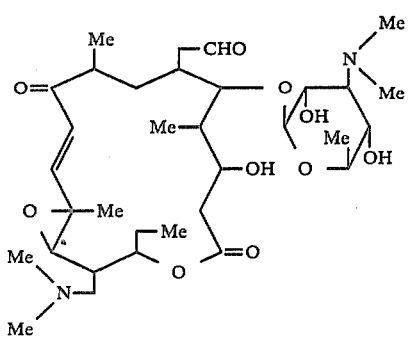

In 18 ml of chloroform was dissolved 1.83 g of 23-deoxy-23-dimethylaminomycaminosyl tylonolide diethylacetal and after adding thereto dropwise a chloroform solution (20 ml of chloroform) of 2.04 g of m-chloroperbenzoic acid under ice-cooling, the mixture was allowed to stand for 24 hours at room temperature. The solvent was distilled off and the residue thus obtained was dissolved in 17.6 ml of ethyl acetate. After adding thereto 3.09 g of triphenylphosphin, the mixture was refluxed for 2 hours in argon stream. The solvent was distilled off, the residue thus obtained was dissolved in a small amount of methanol, a large amount of water was added to the solution to form precipitates, which were filtered away. The filtrate was concentrated and the residue formed was dissolved in water. The solution was washed with toluene and after adding 0.1M sodium carbonate to the aqueous layer, the mixture was extracted three times each time with chloroform. The chloroform layers were combined with each other, washed with a saturated aqueous sodium sulfate solution, and dried by anhydrous sodium sulfate. The solvent was distilled off and the residue thus formed was chromatographically treated on a column of 50 g of silica gel using a solvent system of chloroform-methanol-28% aqueous ammonia (15:1:0.1) to provide 225 mg of 23-deoxy-23-dimethylamino-12,13-epoxymycaminosyl tylonolide diethylacetal. The product was dissolved in 2 ml of acetonitrile and after adding thereto 9.5 ml of 0.1N hydrochloric acid, the mixture was allowed to stand for 60 minutes. To the reaction mixture was added 0.1M sodium carbonate to form white turbidity (pH 9) and the product was extracted three times each time with chloroform. The chloroform layers were combined with each other, washed with a saturated aqueous sodium sulfate solution, and then dried with anhydrous sodium sulfate. The solvent distilled off and the residue thus obtained was chromatographically treated on a column of 20 g of silica gel using a solvent system of chloroform-methanol-28% aqueous ammonia (10:1:0.1) to provide 185 mg (yield 11%) of 23-deoxy-23-dimethylamino-12,13-epoxymycaminosyl tylonolide.

| (i) NMR ($CDCl_3$): | | | | |
|---|---|---|---|---|
| δ (ppm) | N number | Form | J (Hz) | |
| 1.46 | 3 | s | | Me (22) |
| 2.24 | 6 | s | | 23-$NMe_2$ |
| 2.50 | 6 | s | | 3'-$NMe_2$ |
| 3.30 | 1 | $d_{1',2'}$ | 7.5 | $H_{1'}$ |
| 5.03 | 1 | m | | $H_{15}$ |
| 6.41 | 1 | $d_{10,11}$ | 16 | $H_{10}$ |

EXAMPLE 61

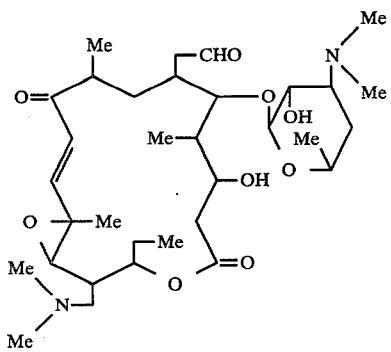

By following the same procedure as in Example 60 using 2.0 g of 23,4'-dideoxy-23-dimethylaminomycaminosyl tylonolide diethylacetal, 140 mg (yield 7.6%) of 23,4'-dideoxy-23-dimethylamino-12,13-epoxymycaminosyl tylonolide was obtained.

(i) NMR (CDCl$_3$):

| δ (ppm) | H number | Form | J (Hz) | |
|---|---|---|---|---|
| 1.41 | 3 | s | | Me (22) |
| 2.20 | 6 | s | | 23-NMe$_2$ |
| 2.24 | 6 | s | | 3'-NMe$_2$ |
| 4.22 | 1 | d$_{1',2'}$ | 7.5 | H$_{1'}$ |
| 4.99 | 1 | m | | H$_{15}$ |
| 6.36 | 1 | d$_{10,11}$ | 16 | H$_{10}$ |
| 6.58 | 1 | d$_{11,10}$ | | H$_{11}$ |
| 9.71 | 1 | s | | H$_{20}$ |

(i) Mass (m/z): 624(M$^+$)
(ii) High mass (m/z): 624.401(M$^+$) (calculated: 624.398)
(iii) IR (KBr) (cm$^{-1}$):

| 2970 | —CH$_3$ |
| 2940 | —CH$_2$— |
| 1720 | —COO—, —CHO |
| 1620 | —C—C=C—<br>‖<br>O |

(iv) Anal. for C$_{33}$H$_{56}$N$_2$O$_9$:

| | C (%) | H (%) | N (%) |
|---|---|---|---|
| Calculated: | 64.44 | 9.03 | 4.48 |
| Found: | 64.23 | 9.04 | 4.37 |

-continued

| 6.60 | 1 | d$_{11,10}$ | H$_{11}$ |
| 9.72 | 1 | s | H$_{20}$ |

(ii) Mass (m/z): 640(M$^+$)
(iii) IR (KBr) (cm$^{-1}$):

| 2970 | —CH$_3$ |
| 2940 | —CH$_2$— |
| 1720 | —COO—, —CHO |
| 1620 | —C—C=C—<br>‖<br>O |

(iv) Anal. for C$_{33}$H$_{56}$N$_2$O$_{10}$:

| | C (%) | H (%) | N (%) |
|---|---|---|---|
| Calculated: | 61.85 | 8.81 | 4.37 |
| Found: | 61.58 | 8.62 | 4.38 |

EXAMPLE 62

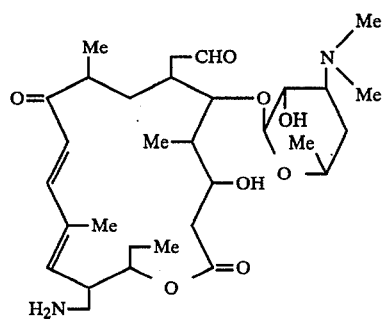

(a) In 20 ml of anhydrous dimethylformamide was dissolved 1.04 g of 23,4'-dideoxy-23-iodomycaminosyl tylonolide diethylacetal and after adding thereto 0.27 g of sodium azide, the mixture was heated at 80° C. for 6.5 hours with stirring. The reaction mixture was concentrated under reduced pressure and the residue was extracted with 50 ml of chloroform. The extract was washed with 20 ml of water, 20 ml of a saturated aqueous sodium hydrogencarbonate solution, and then 20 ml of a saturated aqueous sodium sulfate solution, dried with anhydrous sodium sulfate, and concentrated under reduced pressure. The residue was subjected by silica gel column chromatography using chloroform-methanol-28% aqueous ammonia (30:1:0.1) to provide 635 mg (yield 68.5%) of 23-azido-23,4'-dideoxymycaminosyl tylonolide diethylacetal.

(b) In 31 ml of acetone was dissolved 1.554 g of the foregoing product and 0 ml of an aqueous chromium chloride solution (1.43 m mol/ml) was added to the solution under ice-cooling in argon gas atmosphere, whereby the generation of nitrogen gas was observed. After 5 minutes, the reaction mixture was poured into 150 ml of a half saturated aqueous sodium hydrogencarbonate solution under ice-cooling. The reaction mixture was filtered to remove chromium salts. In addition, the chromium salts thus removed were sufficiently washed with chloroform. The filtrate was adjusted to a pH above 9 by the addition of a saturated aqueous sodium sulfate solution and extracted with chloroform. The chloroform extract was combined with the chloroform washings and the mixture was washed with a saturated aqueous sodium sulfate solution, dried by anhydrous sodium sulfate, and concentrated under reduced pressure. The residue was subjected to silica gel column chromatography using chloroform-methanol-28% aqueous ammonia (20:1:0.1) to provide 861.5 mg (yield 57.6%) of 23-amino-23,4'-dideoxymycaminosyl tylonolide diethylacetal.

(c) In 0.4 ml of acetonitrile was dissolved 20 mg of the foregoing product and after adding thereto 1.2 ml of 0.1N hydrochloric acid, the mixture was allowed to stand for one hour at room temperature. Then, 2 ml of a saturated aqueous sodium hydrogencarbonate solution was added to the reaction mixture and the product was extracted with 1.5 ml of chloroform. The extract was washed with 2 ml of a saturated sodium sulfate solution, dried with anhydrous sodium sulfate, and concentrated under reduced pressure to provide 16 mg (yield 90%) of 23-amino-23,4'-dideoxymycaminosyl tylonolide.

[α]$_D^{25}$+11° (c 1.0, CHCl$_3$)

EXAMPLE 63

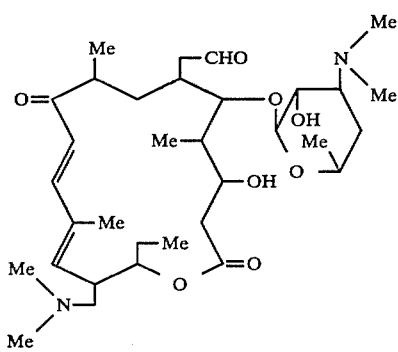

In 1.5 ml of anhydrous acetonitrile was dissolved 65 mg of 23-amino-23,4'-dideoxymycaminosyl tylonolide diethylacetal and after adding thereto 63 mg of methyl iodide, the mixture was heated at 80° C. for 6 hours. The reaction mixture was concentrated under reduced pressure and the residue was extracted with 3 ml of chloroform. The extract was washed twice each time with 2 ml of a satruated aqueous sodium hydrogencarbonate solution and then 2 ml of a saturated aqueous sodium sulfate solution, dried by anhydrous sodium sulfate, and concentrated under reduced pressure. The residue thus obtained was dissolved in 1.5 ml of acetonitrile and after adding thereto 4 ml of 0.1N hdyrochloric acid, the mixture was allowed to stand for one hour at room temperature. To the reaction mixture was added 3 ml of a saturated aqueous sodium hydrogencarbonate solution and then the reaction product was extracted with 3 ml of chloroform. The extract was washed with 3 ml of a saturated aqueous sodium sulfate solution, dried with anhydrous sodium sulfate, and concentrated under reduced pressure. The residue was subjected to silica gel column chromatography using chloroform-methanol-28% aqueous ammonia (18:1:0.1) to provide 10 mg (yield 18%) of 23,4'-dideoxy-23-dimethylaminomycaminosyl tylonolide.

(i) NMR (CDCl$_3$):

| δ(ppm) | H number | Form | J(Hz) | |
|---|---|---|---|---|
| 2.22 | 6 | s | | 23-NMe$_2$ |
| 2.31 | 6 | s | | 3'-NMe$_2$ |
| 4.23 | 1 | d$_{1',2'}$ | 7.5 | H$_{1'}$ |
| 4.78 | 1 | m | | H$_{15}$ |
| 9.83 | 1 | s | | H$_{20}$ |

(ii) Colorless amorphous solid (reprecipitated from acetone-n-hexane)

(iii) Anal. for C$_{31}$H$_{56}$N$_2$O$_9$:

| | C (%) | H (%) | N (%) |
|---|---|---|---|
| Calculated: | 65.10 | 9.27 | 4.60 |
| Found: | 66.21 | 9.16 | 4.37 |

(iv) $[\alpha]_D^{23}$ + 23° (c 1.0, CHCl$_3$)

EXAMPLE 64

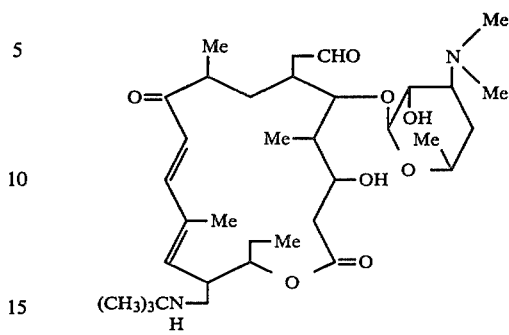

By following the same procedure as in Example 63 using 66 mg of 23-amino-23,4'-dideoxymycaminosyl tylonolide diethylacetal and 14 mg of tert-butyl bromide, 21 mg (yield 32%) of 23,4'-dideoxy-23-tert-butylaminomycaminosyl tylonolide was obtained.

(i) NMR (CDCl$_3$):

| δ(ppm) | H number | Form | J(Hz) | |
|---|---|---|---|---|
| 1.05 | 9 | s | | NHC(CH$_3$)$_3$ |
| 1.80 | 3 | s | | Me(22) |
| 2.24 | 6 | s | | NMe$_2$ |
| 4.20 | 1 | d$_{1',2'}$ | 7.5 | H$_{1'}$ |
| 4.82 | 1 | m | | H$_{15}$ |
| 5.64 | 1 | d$_{13,14}$ | 10 | H$_{13}$ |
| 6.31 | 1 | d$_{10,11}$ | 16 | H$_{10}$ |
| 7.34 | 1 | d | | H$_{11}$ |
| 9.72 | 1 | s | | H$_{20}$ |

(ii) Anal. for C$_{35}$H$_{60}$N$_2$O$_8$:

| | C (%) | H (%) | N (%) |
|---|---|---|---|
| Calculated: | 66.01 | 9.50 | 4.40 |
| Found: | 65.82 | 9.41 | 4.65 |

(iii) Mass (m/z):
636(M$^+$), 551, 507, 462, 174, 158, 98, 86

(iv) IR (KBr) (cm$^{-1}$):
2970, 2940, 1720, 1680, 1596.

EXAMPLE 65

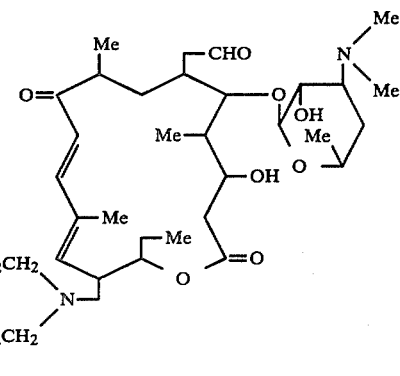

In 1.7 ml of acetonitrile was dissolved 86.8 mg of 23,4'-dideoxy-23-iodomycaminosyl tylonolide diethylacetal and after adding thereto 0.12 g of diethanolamine, the mixture was heated at 80° C. for 10.5 hours. The reaction mixture was concentrated, the residue was extracted with 6 ml of chloroform, and the extract was washed twice each time with 2 ml of a saturated aqueous sodium hydrogencarbonate solution and then twice each time with 2 ml of a saturated sodium sulfate solution, dried by anhydrous sodium sulfate, and concentrated under reduced pressure. The residue was washed with n-hexane, solidified, and recrystallized from n-hexane to provide 82.8 mg (crude yield 98.3%) of the reaction product.

In 0.76 ml of acetonitrile was dissolved 38.1 mg of the crystal thus obtained and after adding thereto 1.5 ml of 0.1N hydrochloric acid, the mixture was allowed to stand for one hour at room temperature. To the reaction mixture was added 2 ml of a saturated aqueous sodium hydrogencarbonate solution. Then, the reaction mixture was extracted four times each time with 1 ml of chloroform and the extracts were combined with each other, washed twice each time with 1.5 ml of a saturated aqueous sodium sulfate solution, dried by anhydrous sodium sulfate, and concentrated under reduced pressure. The residue was subjected to column chromatography using chloroform-methanol-28% aqueous ammonia (12:1:0.1) to provide 31.5 mg (yield 91.8%) of 23,4'-dideoxy-23-diethanolaminomycaminosyl tylonolide. (Yield 90.2% from the 23-iodo compound).

(i) $[\alpha]_D^{20} + 34°$ (c 0.5, CHCl$_3$)
(ii) Anal. for $C_{35}H_{60}N_2O_{10}$:

|  | C (%) | H (%) | N (%) |
|---|---|---|---|
| Calculated: | 62.85 | 9.04 | 4.19 |
| Found: | 63.02 | 9.11 | 3.99 |

(iii) Mass(m/z): 669(M + 1), 118 ($^+$CH$_2$—N(CH$_2$CH$_2$OH)(CH$_2$CH$_2$OH))

EXAMPLE 66

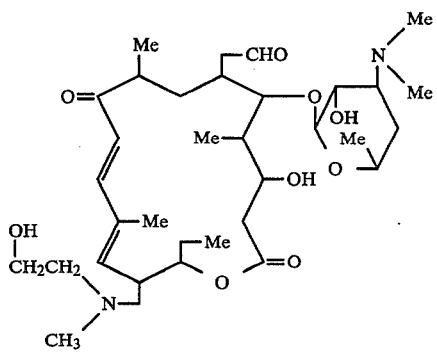

In 2.3 ml of acetonitrile was dissolved 114 mg of 23,4'-dideoxy-23-iodomycaminosyl tylonolide diethylacetal and after adding thereto 0.11 g of N-methylethanolamine, the mixture was heated at 80° C. for 4.5 hours with stirring. The reaction mixture was concentrated under reduced pressure and the residue was extracted with 5 ml of chloroform. The extract was washed with 2 ml of a saturated aqueous sodium hydrogencarbonate solution and then 2 ml of a saturated aqueous sodium sulfate solution, dried with anhydrous sodium sulfate, and concentrated under reduced pressure. The residue was subjected to column chromatography using chloroform-methanol-28% aqueous ammonia (30:1:0.1) to provide 87 mg (yield 93%) of the reaction product.

In 0.75 ml of acetonitrile was dissolved 37.2 mg of the product and after adding thereto 2 ml of 0.1N hydrochloric acid, the mixture was allowed to stand for one hour at room temperature. To the reaction mixture was added 2 ml of a saturated aqueous sodium hydrogencarbonate solution and the product was extracted three times each time with 1 ml of chloroform. The extracts were combined with each other, washed with 2 ml of a saturated aqueous sodium sulfate solution, dried by anhydrous sodium sulfate, and concentrated under reduced pressure. The residue was subjected to column chromatography using chloroform-methanol-28% aqueous ammonia (30:1:0.1) to provide 32.3 mg (yield 97%) of 23,4'-dideoxy-23-N-(2-hydroxyethyl)methylaminomycaminosyl tylonolide. (Yield 90% from the 23-iodo compound).

(i) $[\alpha]_D^{20} + 23°$ (c 1.0, CHCl$_3$)
(ii) Anal. for $C_{34}H_{58}N_2O_9$:

|  | C (%) | H (%) | N (%) |
|---|---|---|---|
| Calculated: | 63.92 | 9.15 | 4.38 |
| Found: | 64.12 | 9.04 | 4.49 |

(iii) Mass(m/z): 639(M + 1), 88 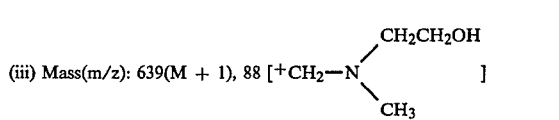

EXAMPLE 67

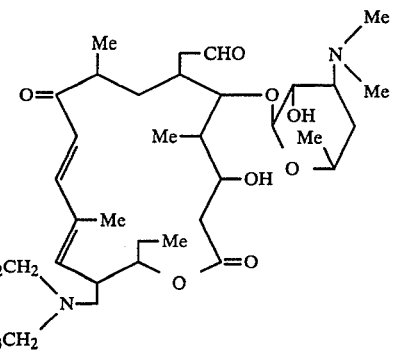

In 1.8 ml of acetonitrile was dissolved 91.7 mg of 23,4'-dideoxy-23-iodomycaminosyl tylonolide diethylacetal and after adding thereto 0.11 g of N-ethylethanolamine, the mixture was heated at 80° C. for 6 hours with stirring. The reaction mixture was concentrated under reduced pressure and the residue was dissolved in 6 ml of chloroform. The solution was washed twice each time with 2 ml of a saturated aqueous sodium hydrogencarbonate solution and then twice each time with 2 ml of a saturated aqueous sodium sulfate solution, dried by anhydrous sodium sulfate, and concentrated under reduced perssure. The residue was subjected to column chromatography using chloroform-methanol-28% aqueous ammonia (15:1:0.1) to provide 68.2 mg (yield 78.4%) of the reaction product.

In 1.1 ml of acetonitrile was dissolved 56.8 mg of the product thus obtained and after adding thereto 2.3 ml of 0.1N hydrochloric acid, the mixture was allowed to stand for one hour at room temperature.

To the reaction mixture was added 2 ml of a saturated aqueous sodium hydrogencarbonate solution and the product was extracted three times each time with 1 ml of chloroform. The extracts were combined with each other, washed twice each time with a saturated aqueous sodium sulfate solution, dried by anhydrous sodium sulfate, and concentrated under reduced pressure. The residue was subjected to column chromatography using chloroform-methanol-28% aqueous ammonia (30:1:0.1) to provide 47 mg (yield 92%) of 23,4'-dideoxy-23-N-ethyl(2-hydroxyethyl)aminomycaminosyl tylonolide. (Yield 71% from the 23-iodo compound).

(i) $[\alpha]_D^{20}$ + 30° (c 1.0, CHCl$_3$)
(ii) Anal. for C$_{35}$H$_{60}$N$_2$O$_9$:

|  | C (%) | H (%) | N (%) |
|---|---|---|---|
| Calculated: | 64.39 | 9.26 | 4.29 |
| Found: | 64.48 | 9.14 | 4.30 |

(iii) Mass(m/z): 653(M + 1), 102 ($^+$CH$_2$—N(CH$_2$CH$_2$OH)(CH$_2$CH$_3$))

EXAMPLE 68

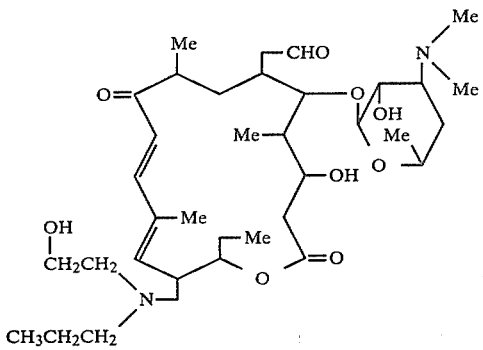

In 1.9 ml of acetonitrile was dissolved 96 mg of 23,4'-dideoxy-23-iodomycaminosyl tylonolide diethylacetal and after adding thereto 0.13 g of N-propylethanolamine, the mixture was heated at 80° C. for 16 hours with stirring.

The reaction mixture was concentrated under reduced pressure and the residue was extracted with 5 ml of chloroform. The extract was washed three times each time with 2 ml of a saturated aqueous sodium hydrogencarbonate solution, and then twice each time with 2 ml of a saturated aqueous sodium sulfate solution, dried with anhydrous sodium sulfate, and concentrated under reduced pressure.

The residue was subjected to column chromatography using chloroform-methanol-28% aqueous ammonia (30:1:0.1) to provide 86.5 mg (yield 89%) of the reaction product.

In 0.6 ml of acetonitrile was dissolved 30 mg of the product and after adding thereto 1.2 ml of 0.1N hydrochloric acid, the mixture was allowed to stand for one hour at room temperature. To the reaction mixture was added 1.5 ml of a saturated aqueous sodium hydrogencarbonate solution and the product was extracted three times each time with 1 ml of chloroform. The extracts were combined with each other, washed with 2 ml of a saturated aqueous sodium sulfate solution, dried by anhydrous sodium sulfate, and concentrated under reduced perssure. The residue was subjected to column chromatography using chloroform-methanol-28% aqueous ammonia (30:1:0.1) to provide 25.4 mg (yield 94%) of 23,4'-dideoxy-23-N-propyl(2-hydroxyethyl)aminomycaminosyl tylonolide. (Yield 83% from the 23-iodo compound).

(i) $[\alpha]_D^{20}$ + 38° (c 1.0, CHCl$_3$)
(ii) Anal. for C$_{36}$H$_{62}$N$_2$O$_9$:

|  | C (%) | H (%) | N (%) |
|---|---|---|---|
| Calculated: | 64.86 | 9.31 | 4.20 |
| Found: | 64.60 | 9.22 | 4.46 |

(iii) Mass(m/z): 667(M + 1), 116 ($^+$CH$_2$—N(CH$_2$CH$_2$OH)(CH$_2$CH$_2$CH$_3$))

EXAMPLE 69

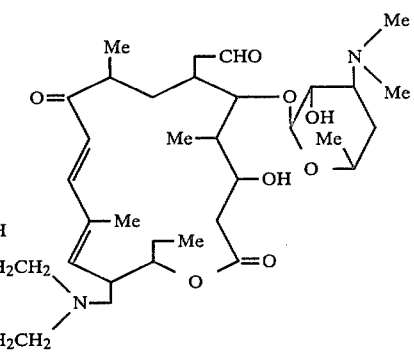

In 2.4 ml of acetonitrile was dissolved 118 mg of 23,4'-dideoxy-23-iodomycaminosyl tylonolide diethylacetal and after adding thereto 0.18 g of N-butylethanolamine, the mixture was heated at 80° C. for 23 hours with stirring.

The reaction mixture was concentrated under reduced pressure and the residue was extracted with 5 ml of chloroform. The extract was washed twice each time with 2 ml of a saturated aqueous sodium hydrogencarbonate solution and then 2 ml of a saturated aqueous sodium sulfate solution, dried by anhydrous sodium sulfate, and concentrated under reduced pressure. The residue was subjected to column chromatography using chloroform-methanol-28% aqueous ammonia (30:1:0.1) to provide 88.7 mg (yield 76%) of the reaction product.

In 1.2 ml of acetonitrile was dissolved 59.7 mg of the product and after adding thereto 24 ml of 0.1N hydrochloric acid, the mixture was allowed to stand for one hour at room temperature.

To the reaction mixture was added 3 ml of a saturated aqueous sodium hydrogencarbonate solution and the mixture was extracted with 4 ml of chloroform. The extract was washed twice each time with 2 ml of a saturated aqueous sodium sulfate solution, dried by anhydrous sodium sulfate, and concentrated under reduced pressure. The residue was subjected to column chromatography using chloroform-methanol-28% aqueous ammonia (30:1:0.1) to provide 30.4 mg (yield 57%) of 23,4'-dideoxy-23-N-butyl(2-hydroxyethyl)aminomycaminosyl tylonolide.

(i) $[\alpha]_D^{20}$ + 32° (c 0.5, CHCl$_3$)
(ii) Anal. for C$_{37}$H$_{64}$N$_2$O$_9$:

|  | C (%) | H (%) | N (%) |
|---|---|---|---|
| Calculated: | 65.29 | 9.41 | 4.12 |

-continued

| Found: | 65.00 | 9.23 | 4.07 |
|---|---|---|---|

(iii) Mass(m/z): 681(M + 1), 130 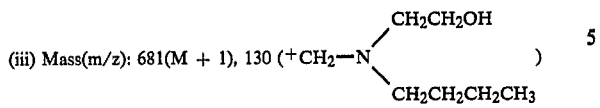

EXAMPLE 70

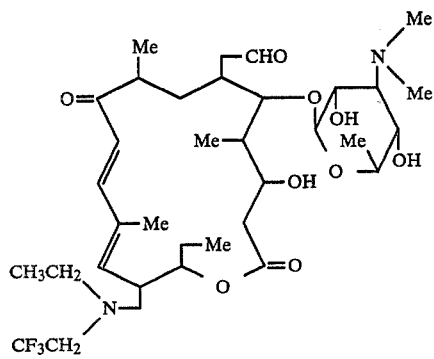

In 0.81 ml of benzene was dissolved 81.5 mg of 23-deoxy-23-ethylaminomycaminosyl tylonolide diethylacetal and after adding thereto 0.27 g of 2,2,2-trifluoroethyl trifluoromethan sulfonate (CF$_3$CH$_2$OSO$_2$CF$_3$) and then 0.13 ml of triethylamine, the mixture was heated at 120° C. for 2 hours. The reaction mixture was concentrated under reduced pressure and the residue was extracted with 4 ml of chloroform. The extract was washed twice each time with 3 ml of a saturated aqueous sodium hydrogencarbonate solution and then once with 3 ml of an saturated aqueous sodium sulfate solution, dried by anhydrous sodium sulfate, and then concentrated under reduced pressure. The residue was subjected to silica gel column chromatography using chloroform-methanol-28% aqueous ammonia (15:1:0.1).

The reaction product thus obtained was dissolved in 0.74 ml of acetonitrile and after adding thereto 2.8 ml of 0.1N hydrochloric acid, the mixture was allowed to stand for one hour at room temperature. To the reaction mixture was added 2 ml of a saturated aqueous sodium hydrogencarbonate solution and the product was extracted with 3 ml of chloroform. The extract was washed with a saturated aqueous sodium sulfate solution, dried by anhydrous sodium sulfate, and then concentrated under reduced pressure. The residue was recrystallized from acetone-n-hexane to provide 600 mg of 23-deoxy-23-N-(2,2,2-trifluoroethyl)ethylaminomycaminosyl tylonolide.

(i) [α]$_D^{20}$ + 12.5° (c 1.0, CHCl$_3$)
(ii) Anal. for C$_{35}$H$_{57}$N$_2$O$_9$F$_3$:

| | C(%) | H(%) | N(%) |
|---|---|---|---|
| Calculated: | 59.47 | 8.13 | 3.96 |
| Found: | 59.29 | 8.23 | 3.92 |

(iii)   Mass(m/z): 706(M+), 140 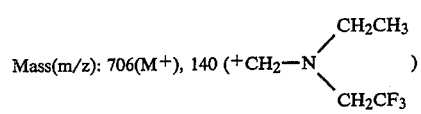

By following almost the same procedure as in Example 70, the following compounds were prepared:

EXAMPLE 71

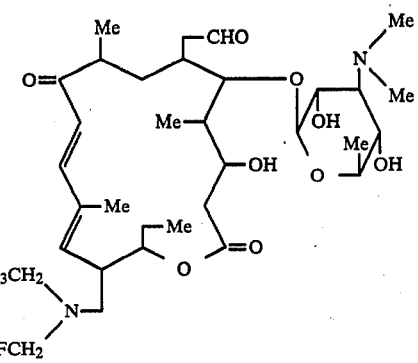

23-Deoxy-23-N-(2,2-difluoroethyl)ethylaminomycaminosyl tylonolide.

(i) [α]$_D^{20}$ + 16° (c 1.0, CHCl$_3$)
(ii) Anal. for C$_{35}$H$_{58}$N$_2$O$_9$F$_2$.1/2H$_2$O:

| | C(%) | H(%) | N(%) |
|---|---|---|---|
| Calculated: | 60.24 | 8.52 | 4.01 |
| Found: | 60.26 | 8.56 | 4.01 |

(iii)   Mass(m/z): 688(M+), 122 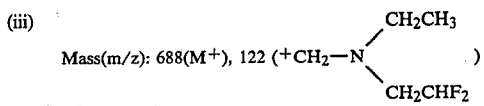

EXAMPLE 72

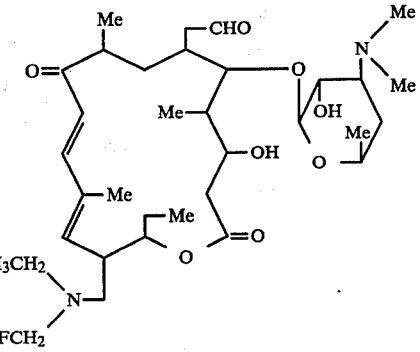

23,4'-Dideoxy-23-N-(2-fluoroethyl)ethylaminomycaminosyl tylonolide.

(i) [α]$_D^{20}$ + 22° (c 1.0, CHCl$_3$)
(ii) Anal. for C$_{35}$H$_{59}$N$_2$O$_8$F:

| | C(%) | H(%) | N(%) |
|---|---|---|---|
| Calculated: | 64.19 | 9.08 | 4.28 |
| Found: | 64.04 | 9.11 | 4.29 |

(iii)   Mass(m/z): 654(M+), 104 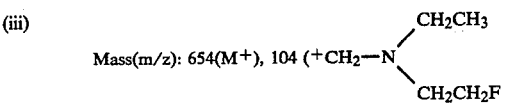

EXAMPLE 73

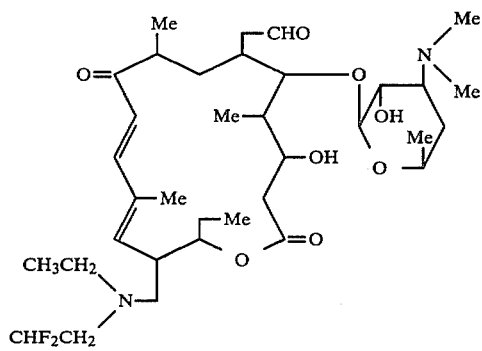

23,4'-Dideoxy-23-N-(2,2-difluoroethyl)ethylaminomycaminosyl tylonolide.

(i) $[\alpha]_D^{20} + 16°$ (c 1.0, CHCl$_3$)
(ii) Anal. for $C_{35}H_{58}N_2O_8F_2$:

| | C(%) | H(%) | N(%) |
|---|---|---|---|
| Calculated: | 62.48 | 8.69 | 4.16 |
| Found: | 62.23 | 8.56 | 4.15 |

(iii) 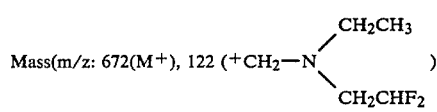

Mass(m/z): 672(M+), 122 (+CH$_2$—N(CH$_2$CH$_3$)(CH$_2$CHF$_2$))

EXAMPLE 74

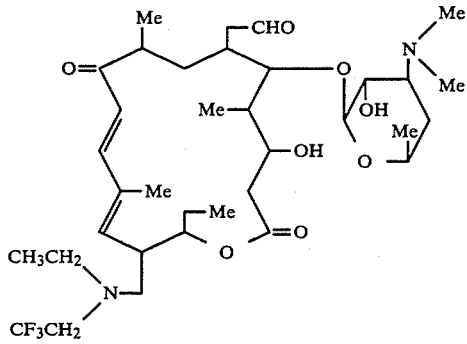

23,4'-Dideoxy-23-N-(2,2,2-trifluoroethyl)ethylaminomycaminosyl tylonolide.

(i) $[\alpha]_D^{20} + 11°$ (c 1.0, CHCl$_3$)
(ii) Anal. for $C_{35}H_{57}N_2O_9F_3$:

| | C(%) | H(%) | N(%) |
|---|---|---|---|
| Calculated: | 60.85 | 8.32 | 4.05 |
| Found: | 60.87 | 8.45 | 4.05 |

(iii) 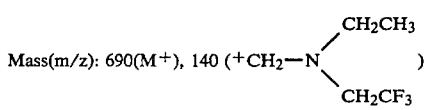

Mass(m/z): 690(M+), 140 (+CH$_2$—N(CH$_2$CH$_3$)(CH$_2$CF$_3$))

EXAMPLE 75

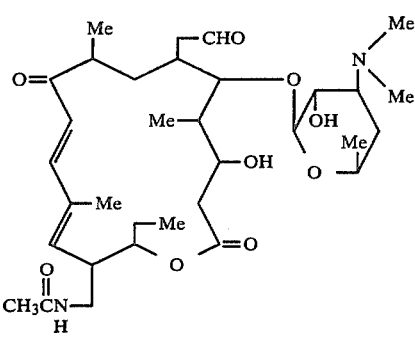

In 3.4 ml of 60% methanol-water was dissolved 68.8 mg of 23-amino-23,4'-dideoxymycaminosyl tylonolide diethylacetal and after adding thereto 26 mg of sodium hydrogencarbonate and then 21.4 mg of acetic anhydride under ice-cooling, the mixture was stirred. After 10 minutes, the mixture was further stirred for 2 hours at room temperature. To the reaction mixture was added 1 ml of a saturated aqueous sodium hydrogencarbonate and the mixture was extracted with 3 ml of chloroform. The extract was washed with 2 ml of a saturated aqueous sodium sulfate, dried by anhydrous sodium sulfate, and concentrated under reduced pressure. The residue was dissolved in 1.5 ml of acetonitrile and after adding thereto 4.2 ml of 0.1N hydrochloric acid, the mixture was allowed to stand for one hour at room temperature. To the reaction mixture was added 2 ml of a saturated aqueous sodium hydrogencarbonate solution and the product was extracted with 3 ml of chloroform. The extract was washed with 2 ml of a saturated aqueous sodium sulfate solution, dried by anhydrous sodium sulfate, and concentrated under reduced pressure. The residue was subjected to silica gel column chromatography using chloroform-methanol-28% aqueous ammonia (30:1:0.1) to provide 57.8 mg (yield 88%) of 23-acetamido-23,4'-dideoxymycaminosyl tylonolide.

(i) $[\alpha]_D^{25} + 57°$ (c 1.0, CHCl$_3$)
(ii) Anal. for $C_{33}H_{54}N_2O_9$:

| | C (%) | H (%) | N (%) |
|---|---|---|---|
| Calculated: | 63.66 | 8.68 | 4.50 |
| Found: | 63.94 | 8.90 | 4.30 |

By following the same procedure as in Example 75, the following compound was obtained.

EXAMPLE 76

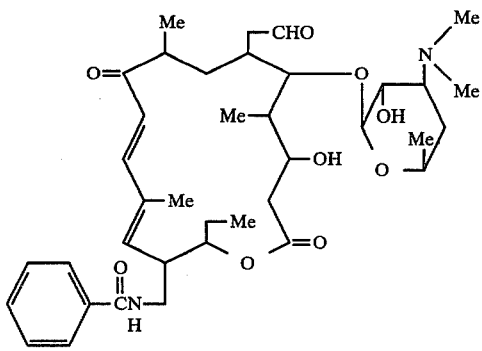

23-Benzoylamino-23,4'-dideoxymycaminosyl tylonolide.

(i) $[\alpha]_D^{25} + 77°$ (c 1.0, CHCl₃)
(ii) Anal. for C₃₈H₅₆N₂O₉:

|  | C (%) | H (%) | N (%) |
|---|---|---|---|
| Calculated: | 66.66 | 8.19 | 4.09 |
| Found: | 66.47 | 8.38 | 4.25 |

EXAMPLE 77

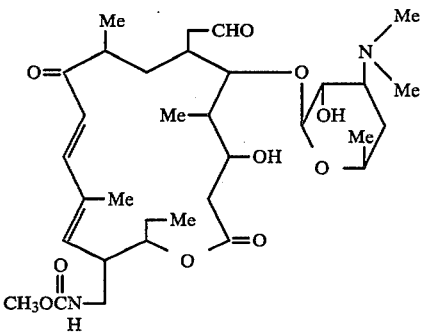

In 2.6 ml of 60% methanol-water was dissolved 52.4 mg of 23-amino-23,4'-dideoxymycaminosyl tylonolide and after adding thereto 20 mg of sodium hydrogencarbonate, 11 mg of methoxycarbonyl chloride was added to the mixture under ice-cooling. Thereafter, the mixture was stirred for 2 hours at room temperature.

To the reaction mixture was added 2 ml of a saturated aqueous sodium hydrogencarbonate solution and the product was extracted with 3 ml of chloroform. The extract was washed with 2 ml of a saturated aqueous sodium sulfate solution, dried by anhydrous sodium sulfate, and concentrated under reduced pressure. The residue was subjected to silica gel column chromatography using chloroform-methanol-28% aqueous ammonia (20:1:0.1).

The product thus obtained was dissolved in 1 ml of acetonitrile and after adding thereto 2.9 ml of 0.1N hydrochloric acid, the mixture was allowed to stand for one hour at room temperature. To the reaction mixture was added 2 ml of a saturated aqueous sodium hydrogencarbonate solution and the product was extracted with 3 ml of chloroform. The extract was washed with a saturated aqueous sodium sulfate solution, dried by anhdrous sodium sulfate, and concentrated under reduced pressure. The residue was subjected to silica gel column chromatography using chloroform-methanol-28% aqueous ammonia (20:1:0.1) to provide 34.6 mg (yield 67.7%) of 23,4'-dideoxy-23-methoxycarbonylaminomycaminosyl tylonolide.

(i) $[\alpha]_D^{25} + 50°$ (c 1.0, CHCl₃)
(ii) Anal. for C₃₃H₅₄N₂O₁₀:

|  | C (%) | H (%) | N (%) |
|---|---|---|---|
| Calculated: | 62.07 | 8.46 | 4.39 |
| Found: | 62.27 | 8.45 | 4.53 |

By following the same procedure as in Example 77, the following compounds were prepared.

EXAMPLE 78

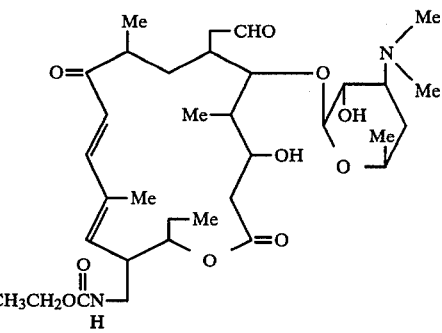

23,4'-Dideoxy-23-ethoxycarbonylaminomycaminosyl tylonolide.

(i) $[\alpha]_D^{25} + 48°$ (c 1.0, CHCl₃)
(ii) Anal: for C₃₄H₅₆N₂O₁₀:

|  | C (%) | H (%) | N (%) |
|---|---|---|---|
| Calculated: | 62.58 | 8.59 | 4.29 |
| Found: | 62.31 | 8.43 | 4.04 |

EXAMPLE 79

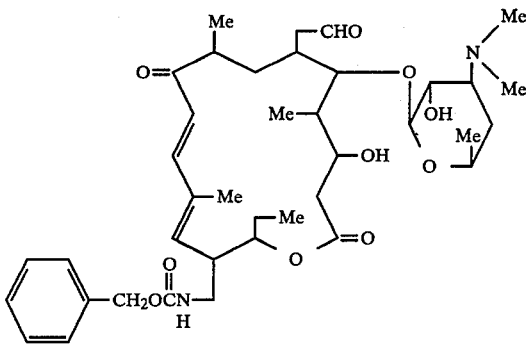

23-Benzyloxycarbonylamino-23,4'-dideoxymycaminosyl tylonolide.

(i) $[\alpha]_D^{25} + 47°$ (c 1.0, CHCl₃)
(ii) Anal. for C₃₉H₅₈N₂O₁₀:

|  | C (%) | H (%) | N (%) |
|---|---|---|---|
| Calculated: | 65.55 | 8.12 | 3.92 |
| Found: | 65.81 | 8.11 | 3.75 |

EXAMPLE 80

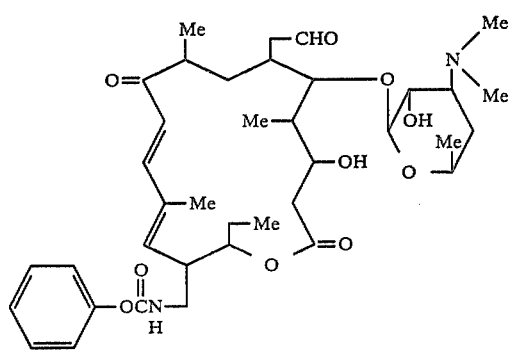

23,4'-Dideoxy-23-phenoxycarbonylaminomycaminosyl tylonolide.

(i) $[\alpha]_D^{25} + 71°$ (c 1.0, CHCl$_3$)
(ii) Anal. for C$_{38}$H$_{56}$N$_2$O$_{10}$:

|  | C (%) | H (%) | N (%) |
|---|---|---|---|
| Calculated: | 65.14 | 8.00 | 4.00 |
| Found: | 64.89 | 8.07 | 4.17 |

EXAMPLE 81

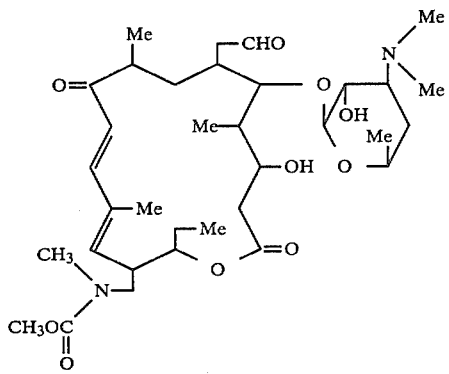

23,4'-Dideoxy-23-N-methoxycarbonylmethylaminomycaminosyl tylonolide.

(i) $[\alpha]_D^{25} + 61°$ (c 1.0, CHCl$_3$)
(ii) Anal. for C$_{34}$H$_{56}$N$_2$O$_{10}$·½H$_2$O:

|  | C (%) | H (%) | N (%) |
|---|---|---|---|
| Calculated: | 61.72 | 8.62 | 4.23 |
| Found: | 61.78 | 8.36 | 3.98 |

EXAMPLE 82

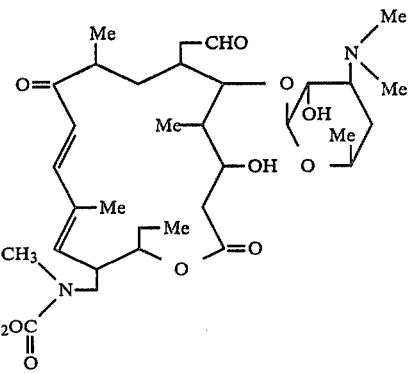

23-N-Benzyloxycarbonylmethylamino-23,4'-dideoxymycaminosyl tylonolide.

(i) $[\alpha]_D^{25} + 64°$ (c 1.0, CHCl$_3$)
(ii) Anal. for C$_{40}$H$_{60}$N$_2$O$_{10}$:

|  | C (%) | H (%) | N (%) |
|---|---|---|---|
| Calculated: | 65.93 | 8.24 | 3.85 |
| Found: | 66.11 | 8.17 | 3.82 |

EXAMPLE 83

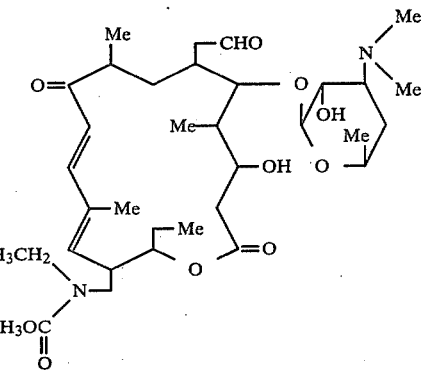

23,4'-Dideoxy-23-N-ethylmethoxycarbonylaminomycaminosyl tylonolide.

(i) $[\alpha]_D^{25} + 68°$ (c 1.0, CHCl$_3$)
(ii) Anal. for C$_{35}$H$_{58}$N$_2$O$_{10}$:

|  | C (%) | H (%) | N (%) |
|---|---|---|---|
| Calculated: | 63.06 | 8.71 | 4.20 |
| Found: | 62.80 | 8.58 | 4.06 |

EXAMPLE 84

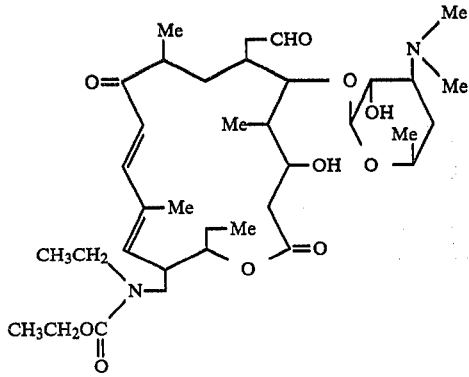

23,4′-Dideoxy-23-N-ethylethoxycarbonylaminomycaminosyl tylonolide.

(i) $[\alpha]_D^{25}$ + 80° (c 1.0, CHCl$_3$)

(ii) Anal. for C$_{36}$H$_{60}$N$_2$O$_{10}$:

|  | C (%) | H (%) | N (%) |
|---|---|---|---|
| Calculated: | 63.53 | 8.82 | 4.12 |
| Found: | 63.66 | 8.80 | 4.06 |

EXAMPLE 85

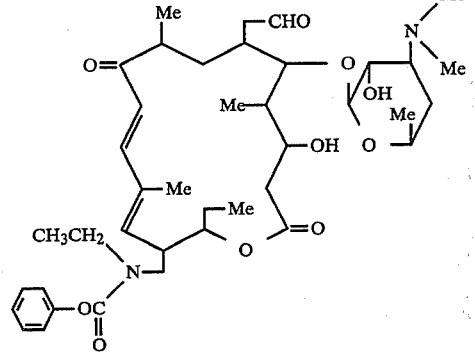

23,4′-Dideoxy-23-N-ethylphenoxycarbonylaminomycaminosyl tylonolide.

(i) $[\alpha]_D^{25}$ + 105° (c 1.0, CHCl$_3$)

(ii) Anal. for C$_{40}$H$_{60}$N$_2$O$_{10}$:

|  | C (%) | H (%) | N (%) |
|---|---|---|---|
| Calculated: | 65.93 | 8.24 | 3.85 |
| Found: | 66.17 | 8.24 | 3.97 |

EXAMPLE 86

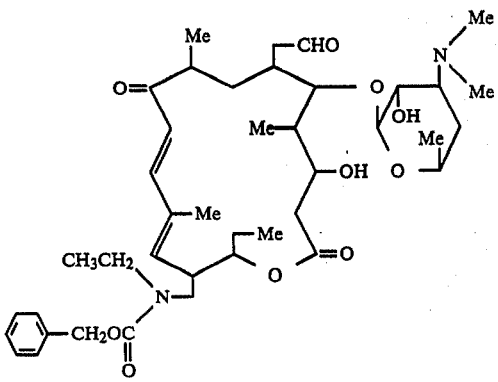

23-N-Benzyloxycarbonylethylamino-23,4′-dideoxymycaminosyl tylonolide.

(i) $[\alpha]_D^{25}$ + 80° (c 1.0, CHCl$_3$)

(ii) Anal. for C$_{41}$H$_{62}$N$_2$O$_{10}$:

|  | C (%) | H (%) | N (%) |
|---|---|---|---|
| Calculated: | 66.31 | 8.36 | 3.77 |
| Found: | 66.29 | 8.27 | 3.84 |

EXAMPLE 87

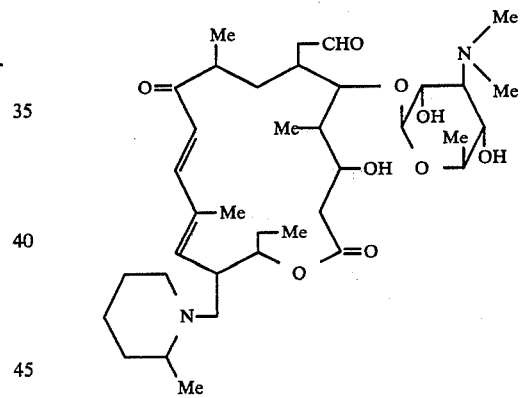

In 20 ml of acetonitrile was dissolved 1.0 g of 23-deoxyiodomycaminosyl tylonolide diethylacetal and after adding thereto 634 mg of 2-methylpiperidine, the mixture was refluxed for 2 hours. The solvent was distilled off and the residue was dissolved in chloroform. The solution was washed with a saturated aqueous sodium hydrogencarbonate solution and then a saturated aqueous sodium sulfate solution, dried by anhydrous sodium sulfate, and the solvent was distilled off. The residue was dissolved in 5 ml of acetonitrile and after adding thereto 19 ml of 0.2N hydrochloric acid, the mixture was allowed to stand for 60 minutes at room temperature. To the reaction mixture was added sodium hydrogencarbonate to make weak basic the reaction mixture and the product was extracted with chloroform. The chloroform extract was washed with water, dried by anhydrous sodium sulfate, and then the solvent was distilled off. The residue thus obtained was purified by column chromatography using a solvent system of chloroform-methanol-28% aqueous ammonia (15:1:0.1) to provide 590 mg (yield 68%) of a colorless solid of 23-deoxy-23-(2-methylpiperidino)mycaminosyl tylonolide.

(i) NMR (CDCl₃):

| δ(ppm) | H number | Form | J(Hz) | |
|---|---|---|---|---|
| 1.80 | 3 | s | | Me(22) |
| 2.49 | 6 | s | | NMe₂ |
| 4.30 | 1 | d₁',₂' | 7.5 | H₁' |
| 4.77 | 1 | m | | H₁₅ |
| 5.72 | 1 | d₁₃,₁₄ | 10 | H₁₃ |
| 6.24 | 1 | d₁₀,₁₁ | 16 | H₁₀ |
| 7.32 | total sum 1 | d₂ | | H₁₁ |
| 9.70 | 1 | s | | H₂₀ |

(ii) IR (KBr) (cm⁻¹):

| 2970 | —CH₃ |
| 2940 | —CH₂— |
| 1720 | —COO—, —CHO |
| 1680 | 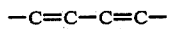 |
| 1595 | —C=C—C=C— |

(iii) Mass (m/z):
678(M⁺), 629, 567, 534, 488, 460, 402, 174, 112, 87.

(iv) Anal. for C₃₇H₆₂N₂O₉:

| | C (%) | H (%) | N (%) |
|---|---|---|---|
| Calculated: | 65.46 | 9.21 | 4.13 |
| Found: | 65.20 | 9.02 | 4.35 |

EXAMPLE 88

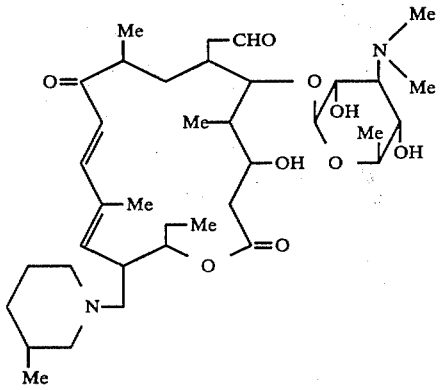

By following the same procedure as in Example 87 using 1.42 g of 23-deoxy-23-iodomycaminosyl tylonolide diethylacetal and 901 mg of 3-methylpiperidine, 670 mg (yield 56%) of a colorless solid of 23-deoxy-23-(3-methylpiperidino)mycaminosyl tylonolide was obtained.

(i) NMR (CDCl₃):

| δ(ppm) | H number | Form | J(Hz) | |
|---|---|---|---|---|
| 1.80 | 3 | s | | Me(22) |
| 2.49 | 6 | s | | NMe₂ |
| 4.28 | 1 | d₁',₂' | 7.5 | H₁' |
| 4.77 | 1 | m | | H₁₅ |
| 5.74 | 1 | d₁₃,₁₄ | 10 | H₁₃ |
| 6.25 | 1 | d₁₀,₁₁ | 16 | H₁₀ |
| 7.35 | 1 | d | | H₁₁ |
| 9.70 | 1 | s | | H₂₀ |

(ii) IR (KBr) (cm⁻¹):

| 2970 | —CH₃ |
| 2940 | —CH₂— |
| 1720 | —COO—, —CHO |
| 1690 | 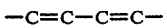 |
| 1595 | —C=C—C=C— |

(iii) Mass (m/z):
678(M⁺), 585, 534, 488, 232, 174, 112, 87.

(v) Anal. for C₃₇H₆₂N₂O₉:

| | C (%) | H (%) | N (%) |
|---|---|---|---|
| Calculated: | 65.46 | 9.21 | 4.13 |
| Found: | 65.32 | 9.08 | 4.21 |

EXAMPLE 89

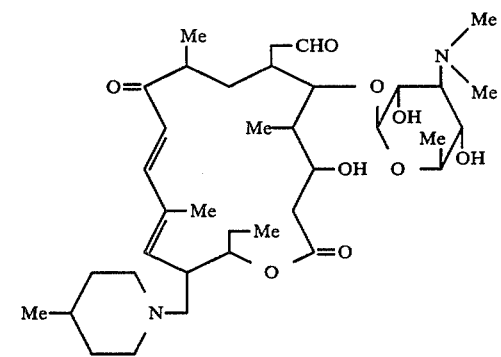

By following the same procedure as in Example 87 using 1.08 g of 23-deoxy-23-iodomycaminosyl tylonolide diethylacetal and 683 mg of 4-methylpiperidine, 560 mg (yield 60%) of a colorless solid of 23-deoxy-23-(4-methylpiperidino)mycaminosyl tylonolide was obtained.

(i) NMR (CDCl₃):

| δ(ppm) | H number | Form | J(Hz) | |
|---|---|---|---|---|
| 1.80 | 3 | s | | Me(22) |
| 2.48 | 6 | s | | NMe₂ |
| 4.28 | 1 | d₁',₂' | 7.5 | H₁' |
| 4.76 | 1 | m | | H₁₅ |
| 5.80 | 1 | d₁₃,₁₄ | 10 | H₁₃ |
| 6.24 | 1 | d₁₀,₁₁ | 16 | H₁₀ |
| 7.34 | 1 | d | | H₁₁ |
| 9.71 | 1 | s | | H₂₀ |

(ii) IR (KBr) (cm⁻¹):

| 2970 | —CH₃ |
| 2940 | —CH₂— |
| 1720 | —COO—, —CHO |
| 1680 | 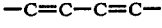 |
| 1595 | —C=C—C=C— |

(iii) Mass (m/z):
678(M⁺), 534, 488, 446, 232, 174, 112, 87.

(iv) Anal. for C₃₇H₆₂N₂O₉:

| | C (%) | H (%) | N (%) |
|---|---|---|---|
| Calculated: | 65.46 | 9.21 | 4.13 |
| Found: | 65.33 | 9.20 | 4.24 |

EXAMPLE 90

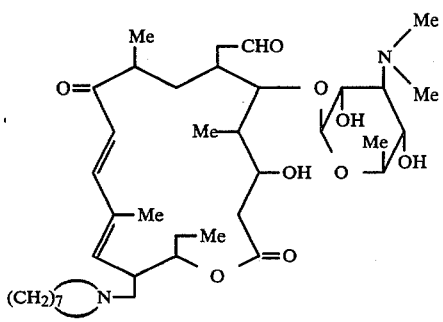

By following the same procedure as in Example 87 using 0.93 g of 23-deoxy-23-iodomycaminosyl tylonolide diethylacetal and 672 mg of heptamethyleneimine, 370 mg (yield 45%) of a colorless solid of 23-deoxy-23-heptamethyleneiminomycaminosyl tylonolide was obtained.

(i) NMR (CDCl₃):

| δ(ppm) | H number | Form | J(Hz) | |
|---|---|---|---|---|
| 1.49 | ~10 | m | | 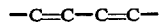 |
| 1.81 | 3 | s | | Me(22) |
| 2.48 | 6 | s | | NMe$_2$ |
| 4.28 | 1 | d$_{1',2'}$ | 7.5 | H$_{1'}$ |
| 4.76 | 1 | m | | H$_{15}$ |
| 5.80 | 1 | d$_{13,14}$ | 10 | H$_{13}$ |
| 6.25 | 1 | d$_{10,11}$ | 16 | H$_{10}$ |
| 7.36 | 1 | d | | H$_{11}$ |
| 9.71 | 1 | s | | H$_{20}$ |

(ii) IR (KBr) (cm$^{-1}$):

| 2970 | —CH$_3$ |
|---|---|
| 2940 | —CH$_2$— |
| 1720 | —COO—, —CHO |
| 1680 | $\diagdown$C=O$\diagup$ |
| 1595 | —C=C—C=C— |

(iii) Mass (m/z):

692(M$^+$), 661, 548, 502 342, 174, 126, 87.

(iv) Anal. for C$_{38}$H$_{64}$N$_2$O$_9$:

| | C(%) | H(%) | N(%) |
|---|---|---|---|
| Calculated: | 65.87 | 9.31 | 4.04 |
| Found: | 65.59 | 9.25 | 4.23 |

EXAMPLE 91

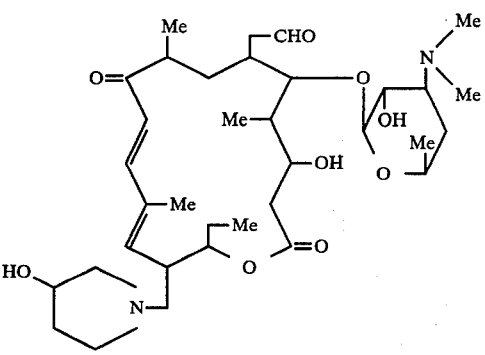

After dissolving 1.07 g of 23,4'-dideoxy-23-iodomycaminosyl tylonolide diethylacetal in 20 ml of acetonitrile, 609 mg of 3-hydroxypyrrolidine was added to the solution and the reaction was performed for 2.5 hours at 80° C. The solvent was distilled off under reduced pressure and the residue thus obtained was dissolved in chloroform. The solution was washed with a saturated sodium hydrogencarbonate solution and a saturated sodium sulfate solution, dried over anhydrous sodium sulfate, and the solvent was distilled off under reduced pressure. The residue thus obtained was dissolved in 5 ml of acetonitrile and after adding 21 ml of 0.2N hydrochloric acid to the solution, the mixture was allowed to stand for one hour at room temperature. After weakly alkalifying the mixture with sodium hydrogencarbonate, the product was extracted with chloroform. The extract was washed with water, dried over anhydrous sodium sulfate, and distilled off. The residue thus obtained was purified by silica gel culumn using a developing solvent of chloroform, methanol and 28% aqueous ammonia (15:1:0.1) to provide 580 mg (yield 64%) of colorless solid of 23,4'-dideoxy-23-(3-hydroxypyrrolidino)-mycaminosyl tylonolide.

(i) NMR (CDCl₃):

| δ(ppm) | H number | Form | J(Hz) | |
|---|---|---|---|---|
| 1.80 | 3 | s | | Me(22) |
| 2.26 | 6 | s | | NMe$_2$ |
| 4.20 | 1 | d$_{1',2'}$ | 7.5 | H$_{1'}$ |
| 4.77 | 1 | m | | H$_{15}$ |
| 5.78 | 1 | d$_{13,14}$ | 10 | H$_{13}$ |
| 6.28 | 1 | d$_{10,11}$ | 16 | H$_{10}$ |
| 7.34 | 1 | d | | H$_{11}$ |
| 9.72 | 1 | s | | H$_{20}$ |

(ii) IR (KBr) (cm$^{-1}$):

| 2970 | —CH$_3$ |
|---|---|
| 2940 | —CH$_2$— |
| 1725 | —COO—, —CHO |
| 1680 |  |
| 1600 | —C=C—C=C— |

(iii) Mass (m/z):

650(M$^+$), 551, 476, 174, 158, 100

(iv) Anal. for C$_{35}$H$_{58}$N$_2$O$_9$:

| | C (%) | H (%) | N (%) |
|---|---|---|---|
| Calculated: | 64.59 | 8.98 | 4.30 |
| Found: | 64.39 | 8.72 | 4.41 |

EXAMPLE 92

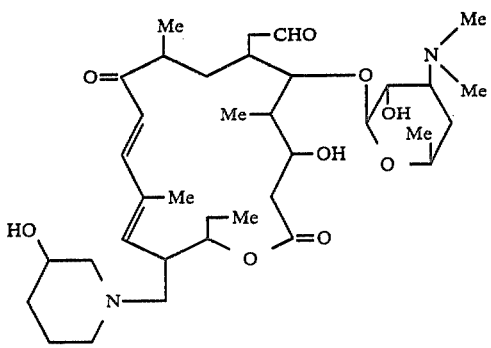

By treating 1.00 g of 23,4'-dideoxy-23-iodomycaminosyl tylonolide diethylacetal and 662 mg of 3-hydroxypiperidine as in Example 91, 580 mg (yield 67%) of colorless solid of 23,4'-dideoxy-23-(3-hydroxypiperidino)mycaminosyl tylonolide was obtained.

(i) NMR (CDCl₃):

| δ (ppm) | H number | Form | J (Hz) | |
|---|---|---|---|---|
| 1.80 | 3 | s | | Me (22) |
| 2.28 | 6 | s | | NMe₂ |
| 4.20 | 1 | $d_{1',2'}$ | 7.5 | $H_{1'}$ |
| 4.75 | 1 | m | | $H_{15}$ |
| 5.74 | 1 | $d_{13,14}$ | 10 | $H_{13}$ |
| 6.27 | 1 | $d_{10,11}$ | 16 | $H_{10}$ |
| 7.34 | 1 | d | | $H_{11}$ |
| 9.72 | 1 | s | | $H_{20}$ |

(ii) IR (KBr) (cm⁻¹):

| | |
|---|---|
| 2970 | —CH₃ |
| 2940 | —CH₂— |
| 1725 | —COO—, —CHO |
| 1680 | \C=O / |
| 1595 | —C=C—C=C— |

(iii) Mass (m/z):
664(M⁺), 620, 607, 174, 158, 114, 99

(iv) Anal. for C₃₆H₆₀N₂O₉:

| | C (%) | H (%) | N (%) |
|---|---|---|---|
| Calculated: | 65.03 | 9.10 | 4.21 |
| Found: | 64.91 | 9.02 | 4.33 |

EXAMPLE 93

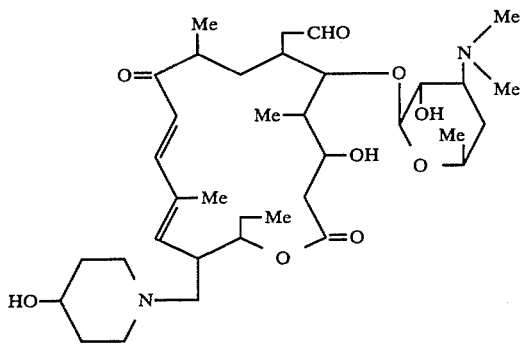

By treating 0.96 g of 23,4'-dideoxy-23-iodomycaminosyl tylonolide diethylacetal and 631 mg of 4-hydroxypiperidine as in Example 91, 660 mg (yield 80%) of colorless solid of 23,4'-dideoxy-23-(4-hydroxypiperidino)mycaminosyl tylonolide was obtained.

(i) NMR (CDCl₃):

| δ (ppm) | H number | Form | J (Hz) | |
|---|---|---|---|---|
| 1.79 | 3 | s | | Me(20) |
| 2.25 | 6 | s | | NMe₂ |
| 4.20 | 1 | $d_{1',2'}$ | 7.5 | $H_{1'}$ |
| 4.73 | 1 | m | | $H_{15}$ |
| 5.74 | 1 | $d_{13,14}$ | 10 | $H_{13}$ |
| 6.28 | 1 | $d_{10,11}$ | 16 | $H_{10}$ |
| 7.33 | 1 | d | | $H_{11}$ |
| 9.72 | 1 | s | | $H_{20}$ |

(ii) IR (KBr) (cm⁻¹):

| | |
|---|---|
| 2970 | —CH₃ |
| 2940 | —CH₂— |
| 1725 | —COO—, —CHO |
| 1680 | \C=O / |
| 1595 | —C=C—C=C— |

(iii) Mass (m/z):
665(M + 1), 551, 490, 389, 174, 158, 114

(iv) Anal. for C₃₆H₆₀N₂O₉:

| | C (%) | H (%) | N (%) |
|---|---|---|---|
| Calculated: | 65.03 | 9.10 | 4.21 |
| Found: | 64.81 | 9.32 | 4.05 |

EXAMPLE 94

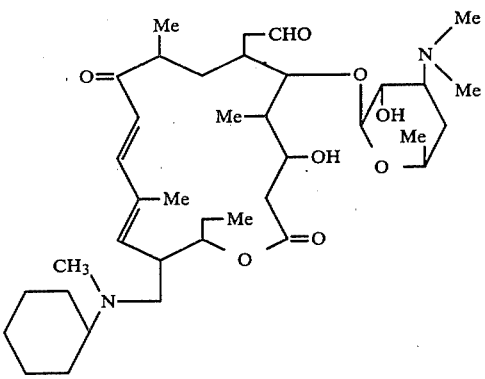

After dissolving 2.0 g of 23,4'-dideoxy-23-iodomycaminosyl tylonolide diethylacetal in 50 ml of acetonitrile, 1.77 g of N-methylcyclohexylamine was added to the solution and the mixture was refluxed for 7 hours. After cooling the mixture, acetonitrile was distilled off under reduced pressure and 200 ml of chloroform and 100 ml of a saturated aqueous sodium hydrogencarbonate solution were added to the residue thus obtained followed by shaking the mixture and then allowing to stand. The chloroform layer was recovered, washed with 100 ml of a saturated aqueous sodium chloride solution, dried over anhydrous magnesium sulfate, and distilled off under reduced pressure. The residue thus obtained was dissolved in a mixture of 78 ml of 0.1N hydrochloric acid and 38 ml of acetonitrile followed by allowing to stand for 3.5 hours at room temperature. After alkalifying the mixture with a saturated aqueous sodium hydrogencarbonate solution, the product was extracted three times each time with 100 ml, 50 ml and 30 ml of chloroform. The extracts were combined, washed with 100 ml of a saturated aqueous sodium chloride solution, dried over anhydrous magnesium sulfate, and distilled off under reduced pressure. The residue was purified by a silica gel (200 ml) column using a developing solvent of chloroform, methanol and conc. aqueous ammonia (15:1:0.1) to provide 1.2 g of yellowish amorphous powder of 23,4'-dideoxy-23-N-methylcyclohexylaminomycaminosyl tylonolide.

The extracts were combined, washed with a saturated aqueous sodium chloride solution, dried over anhydrous magnesium sulfate, and distilled off under reduced pressure. The residue was purified by a silica gel (100 ml) column using a developing solvent of chloroform, methanol and conc. aqueous ammonia (18:1:0.1) to provide 510 mg of yellowish amorphous powder of 23-deoxy-23-N-methyl-β-hydroxyethylaminomycaminosyl tylonolide.

(i) NMR (CDCl₃):

| δ (ppm) | H number | Form | |
|---|---|---|---|
| 1.80 | 3 | s | Me (22) |
| 2.20 | 3 | s | 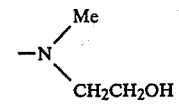 |
| 4.23 | 1 | d | H₁' |
| 4.74 | 1 | m | H₁₅ |
| 5.76 | 1 | d | H₁₃ |
| 6.27 | 1 | d | H₁₀ |
| 7.36 | 1 | d | H₁₁ |
| 9.74 | 1 | d | —CHO |

(ii) IR (KBr) (cm⁻¹):
3400, 2920, 2840, 1710, 1670, 1620, 1580

(iii) Mass (m/z):
676(M⁺), 564, 548, 502

(i) NMR (CDCl₃):

| δ (ppm) | H number | Form | |
|---|---|---|---|
| 1.83 | 3 | s | Me (22) |
| 2.23 | 3 | s | —N(Me)(CH₂CH₂OH) |
| 2.48 | 6 | s | —N(Me)(Me) |
| 4.26 | 1 | d | H₁' |
| 4.76 | 1 | m | H₁₅ |
| 5.73 | 1 | d | H₁₃ |
| 6.26 | 1 | d | H₁₀ |
| 7.31 | 1 | d | H₁₁ |
| 9.74 | 1 | s | —CHO |

(ii) IR (KBr) (cm⁻¹):
3450, 2930, 2860, 1715, 1675, 1620, 1585

(iii) Mass (m/z):
654(M⁺), 580, 510, 464

EXAMPLE 95

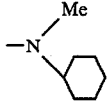

After dissolving 1 g of 23-deoxy-23-iodomycaminosyl tylonolide diethylacetal in 20 ml of acetonitrile, 576 mg of N-methylethanolamine was added to the solution and the mixture was refluxed for 5 hours. After cooling the mixture, acetonitrile was distilled off under reduced pressure and 100 ml of chloroform and 50 ml of a saturated aqueous sodium hydrogencarbonate solution were added to the residue thus obtained followed by shaking the mixture. The chloroform layer was recovered, washed with a saturated aqueous sodium chloride solution, dried over anhydrous magnesium sulfate, and distilled off under reduced pressure. The residue thus obtained was purified by a silica gel (100 ml) column using a developing solvent of chloroform and methanol (7:1) to provide 780 mg of colorless caramel. Then, 30 ml of 0.1N hydrochloric acid and 15 ml of acetonitrile were added to the caramel thus obtained followed by mixing for 3.5 hours at room temperature. After alkalifying the mixture with a saturated aqueous sodium hydrogencarbonate solution, the product was extracted three times each time with 100 ml, 50 ml and 30 ml of chloroform.

EXAMPLE 96

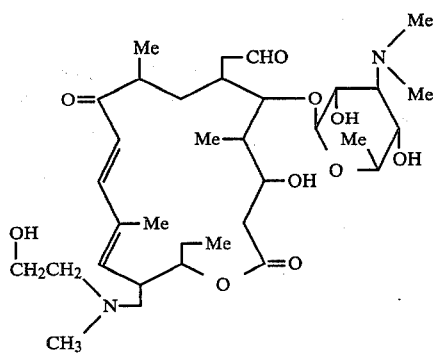

After dissolving 1 g of 23,4'-dideoxy-23-iodomycaminosyl tylonolide diethyl acetal in 20 ml of acetonitrile, 447 mg of cyclopropylamine was added to the solution and the mixture was refluxed for 7 hours. After cooling the mixture, acetonitrile was distilled off under reduced pressure and 100 ml of chloroform and 50 ml of a saturated aqueous sodium hydrogencarbonate solution were added to the residue thus obtained followed by vigorously shaking the mixture and then allowing to stand. The chloroform layer was recovered, washed with a saturated aqueous sodium chloride solution, dried over anhydrous magnesium sulfate, and distilled off under reduced pressure. The residue thus obtained was purified by a silica gel (200 ml) column using a developing solvent of chloroform and methanol (10:1) to provide 110 mg of yellow-brownish caramel. Then, 4.2 ml of 0.1N hydrochloric acid and 2.1 ml of acetonitrile were added to the caramel thus obtained followed by allowing to stand for 2 hours at room temperature. After alkalifying the mixture with a saturated aqueous sodium hydrogen-carbonate solution, the product was extracted three times each time with 50 ml, 30 ml and 20 ml of chloroform. The extracts were combined, washed with 50 ml of a saturated aqueous sodium chloride solution, dried over anhydrous magnesium sulfate, and distilled off under reduced pressure. The residue thus obtained was purified by a silica gel (20 ml) column using a developing solvent of chloroform, methanol and conc. aqueous ammonia (18:1:0.1) to provide 64 mg of yellowish amorphous powder of 23,4'-dideoxy-23-cyclopropylaminomycaminosyl tylonolide.

(i) NMR (CDCl$_3$)

| δ (ppm) | H number | Form | |
|---|---|---|---|
| 0.2–0.6 | 4 | m | —NH—<(H,H,H,H) (cyclopropyl) |
| 1.78 | 3 | s | Me (22) |
| 2.25 | 6 | s | —N(Me)(Me) |
| 4.20 | 1 | d | H$_{1'}$ |
| 4.80 | 1 | m | H$_{15}$ |
| 5.76 | 1 | d | H$_{13}$ |
| 6.29 | 1 | d | H$_{10}$ |
| 7.32 | 1 | d | H$_{11}$ |
| 9.71 | 1 | s | CHO |

(ii) IR (KBr) (cm$^{-1}$):
3450, 2930, 2860, 1720, 1680, 1585

(iii) Mass (m/z):
620(M$^+$)

What is claimed is:

1. A tylosin compound represented by the formula

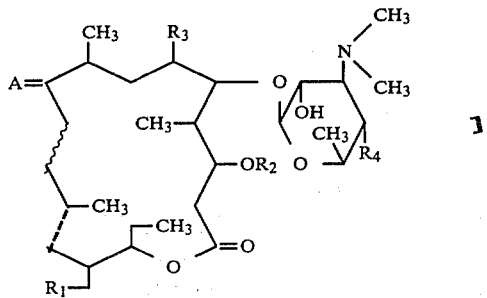

wherein R$_1$ is a hydroxyl group; a halogen atom; an

group wherein R$_5$ is a hydrogen atom or a lower alkyl group which is unsubstituted or substituted by a hydroxyl group, and R$_6$ is a hydrogen atom, a lower alkyl group which is unsubstituted or substituted by a hydroxyl group, an aryl group, an aralkyl group, a cyclo- alkyl group having 3-10 carbon atoms, a —CO(O)$_m$—R$_7$ group wherein m is 0 or 1, and R$_7$ is a lower alkyl group, an aryl group, an aralkyl group, a furanyl group, a pyridyl group, or —CH$_2$—R$_{13}$ group, wherein R$_{13}$ is a mono-, di-, or trifluoromethyl group; an —N(CH$_2$)$_n$ group wherein n is an integer of 2-15 and which is unsubstituted or substituted by an oxo group, a hydroxyl group, a lower alkyl group, or a hydroxy lower alkyl group, an imidazolyl group, a morpholino group, or a piperazino group each of which is unsubstituted or substituted by a lower alkyl group, or a —OOCCH$_2$—R$_8$ group wherein R$_8$ is an

group wherein R$_9$ and R$_{10}$, which may be the same or different, each is a hydrogen atom or a lower alkyl group; said R$_9$ and R$_{10}$ may be combined with each other to form an alkylene group having 3-7 carbon atoms or a —S—R$_{11}$ group wherein R$_{11}$ is a furanyl group or a pyridyl group; R$_2$ is a hydrogen atom or a lower alkanoyl group; R$_3$ is a methyl group or a —CH$_2$CHO group; R$_4$ is a hydrogen atom or a hydroxyl group; A is O=,

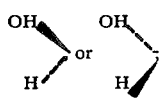

line~~~is a single bond or a double bond; and line - - - - is a single bond, a double bond, or ⟨o⟩; with the proviso that, when said R$_1$ is a hydroxyl group, said R$_3$ is a methyl group and R$_4$ is a hydrogen atom, or said line - - - - is ⟨o⟩; or when said R$_1$ is a halogen atom, said R$_3$ is a methyl group or said line - - - - is ⟨o⟩.

2. A tylosin compound as claimed in claim 1, wherein R$_1$ is a

group, R$_2$ is a hydrogen atom, R$_3$ is —CH$_2$CHO, R$_4$ is a hydrogen atom or a hydroxyl group, A is O=, and line ~~~ and line - - - - are a double bond.

3. A tylosin compound as claimed in claim 1 wherein R$_1$ is —N(CH$_2$)$_n$ group which is unsubstituted or substituted by an oxo group, a hydroxyl group, a lower alkyl group, or a hydroxy lower alkyl group, R$_2$ is a hydrogen atom, R$_3$ is —CH$_2$CHO, R$_4$ is a hydrogen atom or a hydroxyl group, A is O=, and line~~~and line - - - - are a double bond.

4. 23-Deoxy-23-hexamethyleneiminomycaminosyl tylonolide as claimed in claim 1.

5. A pharmaceutical composition containing a therapeutically effective amount of a tylosin compound as claimed in claim 1, in combination with a pharmaceutically acceptable carrier.

6. A method of producing a tylosin compound of the formula

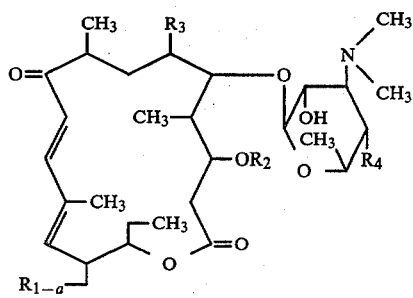

wherein $R_{1-a}$ is an

group wherein $R_5$ is a hydrogen atom or a lower alkyl group which is unsubstituted or substituted by a hydroxyl group and $R_6$, is a hydrogen atom, a lower alkyl group which is unsubstituted or substituted by a hydroxyl group; an aryl group, an aralkyl group, or a cycloalkyl group having 3-10 arbon atoms; an $-N(CH_2)_n$ group wherein n is an integer of 2-15 which is unsubstituted or substituted by an oxo group, a hydroxyl group, a lower alkyl group, or a hydroxy lower alkyl group; or an imidazolyl group, a morpholino group, or a piperazino group each of which is unsubstituted or substituted by a lower alkyl group; $R_2$ is a hydrogen atom or a lower alkanoyl group; $R_3$ is a methyl group or a $-CH_2CHO$ group; and $R_4$ is a hydrogen atom or a hydroxyl group, which comprises reacting a compound of the formula

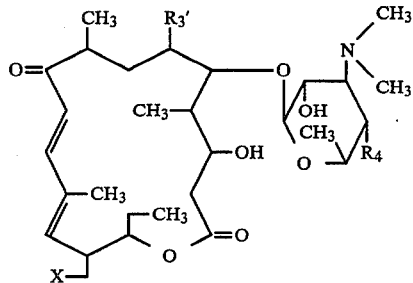

wherein X is a halogen atom, $R_3$, is a methyl group or a $-CH_2$—protected aldehyde group, and $R_4$ has the same significance as defined in the above formula, with a compound of the formula $R_{1-a}$—H wherein $R_{1-a}$ has the same significance as defined above, and when $R_3$, of the product of a $-CH_2$-protected aldehyde group, (i) removing the protective group for the aldehyde group or (ii)-(a) reacting the product with the carboxylic acid compound of the formula lower alkyl—COOH or a reactive derivative thereof, (b) treating the reaction product with an alcohol, and (c) removing the protective group for the aldehyde group.

7. A method of producing a tylosin compound of the formula

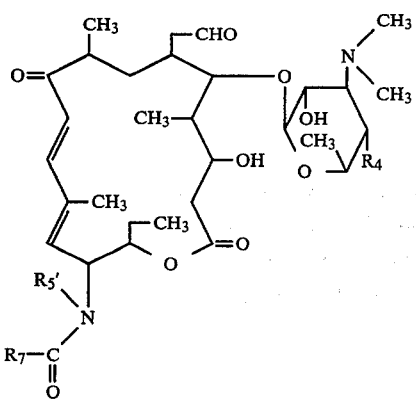

wherein $R_5$, is a lower alkyl group, $R_7$ is a lower alkyl group, an aryl group, an aralkyl group, a furanyl group, or a pyridyl group, and $R_4$ is a hydrogen atom or a hydroxyl group which comprises (a) reacting a compound of the formula

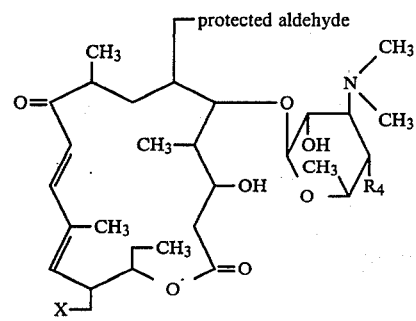

wherein X is a halogen atom and $R_4$ has the same significance as defined above, with a carboxylic acid compound of the formula lower alkyl—COOH or a reactive derivative thereof, (b) reacting the product with a compound of the formula $R_{5'}$—$NH_2$ wherein $R_{5'}$ has the same significance as defined above to produce a compound of the formula

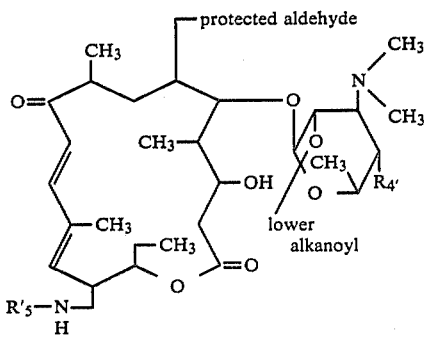

wherein $R_4$, is a hydrogen atom or a lower alkanoyloxy group and $R_5$, has the same significance as defined above, (c) reacting the product with a carboxylic acid compound of the formula

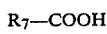

wherein $R_7$ has the same significance as defined above, or a reactive derivative therefor, (d) treating the reaction product with an alcohol, and (e) removing the protective group for the aldehyde group.

8. A method of producing a tylosin compound of the formula

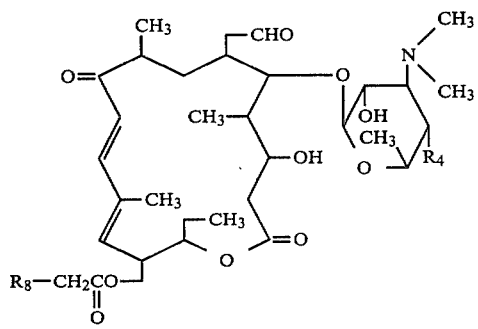

wherein $R_4$ is a hydrogen atom or a hydroxyl group and $R_8$ represents

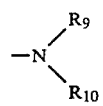

group wherein $R_9$ and $R_{10}$, which may be the same or different, each is a hydrogen atom or a lower alkyl group; said $R_8$ and $R_9$ may be combined with each other to form an alkylene group having 3–7 carbon atoms or a —S—$R_{11}$ group wherein $R_{11}$ is a furanyl group or a pyridyl group, which comprises (a) reacting a compound of the formula

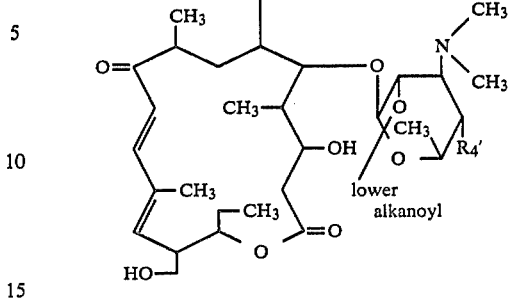

wherein $R_4$, is a hydrogen atom or a lower alkanoyloxy group with a compound of the formula

wherein X and X' are the same or different halogen atoms, to produce a compound of the formula

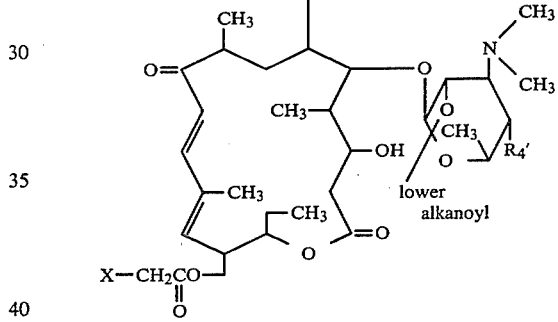

wherein X and $R_4$, have the same significance as defined above, (b) reacting the product with a compound of the formula

wherein $R_9$ and $R_{10}$ have the same significance as defined above or a compound of the formula

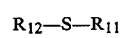

wherein $R_{12}$ is an alkali metal atom and $R_{11}$ has the same significance as defined above, (c) treating the product with an alcohol, and (d) removing the protective group for the aldehyde group.

9. A method of producing a 19-decarbonyl-4'-deoxymycaminosyl tylonolide as claimed in claim 1 of the formula

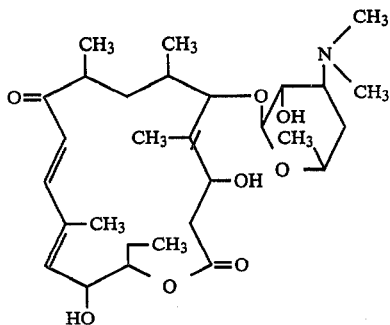

which comprises reacting 4'-deoxymycaminosyl tylonolide with chlorotris(triphenylphosphine)rhodium.

10. A method of producing a tylosin compound as claimed in claim 1 of the formula

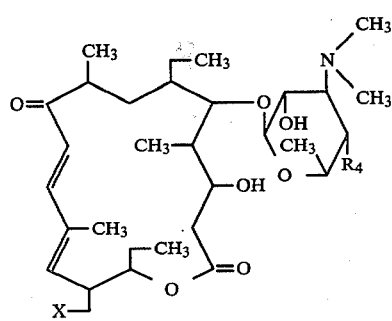

wherein X is a halogen atom and $R_4$ is a hydrogen atom or a hydroxyl group, which comprises halogenating a compound of the formula

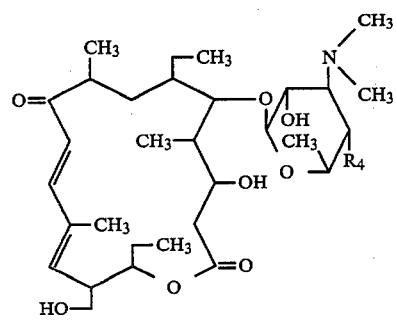

wherein $R_4$ has the same significance as defined above.

11. A method of producing a tylosin compound of the formula

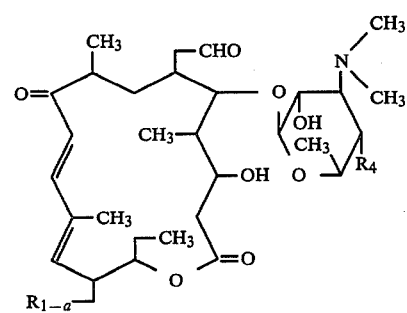

wherein $R_{1-a}$ is a

group, $R_5$ is a hydrogen atom or a lower alkyl group which is unsubstituted or substituted by a hydroxyl group and $R_6$, is a hydrogen atom, a lower alkyl group which is unsubstituted or substituted by a hydroxyl group, an aryl group, an aralkyl group, or a cycloalkyl group having 3–10 carbon atoms; a —N(CH$_2$)$_n$ group wherein n is an integer of 2–15 which is unsubstituted or substituted by an oxo group, a hydroxyl group, a lower alkyl group, or a hydroxyl lower alkyl group; or an imidazolyl group, a morpholino group, or a piperazino group each of which is unsubstituted or substituted by a lower alkyl group and $R_4$ is a hydrogen atom or a hydroxyl group which comprises (a) catalytically reducing a compound of the formula

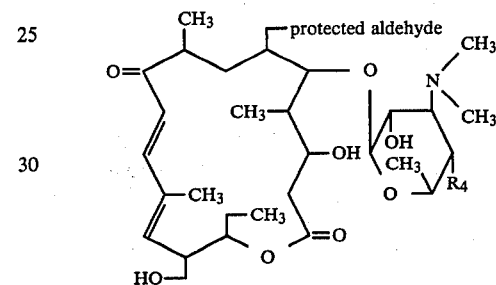

wherein $R_4$ has the same significance as defined above, (b) halogenating the product, (c) reacting the halogenated product with a compound of the formula

$R_{1-a}$—H wherein $R_{1-a}$ has the same significance as defined above, and (d) removing the protective group for the aldehyde group.

12. A method of producing a tylosin compound of the formula

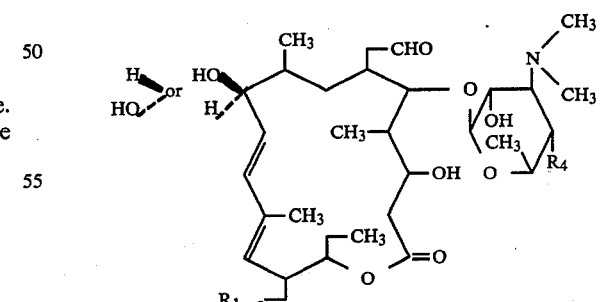

according to claim 6, wherein $R_{1-a}$ is an

group wherein $R_5$ is a hydrogen atom or a lower alkyl group which is unsubstituted or substituted by a hydroxyl group and $R_6$, is a hydrogen atom, a lower alkyl group which may be substituted by a hydroxyl group, an aryl group, an aralkyl group, or a cycloalkyl group having 3–10 carbon atoms; a $-N(CH_2)_n$ group wherein n is an integer of 2–15 which is unsubstituted or substituted by an oxo group, a hydroxyl group, a lower alkyl group, or a hydroxy lower alkyl group; or an imidazolyl group, a morpholino group, or a piperazino group each of which is unsubstituted or substituted by a lower alkyl group and $R_4$ is a hydrogen atom or a hydroxyl group which comprises (a) reducing a compound of the formula

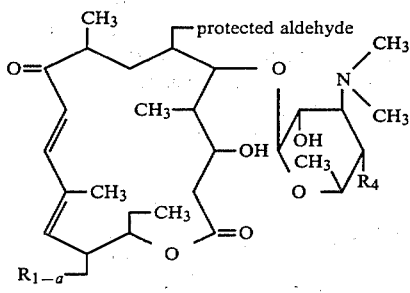

wherein $R_{1-a}$ and $R_4$ have the same significance as defined in the above formula, with a hydrogenated metal complex compound and (b) removing the protective group for the aldehyde group.

13. A method of producing a tylosin compound as claimed in claim 1 of the formula

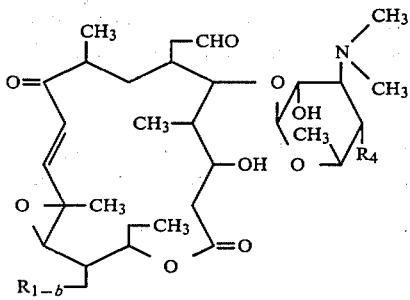

wherein $R_{1-b}$ is a hydroxyl group; a

group wherein $R_5$ is a hydrogen atom or a lower alkyl group which is unsubstituted or substituted by a hydroxyl group and $R_{6'}$ is a hydrogen atom, a lower alkyl group which is unsubstituted or substituted by a hydroxyl group, an aryl group, an aralkyl group, or a cycloalkyl group having 3–10 carbon atoms; $-N(CH_2)_n$ group wherein n is an integer of 2–15 which is unsubstituted or substituted by an oxo group, a hydroxyl group, a lower alkyl group, or a hydroxy lower alkyl group; or an imidazolyl group, a morpholino group, or a piperazino group each of which is unsubstituted or substituted by a lower alkyl group and $R_4$ is a hydrogen atom or a hydroxyl group, which comprises (a) reacting a compound of the formula

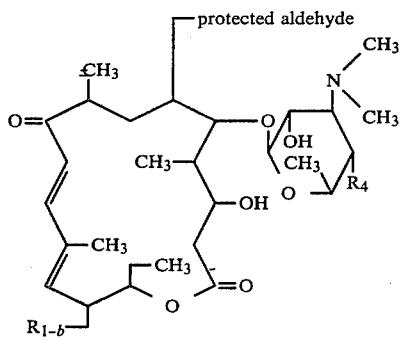

wherein $R_{1-b}$ and $R_4$ have the same significance as defined above, with a peracid, (b) reacting the product with triphenylphosphine, and (c) removing the protective group for the aldehyde group.

14. A method of producing a tylosin compound as claimed in claim 1 of the formula

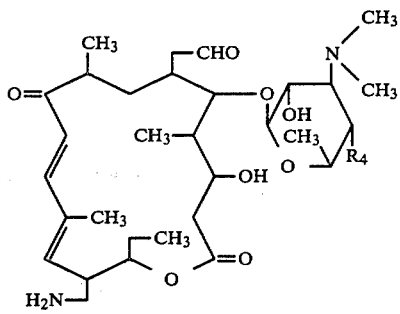

wherein $R_4$ is a hydrogen atom or a hydroxyl group, which comprises (a) reacting a compound of the formula

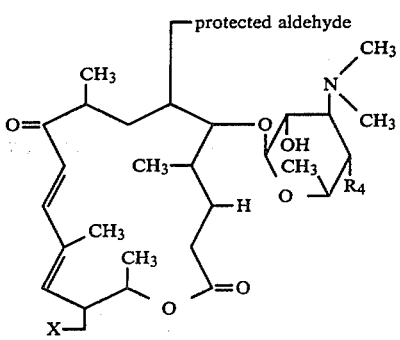

wherein X is a halogen atom, and $R_4$ has the same significance as defined above, with sodium azide, (b) reacting the product with an aqueous chromium chloride solution, and (c) removing the protective group for the aldehyde group.

15. A method of producing a tylosin compound as claimed in claim 1 of the formula

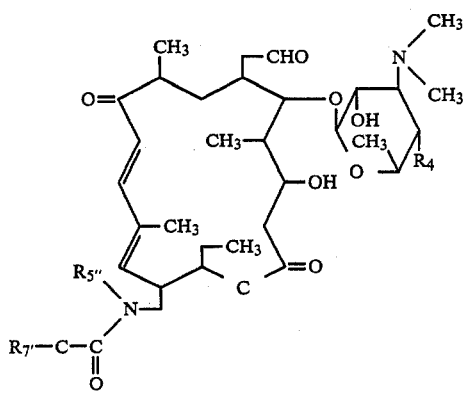

wherein R₄ is a hydrogen atom or a hydroxyl group, R₅″ is a hydrogen atom or a lower alkyl group, and R₇′ is a lower alkyl group, an aryl group, or an aralkyl group, which comprises (a) reacting a compound of the formula

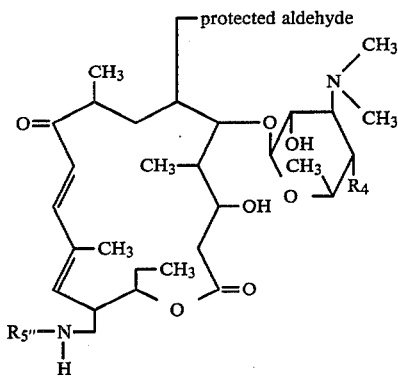

wherein R₄ and R₅″ have the significance as defined above with a compound of the formula

X—COO—R₇′ wherein X is a halogen atom and R₇′ has the same significance as defined above, and (b) removing the protective group for the aldehyde group.

16. A method of producing a tylosin compound as claimed in claim 1 of the formula

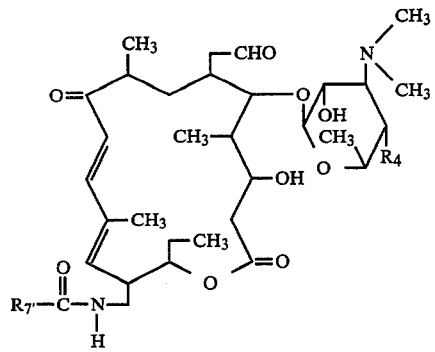

wherein R₄ represents a hydrogen atom or a hydroxyl group and R₇′ represents a lower alkyl group, an aryl group, or an aralkyl group which comprises (a) reacting a compound of the formula

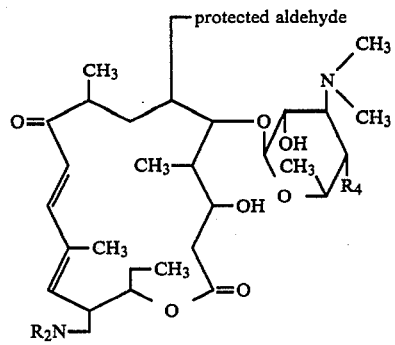

wherein R₄ has the same significance as defined above, with a compound of the formula

R₇′—COOH wherein R₇′ has the same significance as defined above, or the reactive derivative thereof, and (b) removing the protective group for the aldehyde group.

17. A method of producing a tylosin compound as claimed in claim 1 of the formula

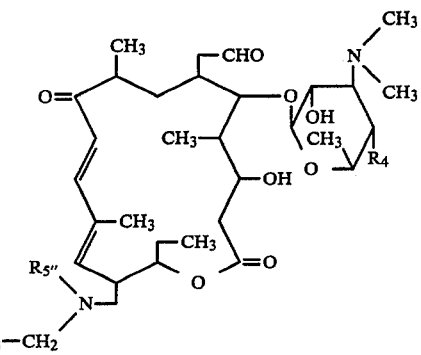

wherein R₄ is a hydrogen atom or a hydroxyl group, R₅″ is a hydrogen atom or a lower alkyl group, and R₁₃ is a mono-, di- or trifluoromethyl group, which comprises (a) reacting a compound of the formula

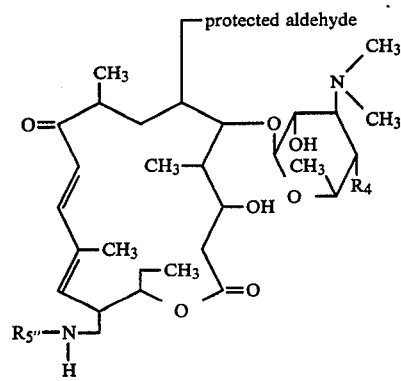

wherein R₄ and R₅″ have the same significance as defined above, with a compound of the formula

R₁₃—CH₂OSO₂CF₃ wherein $R_{13}$ has the same significance as defined above, and (b) removing the protective group for the aldehyde group.

18. A method for producing a tylosin compound as claimed in claim 1 of the formula

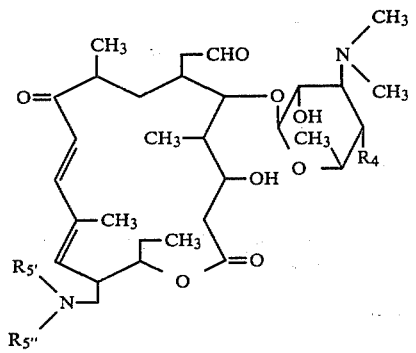

wherein $R_4$ is a hydrogen atom or a hydroxyl group, $R_{5'}$ is a lower alkyl group, and $R_{5''}$ is a hydrogen atom or a lower alkyl group, which comprises (a) reacting a compound of the formula

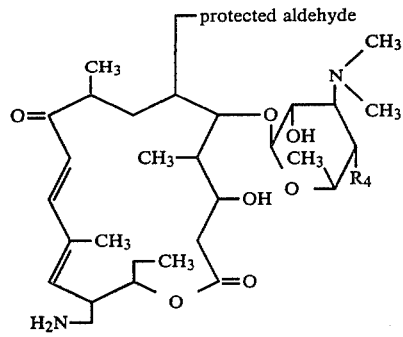

wherein $R_4$ has the same significance as defined above, with a lower alkyl halide and (b) removing the protective group for the aldehyde group.

* * * * *